US010278967B2

(12) United States Patent
Huntley et al.

(10) Patent No.: US 10,278,967 B2
(45) Date of Patent: May 7, 2019

(54) ACETATE SALT OF BUPRENORPHINE AND METHODS FOR PREPARING BUPRENORPHINE

(71) Applicant: Rhodes Technologies, Coventry, RI (US)

(72) Inventors: C. Frederick M. Huntley, East Greenwich, RI (US); Erik Wayne Kataisto, Coventry, RI (US); Helge Alfred Reisch, Westerly, RI (US); Archana Sharma, East Greenwich, RI (US)

(73) Assignee: Rhodes Technologies, Coventry, RI (US)

( * ) Notice: Subject to any disclaimer, the term of this patent is extended or adjusted under 35 U.S.C. 154(b) by 0 days.

(21) Appl. No.: 15/894,520

(22) Filed: Feb. 12, 2018

(65) Prior Publication Data

US 2018/0162866 A1 Jun. 14, 2018

Related U.S. Application Data

(60) Division of application No. 15/446,197, filed on Mar. 1, 2017, now Pat. No. 9,926,329, which is a continuation of application No. 15/507,453, filed as application No. PCT/IB2016/051332 on Mar. 9, 2016.

(60) Provisional application No. 62/131,114, filed on Mar. 10, 2015.

(51) Int. Cl.
*A61P 25/04* (2006.01)
*A61K 31/485* (2006.01)
*C07D 489/12* (2006.01)

(52) U.S. Cl.
CPC ............ *A61K 31/485* (2013.01); *A61P 25/04* (2018.01); *C07D 489/12* (2013.01); *C07B 2200/13* (2013.01)

(58) Field of Classification Search
None
See application file for complete search history.

(56) References Cited

U.S. PATENT DOCUMENTS

| 2,191,786 | A | 2/1940 | Aronow |
|---|---|---|---|
| 2,583,420 | A | 1/1952 | Garber et al. |
| 3,355,486 | A | 11/1967 | Berkowitz et al. |
| 3,536,809 | A | 10/1970 | Applezweig |
| 3,598,123 | A | 8/1971 | Zaffaroni |
| 3,749,646 | A | 7/1973 | Pirt |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 4,217,787 | A | 8/1980 | Liebing et al. |
| 4,830,028 | A | 5/1989 | Lawson et al. |
| 5,059,595 | A | 10/1991 | Le Grazie |
| 5,073,543 | A | 12/1991 | Marshall et al. |
| 5,120,548 | A | 6/1992 | McClelland et al. |
| 5,354,556 | A | 10/1994 | Sparks et al. |
| 5,591,767 | A | 1/1997 | Mohr et al. |
| 5,639,476 | A | 6/1997 | Oshlack et al. |
| 5,674,533 | A | 10/1997 | Santus et al. |
| 5,698,155 | A | 12/1997 | Grosswald et al. |
| 5,733,566 | A | 3/1998 | Lewis |
| 6,264,980 | B1 | 7/2001 | Hille |
| 6,344,211 | B1 | 2/2002 | Hille |
| 6,486,692 | B1 | 11/2002 | Chen |
| 6,994,827 | B2 | 2/2006 | Safir et al. |
| RE41,408 | E | 6/2010 | Reder et al. |
| RE41,489 | E | 8/2010 | Reder et al. |
| RE41,571 | E | 8/2010 | Reder et al. |
| 7,842,307 | B2 | 11/2010 | Oshlack et al. |
| 7,982,056 | B2 | 7/2011 | Bydlinski et al. |
| 8,058,439 | B2 | 11/2011 | Cox et al. |
| 8,075,872 | B2 | 12/2011 | Arkenau-Maric et al. |
| 8,114,383 | B2 | 2/2012 | Bartholomaus et al. |
| 8,192,722 | B2 | 6/2012 | Arkenau-Maric et al. |
| 8,309,060 | B2 | 11/2012 | Bartholomaus et al. |
| 8,337,888 | B2 | 12/2012 | Wright et al. |
| 8,492,547 | B2 | 7/2013 | Antonini |
| 8,524,275 | B2 | 9/2013 | Oshlack et al. |
| 8,529,948 | B1 | 9/2013 | Wright et al. |
| 8,609,683 | B2 | 12/2013 | Wright et al. |
| 8,946,253 | B2 | 2/2015 | Hummel et al. |
| 8,957,238 | B2 | 2/2015 | Gutman et al. |

(Continued)

FOREIGN PATENT DOCUMENTS

EP 0368409 A2 5/1990
WO WO 2013/088254 6/2013

(Continued)

OTHER PUBLICATIONS

ASTM Standard E203-08 ("Standard Test Method for Water Using Volumetric Karl Fischer Titration") (2008).
Bourhis et al., "The anatomy of a comprehensive constrained, restrained refinement program for the modern computing environment—Olex2 dissected," *Acta Cryst.* A71:1-17 (2014).
Challener, "Polymorph Screening for Identification of Relevant Crystalline Forms," *Pharmaceutical Technol.* 40(3):32-35 (2016).
Dolomanov et al., "Olex2: a complete structure solution, refinement and analysis program," *J Appl Cryst.* 42:339-341 (2009).
European Directorate for the Quality of Medicines & Health Care, Strasbourg, France (#Y0001122) (2015).
European Pharmacopoeia Monograph 1180, Buprenorphine (corrected) (2009).
European Pharmacopoeia Monograph 1181, Buprenorphine Hydrochloride (2005).

(Continued)

*Primary Examiner* — Zinna Northington Davis
(74) *Attorney, Agent, or Firm* — Dechert LLP

(57) ABSTRACT

The present disclosure provides acetate salts of buprenorphine, and its anhydrates, solvates, hydrates, and crystalline forms thereof, where the acetate salts of buprenorphine are essentially free of impurities. The disclosure further provides method of preparing the acetate salts, buprenorphine free base prepared from the acetate salts, other salts prepared from the free base, and pharmaceutical compositions thereof essentially free of impurities.

22 Claims, 6 Drawing Sheets

(56) References Cited

U.S. PATENT DOCUMENTS

| | | | |
|---|---|---|---|
| 9,012,469 B2* | 4/2015 | Aslund et al. | C07D 489/04 514/282 |
| 2010/0119585 A1 | 5/2010 | Hille et al. | |
| 2011/0009633 A1 | 1/2011 | Antonini | |
| 2014/0363487 A1 | 12/2014 | Hille et al. | |

FOREIGN PATENT DOCUMENTS

| | | |
|---|---|---|
| WO | WO 2014/090921 | 6/2014 |
| WO | WO 2014/195352 | 12/2014 |

OTHER PUBLICATIONS

Goodson, "Dental Applications," pp. 115-138 (Chapter 6) in *Medical Applications of Controlled Release*, vol. 2, *Applications and Evaluation*, Langer and Wise, eds., CRC Press, Boca Raton, FL (1984).

Gordon et al., "Relative Response Factor for Lamivudine and Zidovudine Related Substances by RP-HPLC with DAD Detection," *Chem. Materials Res.* 6(12):160-165 (2014).

Grupp et al., "Protection against Hypoxia-reoxygenation in the Absence of Poly (ADP-ribose) Synthetase in Isolated Working Hearts," *J. Mol. Cell Cardiol.* 31:297-303 (1999).

*Handbook of Pharmaceutical Excipients*, Amer. Pharmaceutical Ass'n, Washington, DC (1986).

ICH Harmonised Tripartite Guideline Stability Testing: Photostability Testing of New Drug Substances and Products Q1B, Current Step 4 Version (1996).

ISO 760:1978 ("Determination of Water—Karl Fischer Method") (1978).

International Search Report and Written Opinion corresponding to International Application No. PCT/IB2016/051332 dated Apr. 25, 2016.

King, "Tablets, Capsules, and Pills," pp. 1553-1593 in *Remington's Pharmaceutical Sciences*, Osol, ed., 16$^{th}$ Ed., Mack Publishing, Easton, PA (1980).

Langer et al., "Chemical and Physical Structure of Polymers as Carriers for Controlled Release of Bioactive Agents: A Review," *J. Macromol. Sci. Rev. Macromol. Chem.* C23(1):61-126 (1983).

Langer, "New Methods of Drug Delivery," *Science* 249:1527-1533 (1990).

Luft et al., "Lessons from high-throughput protein crystallization screening: 10 years of practical experience," *Expert Opin. Drug Discov.* 6(5):465-480 (2011).

Morissette et al., "High-throughput crystallization: polymorphs, salts, co-crystals and solvates of pharmaceutical solids," *Adv. Drug Delivery Rev's* 56:275-300 (2004).

*Pharmaceutical Dosage Forms: Disperse Systems*, Lieberman et al., eds., 2$^{nd}$ Ed., Marcel Dekker, Inc., New York (1996 and 1998).

*Pharmaceutical Dosage Forms: Tablets*, Lieberman et al., eds., 2$^{nd}$ Ed., Marcel Dekker, Inc., New York (1989 and 1990).

Puschmann et al.,"[MS45-P09] Olex2—a complete package for molecular crystallography," *Acta Cryst.* A69:s679 (2013).

Radebough et al., "Preformulation," pp. 1447-1676 in *Remington's Pharmaceutical Sciences* vol. 2, Gennaro, ed., 19th Ed., Mack Publishing, Easton, PA (1995).

Saudek et al., "A Preliminary Trial of the Programmable Implantable Medication System for Insulin Delivery," *New Engl. J. Med.* 321:574-579 (1989).

Sayre et al., "Importance of C-6 Chirality in Conferring Irreversible Opioid Antagonism to Naltrexone-Derived Affinity Labels," *J. Med. Chem.* 26(9):1229-1235 (1983).

Treat et al., "Liposome Encapsulated Doxorubicin Preliminary Results of Phase I and Phase II Trials," pp. 317-327 and 353-365 in *Liposomes in the Therapy of Infectious Disease and Cancer*, Lopez-Berenstein et al., eds., Lake Tahoe, CA (1989).

* cited by examiner

ACETATE SALT OF BUPRENORPHINE AND METHODS FOR PREPARING BUPRENORPHINE

1. BACKGROUND

Buprenorphine is an opioid used to treat opioid addiction and control pain, such as moderate pain. Traditional methods for the synthesis of buprenorphine use thebaine or oripavine as the starting material. These known methods of buprenorphine synthesis typically result in a level of impurities that is higher than the level acceptable according to guidelines of the International Harmonisation of Technical Requirements for Registration of Pharmaceuticals for Human Use ("ICH"). Examples of impurities that can be present at unacceptable levels in preparations of buprenorphine include (4R,4aS,6R,7R,7aR,12bS)-3-(but-3-en-1-yl)-6-((S)-2-hydroxy-3,3-dimethylbutan-2-yl)-7-methoxy-1,2,3,4,5,6,7,7a-octahydro-4a,7-ethano-4,12-methanobenzofuro[3,2-e]isoquinolin-9-ol and (4R,4aS,6R,7R,7aR,12bS)-3-(cyclopropylmethyl)-6-((S)-2-hydroxy-3,3-dimethylbutan-2-yl)-1,2,3,4,5,6,7,7a-octahydro-4a,7-ethano-4,12-methanobenzofuro[3,2-e]isoquinoline-7,9-diol. Some methods of purification, such as chromatography, e.g., as disclosed in U.S. Pat. No. 8,492,547, may provide buprenorphine with an acceptable level of impurities but have associated higher costs or are difficult to apply on a commercial scale. Accordingly, there is a need for alternative pathways for preparing buprenorphine containing acceptable levels of impurities.

2. SUMMARY

One aspect of the disclosure relates to an acetate salt of buprenorphine.

Another aspect of the disclosure relates to buprenorphine acetate tetrahydrate.

Another aspect of the disclosure relates to a crystalline form of the acetate salt of buprenorphine.

Another aspect of the disclosure relates to a crystalline form of buprenorphine acetate tetrahydrate.

Another aspect of the disclosure relates to a method for preparing an acetate salt of buprenorphine, comprising the steps of:
 (a) contacting buprenorphine free base with a solution comprising acetic acid in a dissolution vessel to form an admixture, wherein the admixture is at a temperature of from about 40° C. to about 80° C.;
 (b) optionally filtering the admixture of step (a);
 (c) adding an agent to the admixture produced in step (a) or (b) to precipitate the acetate salt of buprenorphine; and
 (d) isolating the acetate salt of buprenorphine precipitated in step (c).

Another aspect of the disclosure relates to a method for preparing buprenorphine free base comprising the steps of:
 (a) contacting an acetate salt of buprenorphine with a solution and a basic material to form an admixture;
 (b) agitating the admixture of step (a) at a temperature of from about 20° C. to about 90° C. to provide buprenorphine free base;
 (c) isolating the buprenorphine free base of step (b); and
 (d) optionally repeating steps (a) through (c) one or more times.

Another aspect of the disclosure relates to a method for preparing buprenorphine free base comprising treating an acetate salt of buprenorphine at a pressure, temperature and for a time sufficient to remove the acetic acid and water, thereby providing the buprenorphine free base.

Another aspect of the disclosure relates to a method for preparing buprenorphine free base, comprising the steps of:
 (a) dissolving an acetate salt of buprenorphine in a solution to form an admixture;
 (b) optionally filtering the admixture of step (a);
 (c) adding a basic material to the admixture in step (a) or (b) to form a second admixture;
 (d) adding an anti-solvent to the second admixture produced in step (c) to form a precipitate of the buprenorphine free base; and
 (e) isolating the precipitate from step (d).

Another aspect of the disclosure relates to a method for preparing buprenorphine free base comprising:
 (a) heating an admixture of an acetate salt of buprenorphine and an aqueous solution to provide precipitated buprenorphine free base; and
 (b) filtering the admixture of step (a).

Another aspect of the disclosure relates to a method for preparing buprenorphine free base comprising:
 (a) mixing an acetate salt of buprenorphine in a solvent to form an admixture;
 (b) refluxing the admixture at a reflux temperature and removing the acetate as acetic acid in the vapor phase;
 (c) cooling the admixture to provide precipitated buprenorphine free base; and
 (d) isolating the buprenorphine free base.

Buprenorphine acetate hydrate or a composition containing buprenorphine acetate hydrate is useful for treating or preventing: pain, constipation, drug abuse, an addictive disorder, vomiting, respiratory depression, or euphoria (each hereafter being a "Condition").

3. BRIEF DESCRIPTION OF THE FIGURES

4. DETAILED DESCRIPTION

Figure 1:
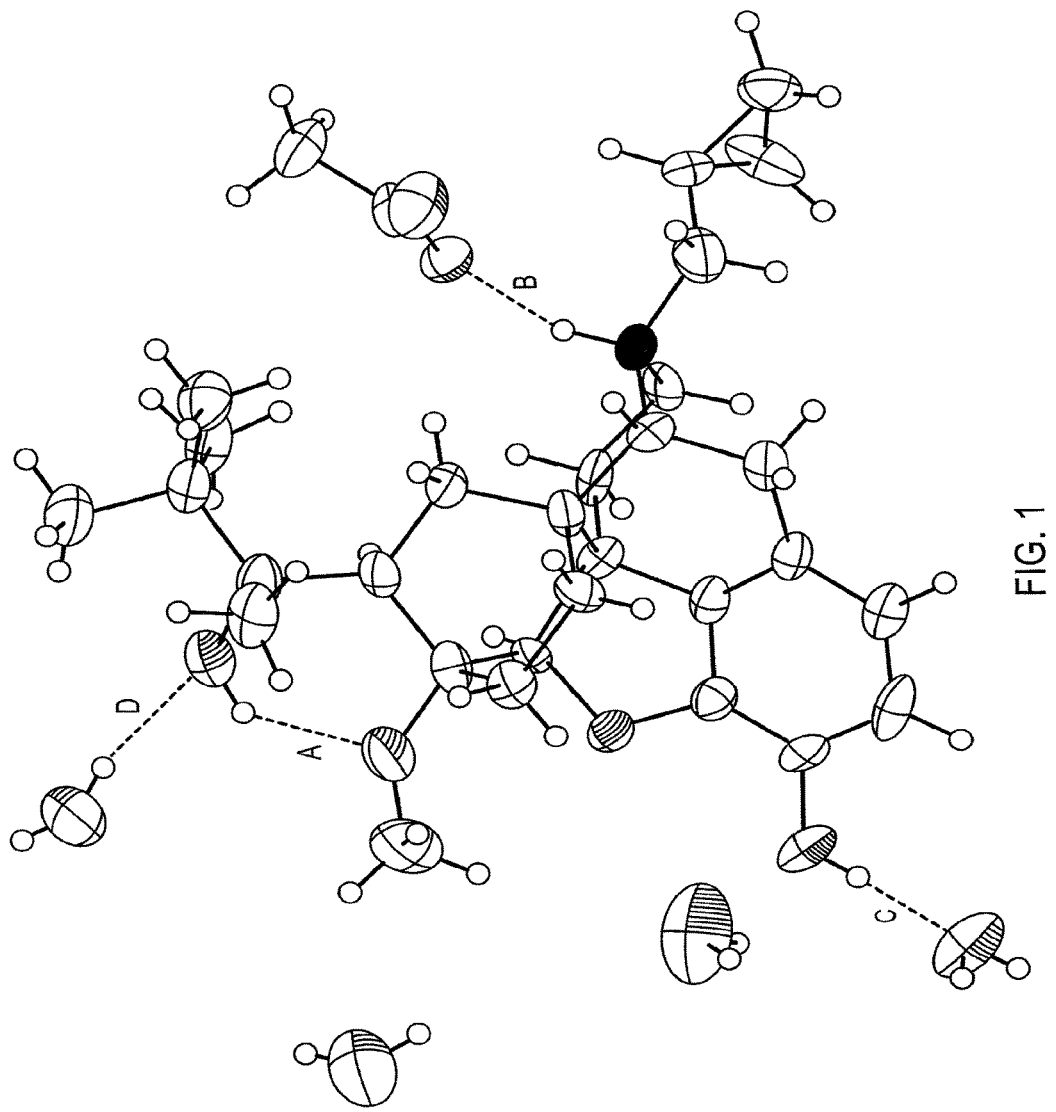
FIG. 1 shows a thermal ellipsoid representation of buprenorphine acetate tetrahydrate with selected hydrogen bonds.

The invention includes the following:
 (1) An acetate salt of buprenorphine.
 (2) The acetate salt of buprenorphine of the above (1), comprising a hydrate.
 (3) The acetate salt of buprenorphine of the above (2), wherein the hydrate comprises from 1 to 6 water molecules per molecule of the acetate salt of buprenorphine.
 (4) The acetate salt of buprenorphine of the above (3), wherein the hydrate is a tetrahydrate.
 (5) A purified acetate salt of buprenorphine of any one of the above (1) to (4).

(6) The purified acetate salt of buprenorphine of the above (5), which is an essentially pure acetate salt of buprenorphine.

(7) A crystalline form of the acetate salt of buprenorphine of any one of the above (1) to (6).

(8) A crystalline form of the acetate salt of buprenorphine of the above (4).

(9) The crystalline form of the above (8), characterized by an X-ray powder diffraction pattern obtained by exposure to CuKα radiation comprising peaks at 2θ angles substantially equivalent to at least the peaks at 16.21 and 18.70, and having at least one additional peak at a 2θ angle substantially equivalent to the peaks at 8.77, 10.31, or 18.47.

(10) The crystalline form of the above (8), characterized by an X-ray powder diffraction pattern obtained by exposure to CuKα radiation comprising peaks at 2θ angles substantially equivalent to at least the peaks at 8.77, 10.31, 16.21, 18.47, and 18.70, and having at least one additional peak at a 2θ angle substantially equivalent to the peaks at 6.38, 11.93, or 19.40.

(11) The crystalline form of the above (8), characterized by an X-ray powder diffraction pattern obtained by exposure to CuKα radiation comprising peaks at diffraction angles substantially equivalent to at least the peaks at those in the following table:

| Position [°2Theta] |
| --- |
| 6.38 |
| 8.77 |
| 10.31 |
| 11.93 |
| 16.21 |
| 18.47 |
| 18.70 |
| 19.40 |

Figure 4:
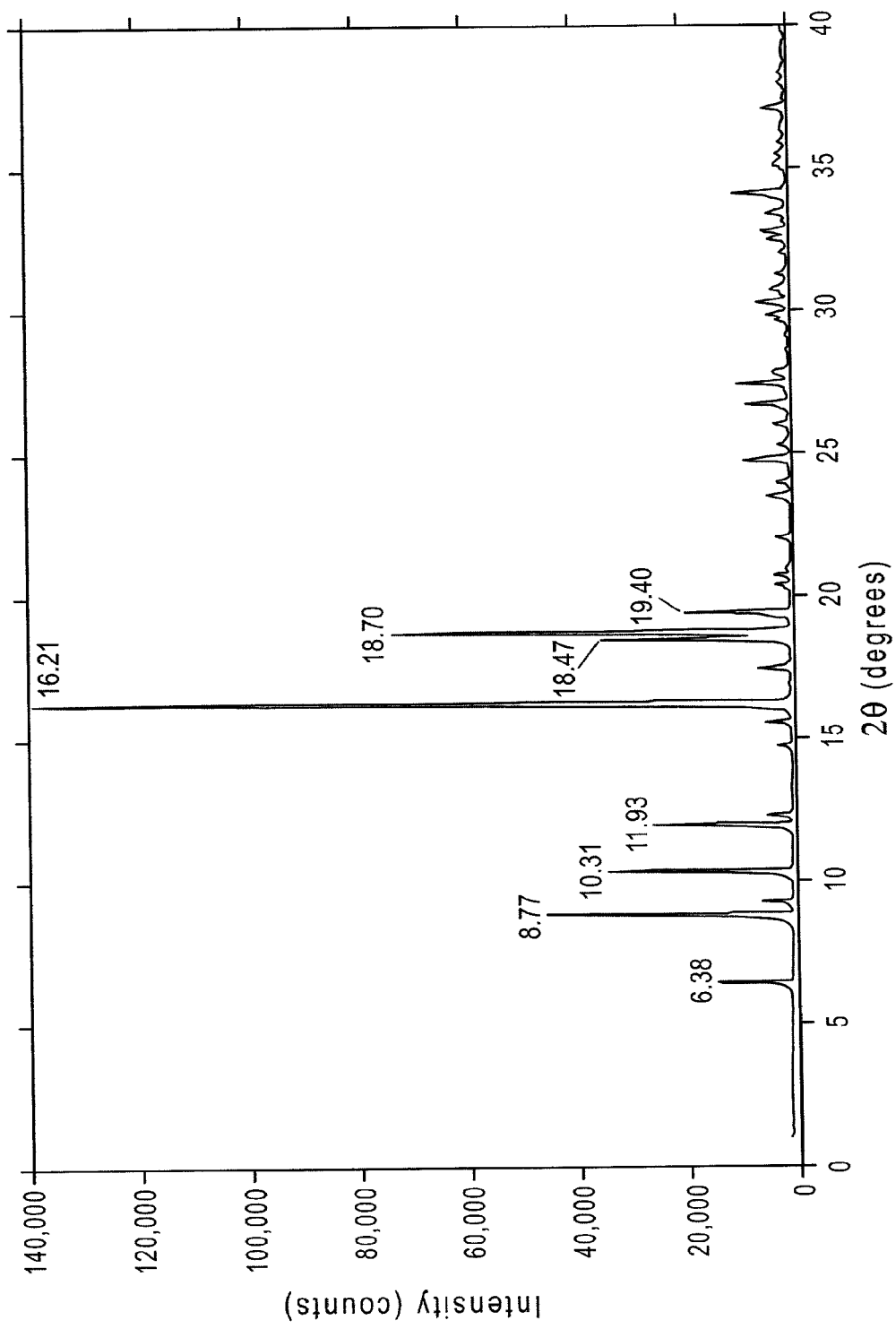
FIG. 4 shows an X-ray powder diffraction ("XRPD") pattern of buprenorphine acetate tetrahydrate obtained using CuKα radiation.

(12) The crystalline form of the above (8), which has an X-ray powder diffraction pattern substantially the same as the X-ray powder diffraction pattern shown in FIG. 4 when measuring using CuKα radiation.

(13) The crystalline form of any one of the above (8) to (12), wherein the crystalline form exhibits a first transition region with at least one peak position at from about 50° C. to about 140° C. as measured by a heat flow differential scanning calorimeter at a heating rate of about 10° C. per minute.

(14) The crystalline form of any one of the above (8) to (13), wherein the crystalline form exhibits a second transition region having a peak position at from about 217° C. to about 225° C. as measured by a heat flow differential scanning calorimeter at a heating rate of about 10° C. per minute.

(15) The crystalline form of the above (14), which exhibits an integral ratio of from about 7 to about 8 for the first transition region at from about 50° C. to about 140° C. relative to the second transition region at from about 217° C. to about 225° C., wherein the integrals are determined over the temperature ranges of from about 35° C. to about 180° C. and from about 203° C. to about 233° C., respectively.

(16) The crystalline form of the above (15), wherein the crystalline form exhibits an integral ratio of from about 7.1 to about 7.8.

(17) The crystalline form of any one of the above (8) to (16), characterized in that it is a monoclinic crystal.

(18) The crystalline form of the above (17), wherein the unit cell parameters are a=10.5±0.5 Å, b=10.9±0.5 Å, and c=14.4±0.5 Å.

(19) The crystalline form of the above (17), wherein the unit cell parameters are a=10.52±0.05 Å, b=10.92±0.05 Å, and c=14.44±0.05 Å.

(20) The crystalline form of any one of the above (17) to (19), wherein the space group is $P2_1$.

(21) A pharmaceutical composition comprising the acetate salt of buprenorphine of any one of the above (1) to (6) or the crystalline form of any of the above (7) to (20), and a pharmaceutically acceptable carrier.

(22) A method for treating pain, constipation, drug abuse, an addictive disorder, vomiting, respiratory depression, or euphoria comprising administering to an animal in need thereof an effective amount of the acetate salt of buprenorphine of any one of the above (1) to (6), the crystalline form of any of the above (7) to (20) or the pharmaceutical composition of the above (21).

(23) A method for treating pain comprising administering to an animal in need thereof an effective amount of the acetate salt of buprenorphine of any one of the above (1) to (6), the crystalline form of any of the above (7) to (20) or the pharmaceutical composition of the above (21).

(24) A method for preparing an acetate salt of buprenorphine, comprising the steps of:
(a) contacting buprenorphine free base with a solution comprising acetic acid in a dissolution vessel to form an admixture, wherein the admixture is at a temperature of from about 40° C. to about 80° C.;
(b) optionally filtering the admixture of step (a);
(c) adding an agent to the admixture produced in step (a) or (b) to precipitate the acetate salt of buprenorphine; and
(d) isolating the acetate salt of buprenorphine precipitated in step (c).

(25) The method of the above (24), wherein in step (a) the buprenorphine free base is contacted with from about 2 mass equivalents to about 6 mass equivalents of the solution comprising acetic acid relative to the starting mass of the free base.

(26) The method of the above (24), wherein the buprenorphine free base is contacted with from about 3 mass equivalents to about 5 mass equivalents of the solution comprising acetic acid relative to the starting mass of the free base.

(27) The method of any one of the above (24) to (26), wherein the solution comprising acetic acid is an aqueous solution.

(28) The method of the above (27), wherein the aqueous solution has from about 40 wt % to about 70 wt % acetic acid relative to the weight of the aqueous solution.

(29) The method of the above (27), wherein the aqueous solution has from about 45 wt % to about 60 wt % acetic acid relative to the weight of the aqueous solution.

(30) The method of any one of the above (24) to (29), wherein in step (a) the admixture is at a temperature of from about 40° C. to about 80° C. for a period of time such that a substantial portion of the buprenorphine free base has dissolved.

(31) The method of the above (30), wherein in step (a) the admixture is at a temperature of from about 45° C. to about 75° C. for a period of time such that a substantial portion of the buprenorphine free base has dissolved.

(32) The method of the above (30), wherein in step (a) the admixture is at a temperature of from about 50° C. to about 70° C. for a period of time such that a substantial portion of the buprenorphine free base has dissolved.

(33) The method of any one of the above (24) to (32), wherein in step (a) the admixture is agitated to accelerate dissolution of the buprenorphine free base.

(34) The method of the above (24), wherein the admixture of step (a) is filtered in step (b) in a filtration apparatus.

(35) The method of the above (34), wherein in step (b), the admixture of step (a) added to the filtration apparatus is at a temperature of from about 40° C. to about 80° C.

(36) The method of the above (34), wherein in step (b), the admixture of step (a) added to the filtration apparatus is at a temperature of from about 45° C. to about 75° C.

(37) The method of any one of the above (34) to (36), wherein an additional volume of a solution comprising acetic acid is used to rinse the dissolution vessel, the filtration apparatus or the dissolution vessel and the filtration apparatus.

(38) The method of the above (37), wherein the additional volume of the solution comprising acetic acid is from about 0.1 mass equivalents to about 2.0 mass equivalents relative to the starting mass of the buprenorphine free base in step (a).

(39) The method of the above (37), wherein the additional volume of the solution comprising acetic acid is from about 0.3 mass equivalents to about 0.5 mass equivalents relative to the starting mass of the buprenorphine free base in step (a).

(40) The method of any one of the above (37) to (39), wherein the additional volume of the solution is acetic acid in an aqueous solution.

(41) The method of the above (40), wherein the additional volume of the solution comprising acidic acid is an aqueous solution comprising acetic acid present at from about 40 wt % to about 70 wt % relative to the weight of the solution.

(42) The method of any one of the above (24) to (41), wherein in step (c) the agent is selected from an anti-solvent, a seed crystal, and combinations thereof.

(43) The method of the above (42), wherein the agent comprises an anti-solvent.

(44) The method of the above (43), wherein the anti-solvent comprises water.

(45) The method of the above (43) or (44), wherein from about 0.2 mass equivalents to about 8.0 mass equivalents of anti-solvent relative to the starting mass of free base in step (a) are added to the admixture of step (a) or (b).

(46) The method of any one of the above (43) to (45), wherein the anti-solvent is added at within about 10° C. of the temperature of the admixture of step (a) or step (b).

(47) The method of the above (46), wherein the anti-solvent is added at a temperature within about 5° C. of the temperature of the admixture of step (a) or step (b).

(48) The method of the above (42), wherein the agent comprises a seed crystal.

(49) The method of the above (48), wherein the seed crystal comprises an acetate salt of buprenorphine.

(50) The method of the above (49), wherein from about 0.1 wt % to about 5.0 wt % of seed crystal is added to the admixture of step (a) or (b) relative to the starting mass of the buprenorphine free base in step (a).

(51) The method of any one of the above (48) to (50), wherein the admixture of step (a) or (b) is at a temperature of from about 40° C. to about 80° C. when the seed crystal is added.

(52) The method of the above (51), wherein the admixture of step (a) or (b) is at a temperature of from about 55° C. to about 65° C. when the seed crystal is added.

(53) The method of the above (42), wherein a first amount of the anti-solvent is added followed by addition of the seed crystal.

(54) The method of the above (53), wherein the addition of the seed crystal is followed by the addition of a second amount of the anti-solvent.

(55) The method of the above (53) or (54), wherein the first amount of the anti-solvent is from about 0.2 mass equivalents to about 2.0 mass equivalents relative to the starting mass of the buprenorphine free base in step (a).

(56) The method of any one of the above (53) to (55), wherein from about 0.1 wt % to about 5.0 wt % of the seed crystal is added relative to the starting mass of the buprenorphine free base in step (a).

(57) The method of any one of the above (54) to (56), wherein the second amount of anti-solvent is from about 1.0 mass equivalent to about 6.5 mass equivalents relative to the starting mass of the buprenorphine free base in step (a).

(58) The method of any one of the above (24) to (57), further comprising cooling the admixture to a temperature of about 30° C. or lower following addition of the agent and prior to isolating the acetate salt of buprenorphine in step (d).

(59) The method of any one of the above (24) to (57), further comprising adding a co-solvent to the admixture following the precipitation of step (c) and prior to the isolating of the acetate salt of buprenorphine in step (d).

(60) The method of the above (59), wherein the co-solvent is selected from methanol, ethanol, isopropyl alcohol, and combinations thereof.

(61) The method of the above (59), wherein the co-solvent is isopropyl alcohol.

(62) The method of any one of the above (59) to (61), further comprising cooling the admixture to a temperature of about 30° C. or lower following addition of the co-solvent and prior to the isolating of the acetate salt of buprenorphine in step (d).

(63) The method of any one of the above (24) to (62), wherein the isolation in step (d) is accomplished by filtration.

(64) The method of any one of the above (24) to (63), further comprising slurrying the acetate salt of buprenorphine obtained from the isolation of step (d) with a slurrying solution comprising water and an alcohol, and filtering the acetate salt therefrom.

(65) A buprenorphine acetate salt product obtained from the method of any one of the above (24) to (64).

(66) The product of the above (65), wherein the product comprises about 0.10 wt % or less of a compound of formula (10):

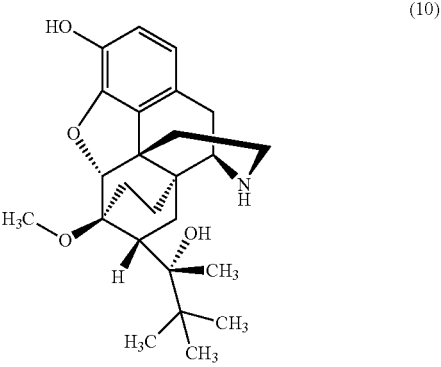

(10)

or a salt thereof.

(67) The product of the above (65) or (66), wherein the product comprises about 0.10 wt % or less of a compound of formula (11):

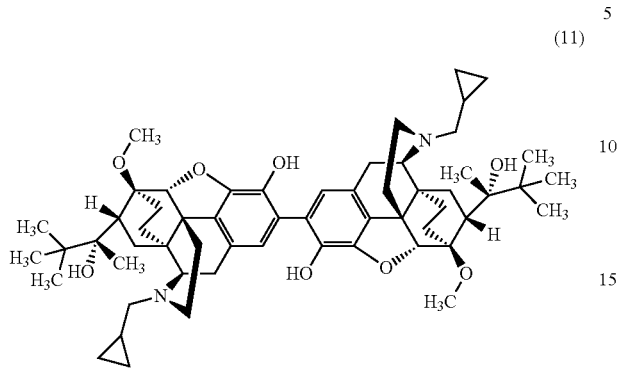

(11)

or a salt thereof.

(68) The product of any one of the above (65) to (67), wherein the product comprises about 0.10 wt % or less of a compound of formula (12):

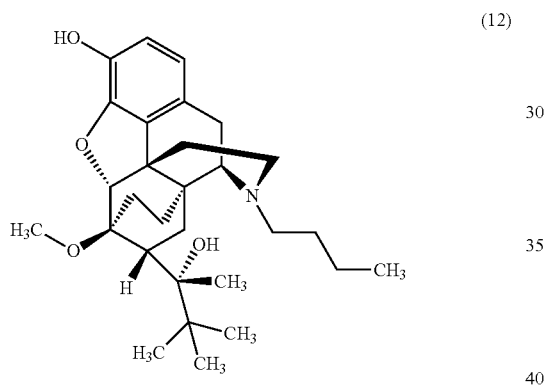

(12)

or a salt thereof.

(69) The product of the above (68), wherein the product comprises about 0.08 wt % or less of the impurity represented by the compound of formula (12) or a salt thereof.

(70) The product of any one of the above (65) to (69), wherein the product comprises about 0.10 wt % or less of a compound of formula (14):

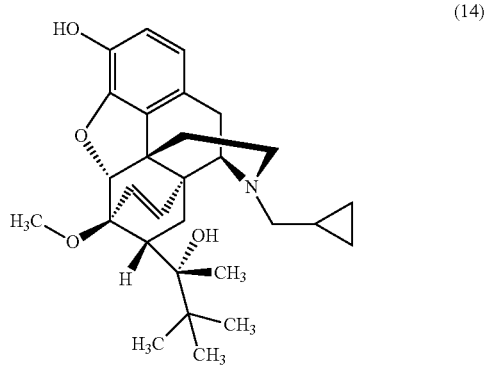

(14)

or a salt thereof.

(71) The product of any one of the above (65) to (70), wherein the product comprises about 0.10 wt % or less of a compound of formula (13):

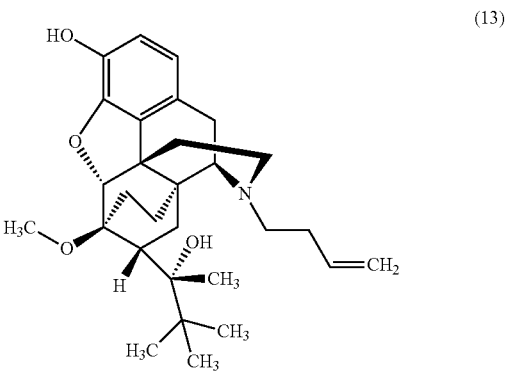

(13)

or a salt thereof.

(72) The product of any one of the above (65) to (71), wherein the product comprises about 0.10 wt % or less of a compound of formula (15):

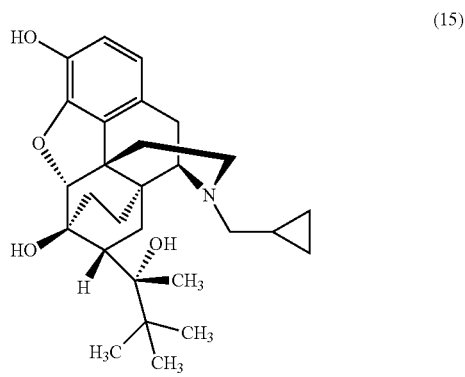

(15)

or a salt thereof.

(73) A pharmaceutical composition comprising the product of any one of the above (65) to (72) and a pharmaceutically acceptable carrier.

(74) A method for treating pain, constipation, drug abuse, an addictive disorder, vomiting, respiratory depression, or euphoria comprising administering to an animal in need thereof an effective amount of the product of any one of the above (65) to (72) or the pharmaceutical composition of the above (73).

(75) A method for treating pain comprising administering to an animal in need thereof an effective amount of the product of any one of the above (65) to (72) or the pharmaceutical composition of the above (73).

(76) A method for preparing buprenorphine free base comprising the steps of:
(a) contacting an acetate salt of buprenorphine with a solution and a basic material to form an admixture;
(b) agitating the admixture of step (a) at a temperature of from about 20° C. to about 90° C. to provide buprenorphine free base;
(c) isolating the buprenorphine free base of step (b); and
(d) optionally repeating steps (a) through (c) one or more times.

(77) The method of the above (76), wherein in step (a), the acetate salt of buprenorphine is contacted with at least about 1 mass equivalent of the solution relative to the starting mass of the acetate salt in step (a).

(78) The method of the above (76) or (77), wherein the solution of step (a) comprises water and an alcohol.

(79) The method of the above (78), wherein the solution comprises from about 30 wt % to about 70 wt % alcohol in water.

(80) The method of the above (78), wherein the solution comprises from about 40 wt % to about 60 wt % alcohol in water.

(81) The method of any one of the above (78) to (80), wherein the alcohol is selected from methanol, ethanol, isopropyl alcohol, and combinations thereof.

(82) The method of the above (81), wherein the alcohol is isopropyl alcohol.

(83) The method of the above (76), wherein the basic material is selected from a hydroxide, carbonate, alkoxide, hydride, phosphate, borate, oxide, cyanide, silicate, amine, and combinations thereof.

(84) The method of the above (76), wherein the acetate salt of buprenorphine is contacted with from about 0.5 molar equivalents to about 20 molar equivalents of basic material relative to starting moles of the acetate salt of buprenorphine in step (a).

(85) The method of the above (84), wherein the acetate salt of buprenorphine is contacted with from about 1 molar equivalent to about 10 molar equivalents of basic material relative to the starting moles of acetate salt of buprenorphine in step (a).

(86) The method of any one of the above (76) to (85), wherein the admixture of step (a) is agitated in step (b) for from about 1 hour to about 36 hours.

(87) The method of the above (86), wherein agitating step (b) takes from about 2 hours to about 8 hours.

(88) The method of the above (86) or (87), wherein in step (b) the admixture is agitated at a temperature of from about 25° C. to about 90° C.

(89) The method of the above (88), wherein in step (b) the admixture is agitated at a temperature of from about 30° C. to about 45° C.

(90) The method of any one of the above (76) to (89), wherein the isolating in step (c) is accomplished by filtration.

(91) The method of any one of the above (76) to (90), further comprising a step of slurrying the buprenorphine free base of step (c) with a slurrying solution comprising water and an alcohol, and filtering the free base therefrom.

(92) A buprenorphine free base product obtained from the method of any one of the above (76) to (91).

(93) The product of the above (92), wherein the product comprises about 0.10 wt % or less of a compound of formula (10):

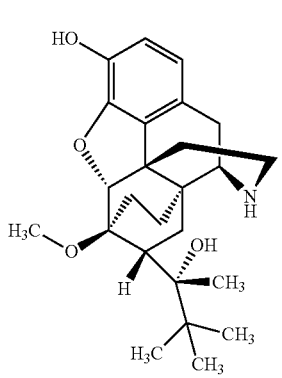

(94) The product of the above (92) or (93), wherein the product comprises about 0.10 wt % or less of a compound of formula (11):

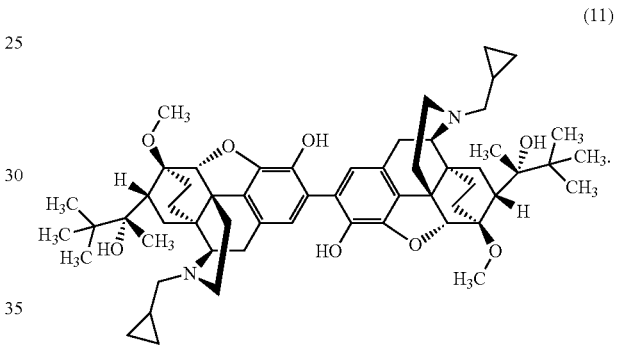

(95) The product of any one of the above (92) to (94), wherein the product comprises about 0.10 wt % or less of a compound of formula (12):

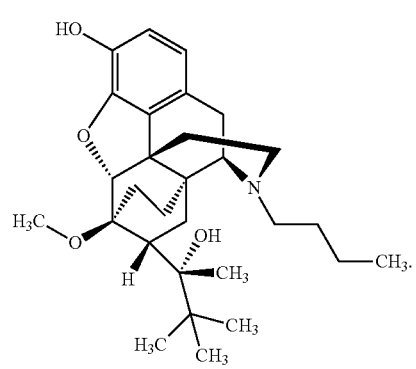

(96) The product of the above (95), wherein the product comprises about 0.08 wt % or less of the impurity represented by the compound of formula (12).

(97) The product of any one of the above (92) to (96), wherein the product comprises about 0.10 wt % or less of a compound of formula (14):

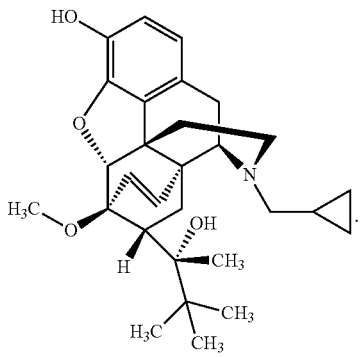

(98) The product of any one of the above (92) to (97), wherein the product comprises about 0.10 wt % or less of a compound of formula (13):

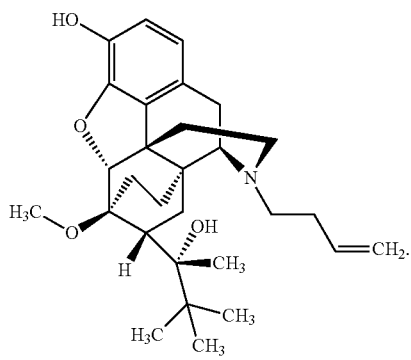

(99) The product of any one of the above (92) to (98), wherein the product comprises about 0.10 wt % or less of a compound of formula (15):

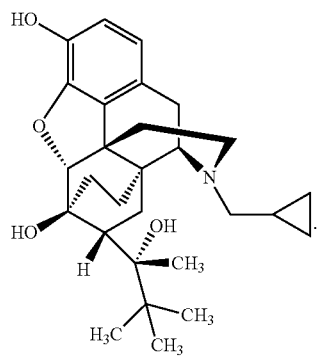

(100) A pharmaceutical composition comprising the product of any one of the above (92) to (99) and a pharmaceutically acceptable carrier.

(101) A method for treating pain, constipation, drug abuse, an addictive disorder, vomiting, respiratory depression, or euphoria comprising administering to an animal in need thereof an effective amount of the product of any one of the above (92) to (99) or a pharmaceutical composition of the above (100).

(102) A method for treating pain comprising administering to an animal in need thereof an effective amount of the product of any one of the above (92) to (99) or a pharmaceutical composition of the above (100).

(103) A method for preparing buprenorphine free base, comprising treating an acetate salt of buprenorphine at a pressure, temperature and for a time sufficient to remove the acetic acid.

(104) The method of the above (103), wherein the pressure is a sub-atmospheric pressure of from about 100 Torr to about 200 Torr.

(105) The method of the above (104), wherein the temperature is at least about 30° C. and the time is at least about 1 hour.

(106) The method of the above (105), wherein the temperature is at least about 50° C.

(107) The method of the above (105), wherein the temperature is at least about 65° C.

(108) The method of any one of the above (103) to (107), wherein the treatment lasts at least about 5 hours.

(109) The method of the above (108), wherein the treatment is lasts at least about 10 hours.

(110) The method of any one of the above (103) to (109), further comprising slurrying the buprenorphine free base with a slurrying solution comprising water and an alcohol, and filtering the free base therefrom.

(111) The method of the above (103), wherein the pressure is an atmospheric pressure of from about 620 Torr to about 780 Torr.

(112) The method of the above (111), wherein the temperature is from about 65° C. to about 100° C.

(113) The method of the above (111) or (112), wherein the treatment lasts at least about 7 hours.

(114) The method of any one of the above (111) to (113), wherein the treatment lasts long enough to form essentially pure buprenorphine free base.

(115) The method of any one of the above (103) to (114), wherein acetic acid in the final buprenorphine free base product is present at less than about 0.5 wt %.

(116) A buprenorphine free base product obtained from the method of any one of the above (103) to (115).

(117) A pharmaceutical composition comprising the product of the above (116) and a pharmaceutically acceptable carrier.

(118) A method for treating pain, constipation, drug abuse, an addictive disorder, vomiting, respiratory depression, or euphoria comprising administering to an animal in need thereof an effective amount of the product of the above (116) or the pharmaceutical composition of the above (117).

(119) A method for treating pain comprising administering to an animal in need thereof an effective amount of the product of the above (116) or the pharmaceutical composition of the above (117).

(120) A method for preparing buprenorphine free base, comprising the steps of:

(a) dissolving an acetate salt of buprenorphine in a solution to form an admixture;

(b) optionally filtering the admixture of step (a);

(c) adding a basic material to the admixture in step (a) or (b) to form a second admixture;

(d) adding an anti-solvent to the second admixture produced in step (c) to form a precipitate of the buprenorphine free base; and (e) isolating the precipitate from step (d).

(121) The method of the above (120), wherein the solution of step (a) comprises an organic solvent.

(122) The method of the above (121), wherein the organic solvent comprises an alcohol.

(123) The method of the above (122), wherein the organic solvent comprises an alcohol selected from the group consisting of methanol, ethanol, and isopropyl alcohol.

(124) The method of any one of the above (120) to (123), wherein the anti-solvent of step (d) comprises an aqueous solution.

(125) The method of any one of the above (120) to (124), wherein the acetate salt of buprenorphine is contacted with at least about 3 mass equivalents of the solution relative to the starting mass of the acetate salt of buprenorphine in step (a).

(126) The method of any one of the above (120) to (125), further comprising mixing the admixture of step (a) at a temperature of about 20° C. to about 90° C. such that substantially all the acetate salt of buprenorphine is dissolved.

(127) The method of the above (126), wherein in step (a) the admixture is at a temperature of at least about 40° C.

(128) The method of the above (126), wherein in step (a) the admixture is at a temperature of at least about 50° C.

(129) The method of any one of the above (120) to (128), wherein the admixture of step (a) is filtered in step (b).

(130) The method of any one of the above (120) to (129), wherein in step (c), from about 1.0 molar equivalent to about 20 molar equivalents of base relative to the starting number of moles of acetate salt of buprenorphine in step (a) are added to the admixture produced in step (a) or (b).

(131) The method of any one of the above (120) to (130), wherein in step (d), at least about 3 mass equivalents of the anti-solvent relative to the starting mass of the acetate salt of buprenorphine in step (a) are added to the second admixture produced in step (c).

(132) The method of any one of the above (120) to (131), wherein the isolating in step (e) is accomplished by filtration.

(133) The method of any one of the above (120) to (132), further comprising slurrying the free base obtained from the isolation of step (c) with a slurrying solution comprising water and an alcohol, and filtering the free base therefrom.

(134) A buprenorphine free base product obtained from the method of any one of the above (120) to (133).

(135) The product of the above (134), wherein the product comprises about 0.10 wt % or less of a compound of formula (10):

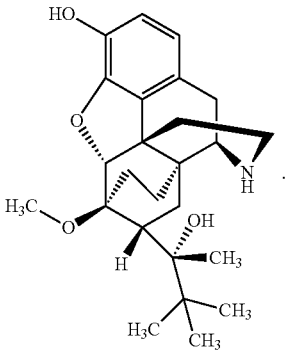

(136) The product of the above (134) or (135), wherein the product comprises about 0.10 wt % or less of a compound of formula (11):

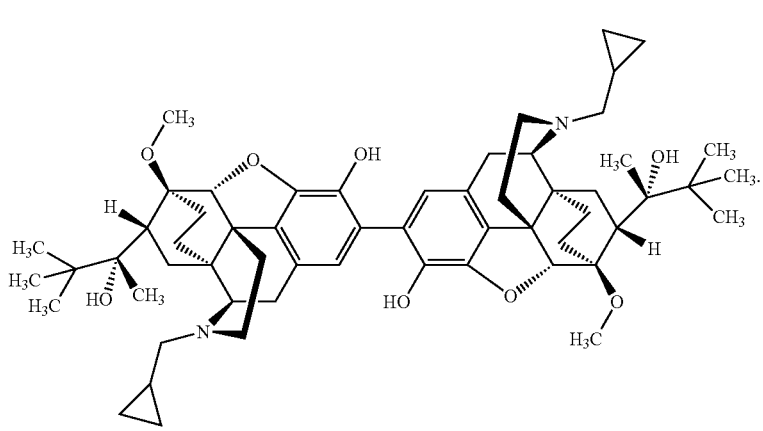

(137) The product of any one of the above (134) to (136), wherein the product comprises about 0.10 wt % or less of a compound of formula (12):

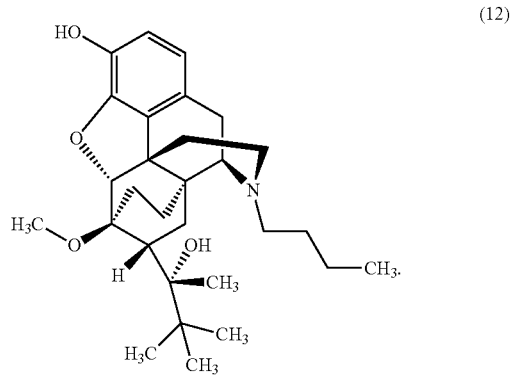

(138) The product of the above (137), wherein the product comprises about 0.08 wt % or less of the compound of formula (12).

(139) The product of any one of the above (134) to (138), wherein the product comprises about 0.10 wt % or less of a compound of formula (14):

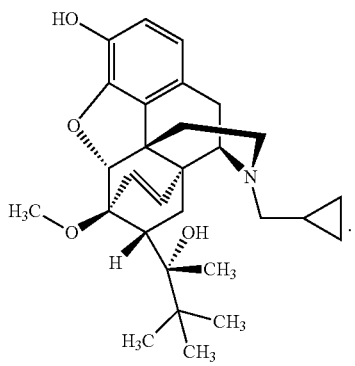

(14)

(140) The product of any one of the above (134) to (139), wherein the product comprises about 0.10 wt % or less of a compound of formula (13):

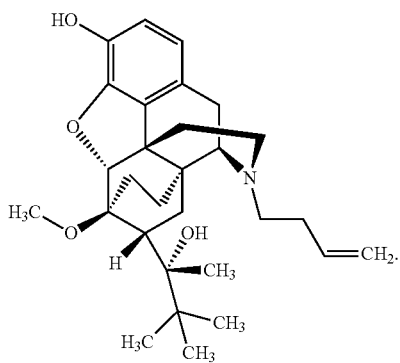

(13)

(141) The product of any one of the above (134) to (140), wherein the product comprises about 0.10 wt % or less of a compound of formula (15):

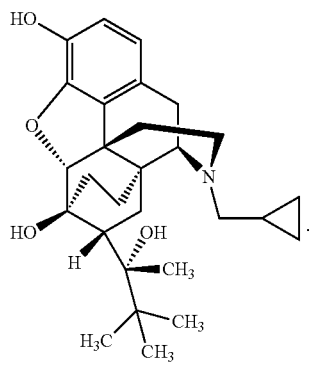

(15)

(142) A pharmaceutical composition comprising the product of any one of the above (134) to (141) and a pharmaceutically acceptable carrier.

(143) A method for treating pain, constipation, drug abuse, an addictive disorder, vomiting, respiratory depression, or euphoria comprising administering to an animal in need thereof an effective amount of the product of any one of the above (134) to (141) or the pharmaceutical composition of the above (142).

(144) A method for treating pain comprising administering to an animal in need thereof an effective amount of the product of any one of the above (134) to (131) or the pharmaceutical composition of the above (142).

(145) A method for preparing buprenorphine free base comprising:
(a) heating an admixture of an acetate salt of buprenorphine and an aqueous solution to provide precipitated buprenorphine free base; and
(b) filtering the admixture of step (a).

(146) The method of the above (145), wherein the aqueous solution consists essentially of water.

(147) The method of the above (145), wherein the aqueous solution comprises a mixture of water and an alcohol.

(148) The method of the above (147), wherein the alcohol is isopropyl alcohol.

(149) The method of any one of the above (145) to (148), wherein the heating is to a temperature of from about 70° C. to about 90° C.

(150) The method of the above (145) or (146), further comprising washing the solid filtered product of step (b) with a second aqueous solution.

(151) The method of any one of the above (145) to (150), further comprising the step of drying the solid filtered product of step (b).

(152) A buprenorphine free base product obtained from the method of any one of the above (145) to (151).

(153) A pharmaceutical composition comprising the product of the above (152) and a pharmaceutically acceptable carrier.

(154) A method for treating pain, constipation, drug abuse, an addictive disorder, vomiting, respiratory depression, or euphoria comprising administering to an animal in need thereof an effective amount of the product of the above (152) or the pharmaceutical composition of the above (153).

(155) A method for treating pain comprising administering to an animal in need thereof an effective amount of the product of the above (152) or the pharmaceutical composition of the above (153).

(156) A method for preparing buprenorphine free base: comprising:
(a) mixing an acetate salt of buprenorphine in a solvent to form an admixture;
(b) refluxing the admixture at a reflux temperature and removing the acetate as acetic acid in the vapor phase;
(c) cooling the admixture to provide precipitated buprenorphine free base; and
(d) isolating the buprenorphine free base.

(157) The method of the above (156), wherein the isolating of step (d) comprises filtering the precipitated buprenorphine free base of step (c).

(158) The method of the above (156) or (157), wherein the solvent comprises an organic solvent.

(159) The method of the above (158), wherein the organic solvent comprises heptane.

(160) A buprenorphine free base product obtained from the method of any one of the above (156) to (159).

(161) A pharmaceutical composition comprising the product of the above (160) and a pharmaceutically acceptable carrier.

(162) A method for treating pain, constipation, drug abuse, an addictive disorder, vomiting, respiratory depression, or euphoria comprising administering to an animal in need thereof an effective amount of the product of the above (160) or the pharmaceutical composition of the above (161).

(163) A method for treating pain comprising administering to an animal in need thereof an effective amount of the product of the above (160) or the pharmaceutical composition of the above (161).

4.1 Definitions

As used herein, the following terms are intended to have the following meanings.

"Crystalline form" as used herein refers to anhydrous crystalline forms, partially crystalline forms, a mixture of crystalline forms, hydrate crystalline forms, and solvate crystalline forms.

"Polymorphs," "polymorphic forms," and related terms as used herein refer to two or more crystal forms that consist essentially of the same molecule, molecules, and/or ions and include, but are not limited to, other solid state molecular forms such as hydrates and solvates. Different polymorphs can have different physical properties such as, e.g., melting temperature, heat of fusion, solubility, dissolution properties, and/or vibrational spectra, as a result of the arrangement or conformation of the molecules and/or ions in the crystal lattice. The differences in physical properties may affect pharmaceutical parameters such as storage stability, compressibility, and density (important in formulation and product manufacturing), and dissolution rate (an important factor in bioavailability).

"Solvate" as used herein refers to a crystalline form of a compound, molecule, atom, ion, or salt thereof that further contains molecules of a solvent incorporated into the crystalline structure. The solvent molecules in the solvate may be present in a regular arrangement or in a non-ordered arrangement. The solvate may comprise either a stoichiometric or non-stoichiometric amount of the solvent molecules. For example, a solvate with a non-stoichiometric amount of solvent molecules may result from partial loss of solvent from the solvate.

"Hydrate" as used herein refers to a crystalline form of a compound, molecule, atom, ion, or salt thereof further containing one or more water molecules in a three-dimensional arrangement. It can include non-stoichiometric hydrates or stoichiometric hydrates, such as a hemihydrate, monohydrate, dihydrate, trihydrate, tetrahydrate, pentahydrate, or hexahydrate, or a hydrate where the ratio of water per compound or salt thereof is not necessarily an integer but, for example, any value ranging from 0.5 to 10.0. In some embodiments, the hydrate has a ratio of water per compound or salt thereof of from 1 to 8. In some embodiments, the hydrate has a ratio of water per compound or salt thereof of from 1 to 5. In some embodiments, the hydrate has a ratio of water per compound or salt thereof of from 3 to 5, e.g., of 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

"Anhydrous," "anhydrate," and related terms refer to a compound, molecule, atom, ion, or salt with no water or that is substantially free of water. In some embodiments, "anhydrous" or "anhydrate" refers to a water content of less than about 1.0 wt % water by weight.

"Admixture" as used herein refers to the combined elements of the mixture regardless of the phase-state of the combination (e.g., entirely liquid or a slurry or, concurrently, liquid and solid).

"Seeding" as used herein refers to the addition of a crystalline material to an admixture, e.g., a solution, to initiate recrystallization or crystallization.

"Anti-solvent" as used herein refers to a solvent or liquid in which compounds are poorly soluble to insoluble. An anti-solvent may be used, for example, to cause a solubilized compound to precipitate out of solution. One example of an anti-solvent can be water (see Example 2).

In reference to a compound or composition, "purified" as used herein means the purity of a given compound. For example, a compound is "purified" when the given compound is a major component of the composition, i.e., at least 50 wt % of the preparation. Thus, "purified" embraces at least about 50 wt %, at least about 60 wt %, at least about 65 wt %, at least about 70 wt %, at least about 75 wt %, at least about 80 wt %, at least about 85 wt %, at least about 90 wt %, at least about 92 wt %, at least about 94 wt %, at least about 96 wt %, at least about 97 wt %, at least about 98 wt %, at least about 98.5 wt %, at least about 99.0 wt %, or at least about 99.5 wt % of a preparation being the compound of interest.

In reference to a compound or composition, "essentially pure" as used herein means at least 98 wt % of a preparation is the compound of interest. In some embodiments, a compound or composition is "essentially more pure" when at least 99 wt % of the preparation is the compound of interest.

In reference to a first compound or composition containing the first compound, "essentially free" of another compound as used herein means that the other compound is present in an amount that is no more than 1 wt % of the amount of the first compound of interest.

"Crystallizing," "crystallize," "crystallization," and related terms as used herein refer to a process of forming solid crystals precipitating from a solution, where "crystal" refers to a solid material, where the constituent compounds, salt, or solvates thereof are arranged in a regular pattern, which extends in all three spatial dimensions.

"Precipitating," "precipitate," "precipitation," and related terms as used herein encompasses "crystallizing," "crystallize," and "crystallization" unless stated otherwise. In some embodiments, the precipitate described herein is amorphous. In some embodiments, the precipitate is a mixture of amorphous and crystalline components. In some embodiments, the precipitate described herein is crystalline.

"Threshold amount," "threshold limit," and related terms as used herein refer to the reporting, identification, and acceptable limits of impurities, particularly organic impurities, in drug substances and dosage forms as set out in the latest version of the ICH Guidelines or by regulatory authorities, such as the U.S. Food and Drug Administration ("FDA") and the European Medicines Agency ("EMA"), and can be obtained from the latest version of the FDA or EMA monographs.

"Pharmaceutically acceptable" refers to those compounds, materials, compositions, and/or dosage forms which are, within the scope of sound medical judgment, suitable for administration to human beings or animals without excessive toxicity, irritation, allergic response, or other problem complications commensurate with a reasonable benefit/risk ratio.

"Salt" as used herein refers to a compound comprising at least one anion (e.g., an anion of acetic acid) and at least one cation (e.g., a buprenorphine cation resulting from protonation of buprenorphine free base by a Brönsted acid (e.g., phosphoric acid)). A salt may be the result of the neutralization reaction between an acid and a base (e.g., a Brönsted acid and a Brönsted base, or a Lewis acid and a Lewis base). In its solid form, the salt may form by precipitation or may have a crystalline structure. The term "salt" encompasses all salts of the disclosed compounds.

"Pharmaceutically acceptable salt" as used herein refers to any pharmaceutically acceptable salt that can be prepared from a compound or by a process of the disclosure, including a salt formed from an acid and a basic functional group, such as the nitrogen group of buprenorphine. Illustrative salts include, but are not limited, to sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also includes a salt prepared from a compound having an acidic functional group, such as a carboxylic acid functional group, and a pharmaceutically acceptable inorganic or organic base. Suitable bases include, but are not limited to, hydroxides of alkali metals such as sodium, potassium, cesium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; picoline; N-methyl-N-ethylamine; diethylamine; triethylamine; mono-, bis-, or tris-(2-hydroxy-($C_1$-$C_3$)alkyl amines), such as mono-, bis-, or tris-(2-hydroxyethyl)amine, 2-hydroxy-tert-butylamine, or tris-(hydroxymethyl)methylamine, N,N-di-[($C_1$-$C_3$)alkyl]-N-(hydroxy-($C_1$-$C_3$)alkyl)-amines, such as N,N-dimethyl-N-(2-hydroxyethyl)amine, or tri-(2-hydroxyethyl) amine; N-methyl-D-glucamine; and amino acids such as arginine, lysine, and the like.

In some embodiments, the pharmaceutically acceptable salt is a hydrochloride salt, a levulinic acid salt, a sulfate salt, an acetic acid salt, a sodium salt, a potassium salt, a benzene sulfonic acid salt, a para-toluenesulfonic acid salt, or a fumaric acid salt. In some embodiments, the pharmaceutically acceptable salt is a hydrochloride salt, a levulinic acid salt, an acetic acid salt, or a sulfate salt. In some embodiments, the pharmaceutically acceptable salt is a hydrochloride salt. In some embodiments, the pharmaceutically acceptable salt is a levulinic acid salt. In some embodiments, the pharmaceutically acceptable salt is an acetic acid salt. In some embodiments, the pharmaceutically acceptable salt is a sulfate salt. In some embodiments, the pharmaceutically acceptable salt is a sodium salt. In some embodiments, the pharmaceutically acceptable salt is a potassium salt. In some embodiments, the pharmaceutically acceptable salt is a pare-toluenesulfonic acid salt. Various pharmaceutically acceptable salts can be prepared by reaction of the compound with an appropriate acid according to the guidance in the present disclosure or by any of a variety of known methods in view of the present disclosure.

"Effective amount" as used herein in connection with a therapeutic agent refers to an amount of the agent or compound of the disclosure administered to an animal that provides a therapeutic effect.

"Treatment of," "treating," and related terms as used herein include the amelioration, reduction, slowing, or cessation of a Condition or a symptom thereof by administration of an effective amount of an agent or compound of the disclosure. In some embodiments, treating includes inhibiting, for example, decreasing the overall frequency of episodes of a Condition or a symptom thereof.

"Prevention of," "preventing," and related terms as used herein include the avoidance of the onset of a Condition or a symptom thereof by administration of an effective amount of an agent or compound of the disclosure.

"Disorder" as used herein includes, but is not limited to, the Conditions defined herein.

"Animal" as used herein includes, but is not limited to, a human or a non-human animal, such as a companion animal or livestock, e.g., a cow, monkey, baboon, chimpanzee, horse, sheep, pig, chicken, turkey, quail, cat, dog, mouse, rat, rabbit, or guinea pig. In one embodiment, an animal is a human.

The term "$C_{max}$" denotes the maximum plasma concentration obtained during a dosing interval.

The term "bioavailability" is defined for purposes of the disclosure as the relevant extent to which a drug (e.g., buprenorphine) is absorbed from a dosage form, e.g., a unit dosage form. Bioavailability is also referred to as "AUC" (i.e., the area under the plasma concentration versus time curve).

The term "molar equivalent" is defined for purposes of the disclosure as the number of moles of "X" relative to the number of moles of "Y". For example, 5 molar equivalents of X relative to Y signifies that if 1 mole of Y is used then 5 moles of X are used. One molar equivalent of X relative to Y signifies that if 1 mole of Y is used then 1 mole of X is used.

The term "mass equivalent" is defined for purposes of the disclosure as the mass amount of "X" relative to the mass amount of "Y". For example, 4 mass equivalents of X relative to Y signifies that if 1 g of Y is used then 4 g of X are used. One mass equivalent of X relative to Y signifies that if 1 kg of Y is used then 1 kg of X is used.

The articles "a," "an," and "the" as used herein refer to one or more than one of the species designated by the term following said article unless otherwise clearly indicated by context. For example, "a compound of formula (1)" encompasses one or more molecules of the compound of formula (1).

In the event of doubt as to the agreement of a depicted chemical structure and a chemical name, the chemical structure governs.

It is appreciated that various features of the disclosure which are, for clarity, described in the context of separate embodiments, can also be provided in combination in a single embodiment unless otherwise specifically excluded herein. Conversely, various features of the disclosure which are, for brevity, described in the context of a single embodiment, can also be provided separately and/or in any suitable subcombination unless otherwise specifically excluded herein.

4.2 Buprenorphine Acetate and Corresponding Hydrates

In some aspects, the disclosure provides new salts of buprenorphine. In particular, the new salts of the disclosure display superior properties and characteristics relative to other known salts of buprenorphine, e.g., as disclosed in Example 1 herein. In particular, the disclosure provides an acetate salt of buprenorphine. Buprenorphine, i.e., (4R,4aS,6R,7R,7aR,12bS)-3-(cyclopropylmethyl)-6-((S)-2-hydroxy-3,3-dimethylbutan-2-yl)-7-methoxy-1,2,3,4,5,6,7,7a-octahydro-4a,7-ethano-4,12-methanobenzofuro[3,2-e]isoquinolin-9-ol, has the chemical structure of formula (1):

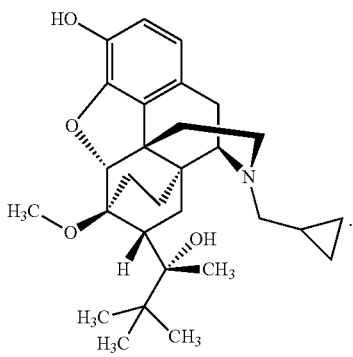

(1)

A mono-acetate salt of buprenorphine can be depicted as shown in formula (1a):

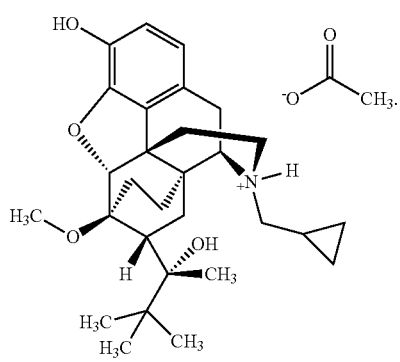

(1a)

In some embodiments, the disclosure provides polymorphs of the acetate salt of formula (1a). In some embodiments, a polymorph of the acetate salt of formula (1a) can be an anhydrate, a solvate, or a hydrate.

In some embodiments, acetate salts of buprenorphine are hydrates comprising from 1 to 6 water molecules per molecule of acetate salt. In some embodiments, each acetate salt of formula (1a) can be associated with 1, 2, 3, 4, 5, or 6 water molecules. In particular embodiments, each acetate salt of formula (1a) is associated with 4 water molecules and is referred to herein as a tetrahydrate, which can be depicted by formula (1b):

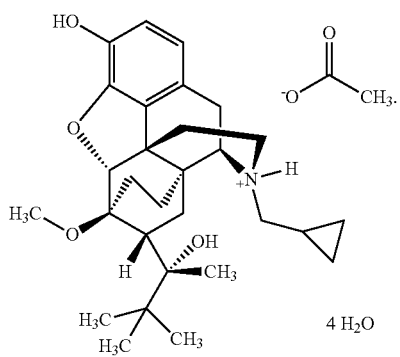

(1b)

In some embodiments, the stoichiometry of buprenorphine acetate salt molecules to water molecules is calculated as an average or mean value for a given sample. For example, for a given sample of buprenorphine acetate hydrate, the stoichiometry averages about 4 water molecules per buprenorphine acetate molecule. In some embodiments, the buprenorphine acetate hydrate has an average of about 3.5, about 3.6, about 3.7, about 3.8, about 3.9, about 4.0, about 4.1, about 4.2, about 4.3, about 4.4, or about 4.5 water molecules per buprenorphine acetate molecule.

In some embodiments, the buprenorphine acetate is in an anhydrous form. In some embodiments, the anhydrate of buprenorphine acetate is "substantially free" of water. A preparation substantially free of water can have an average stoichiometry of less than 0.40 molecules of water per molecule of buprenorphine acetate salt, such as about 0.30 water molecules or less, about 0.20 water molecules or less, about 0.10 water molecules or less, about 0.05 water molecules or less, about 0.02 water molecules or less, or about 0.01 water molecules or less. In some embodiments, the anhydrate of buprenorphine acetate that is substantially free of water has less than about 1.0 wt %, less than about 0.7 wt %, less than about 0.5 wt %, less than about 0.4 wt %, or less than about 0.2 wt % water by weight.

In some embodiments, the buprenorphine acetate salt is in the form of a purified buprenorphine acetate salt. In some embodiments, the purified buprenorphine acetate salt is at least about 50 wt %, at least about 60 wt %, at least about 65 wt %, at least about 70 wt %, at least about 75 wt %, at least about 80 wt %, at least about 85 wt %, at least about 90 wt %, at least about 92 wt %, at least about 94 wt %, at least about 96 wt %, or at least about 97 wt % of the weight of the preparation. In some embodiments, the buprenorphine acetate salt is in the form of an essentially pure buprenorphine acetate salt as defined herein, e.g., at least about 98 wt % or, in another embodiment, at least about 98.5 wt % of the weight of the preparation. In some embodiments, the buprenorphine acetate salt is in the form of an essentially more pure buprenorphine acetate salt as defined herein, e.g., at least about 99.0 wt % or, in another embodiment, at least about 99.5 wt % of the weight of the preparation.

In some embodiments, the buprenorphine acetate salt of the disclosure is a crystalline form of the buprenorphine acetate salt, such as a crystalline form of an anhydrate, hydrate, or solvate of the buprenorphine acetate salt. In some embodiments, the buprenorphine acetate salt is a crystalline form of a hydrate of buprenorphine acetate salt, where the hydrate can have the number of water molecules per molecule of acetate salt, such as 1, 2, 3, 4, 5, or 6 water molecules per molecule of acetate salt. In some embodiments, a crystalline form is the tetrahydrate depicted in formula (1b), shown above.

In some embodiments, the crystalline form of buprenorphine acetate salt is characterized by an X-ray powder diffraction ("XRPD") pattern obtained using CuKα radiation comprising one or more peaks at diffraction angles substantially equivalent to those in Table 1.

TABLE 1

| Position [°2Θ] | Relative Intensity [%] |
|---|---|
| 6.38 | 10 |
| 8.77 | 32 |
| 10.31 | 24 |
| 11.93 | 19 |
| 16.21 | 100 |
| 18.47 | 25 |
| 18.70 | 53 |
| 19.40 | 14 |

In some embodiments, the crystalline form of buprenorphine acetate salt is characterized by an XRPD pattern, obtained using CuKα radiation, comprising one or more peaks at 2θ angles substantially equivalent to 6.38, 8.77, 10.31, 11.93, 16.21, 18.47, 18.70, and 19.40. In some embodiments, the crystalline form of buprenorphine acetate salt is characterized by an XRPD pattern, obtained using CuKα radiation, comprising peaks at 2θ angles substantially equivalent to at least the peaks at 16.21 and 18.70, and having at least one additional peak at a 2θ angle substantially equivalent to at least one of the peaks at 8.77, 10.31, or 18.47. In some embodiments, the crystalline form of buprenorphine acetate salt is characterized by an XRPD pattern, obtained using CuKα radiation, comprising peaks at 2θ angles substantially equivalent to at least the peaks at 16.21 and 18.70, and having at least two additional peaks at 2θ angles substantially equivalent to at least two of the peaks at 8.77, 10.31, or 18.47. In some embodiments, the crystalline form of buprenorphine acetate salt is characterized by an XRPD pattern, obtained using CuKα radiation, comprising peaks at 2θ angles substantially equivalent to at least the peaks at 8.77, 10.31, 16.21, 18.47, and 18.70.

In some embodiments, the crystalline form of buprenorphine acetate salt is characterized by an XRPD pattern, obtained using CuKα radiation, comprising peaks at 2θ angles substantially equivalent to at least the peaks at 8.77, 10.31, 16.21, 18.47, and 18.70, and having at least one additional peak at a 2θ angle substantially equivalent to at least one of the peaks at 6.38, 11.93, or 19.40. In some embodiments, the crystalline form of buprenorphine acetate salt is characterized by an XRPD pattern, obtained using CuKα radiation, comprising peaks at 2θ angles substantially equivalent to at least the peaks at 8.77, 10.31, 16.21, 18.47, and 18.70, and having at least two additional peaks at a 2θ angle substantially equivalent to at least two of the peaks at 6.38, 11.93, or 19.40. In some embodiments, the crystalline form of buprenorphine acetate salt is characterized by an XRPD pattern, obtained using CuKα radiation, comprising peaks at 2θ angles substantially equivalent to at least the peaks at 6.38, 8.77, 10.31, 11.93, 16.21, 18.47, 18.70, and 19.40.

It will be appreciated that different equipment and/or conditions can result in slightly different XRPD data being generated. For example, there can be variations in the location and/or relative intensities of the peaks. Particularly, the intensities of XRPD peaks can vary as a result of particle size and shape because of the effects of the packing of the crystalline particles into XRPD mounts. Such packing effects are known in the art and are often referred to as the "preferred orientation" effect. Preferred orientation in samples influences the intensities of various XRPD peaks so that some are more intense and others are less intense, compared to that which would be expected from a completely random sample. XRPD intensity variations can occur because of differing particle size and shape. The art also recognizes that the position of XRPD peaks is affected by the precise height at which the sample sits in the diffractometer and the zero calibration of the diffractometer. The surface planarity of the sample can also have a small effect. Thus, the XRPD data presented are not to be taken as absolute values.

In some embodiments, the crystalline form of buprenorphine acetate salt is characterized by an XRPD pattern substantially the same as the XRPD pattern shown in FIG. 4, obtained using CuKα radiation. A first XRPD peak is considered to have the same °2θ angle as a second XRPD peak, i.e., be substantially equivalent to, if the first peak has a °2θ angle within ±0.2° of the second peak.

In some embodiments, the crystalline form of buprenorphine acetate salt is characterized by a differential scanning calorimetry ("DSC") transition profile. The DSC measures the heat flow from a sample as a function of temperature, with a typical heating rate (i.e., temperate change) of about 10° C./min. In some embodiments, the crystalline form of buprenorphine acetate salt is characterized by a transition with at least one peak position at from about 50° C. to about 180° C., or from about 50° C. to about 140° C., or from about 80° C. to about 130° C., or from about 90° C. to about 130° C., or from about 90° C. to about 120° C., or from about 95° C. to about 115° C., as measured by a heat flow differential scanning calorimeter at a heating rate of about 10° C. per minute.

In some embodiments, the crystalline form of the buprenorphine acetate salt is characterized by a transition having a peak position at from about 217° C. to about 225° C., or from about 218° C. to about 223° C., or from about 219° C. to about 223° C., as measured by a heat flow differential scanning calorimeter at a heating rate of about 10° C. per minute.

In some embodiments, the crystalline form of the buprenorphine acetate salt is characterized by a transition with at least one peak position at from about 50° C. to about 180° C., or from about 50° C. to about 140° C., or from about 80° C. to about 130° C., or from about 90° C. to about 130° C., or from about 90° C. to about 120° C., or from about 95° C. to about 115° C. and by another transition having a peak position at from about 210° C. to about 225° C., or from about 217° C. to about 225° C., or from about 218° C. to about 223° C., or from about 219° C. to about 223° C., as measured by a heat flow differential scanning calorimeter at a heating rate of about 10° C. per minute.

In some embodiments, the crystalline form of the buprenorphine acetate salt is characterized by a first transition region (Region 1) with at least one peak having a peak position at from about 50° C. to about 180° C., and a second transition region (Region 2) having a peak having a peak position at from about 210° C. to about 225° C., as discussed above and as measured by a heat flow differential scanning calorimeter at a heating rate of about 10° C. per minute.

Figure 5:
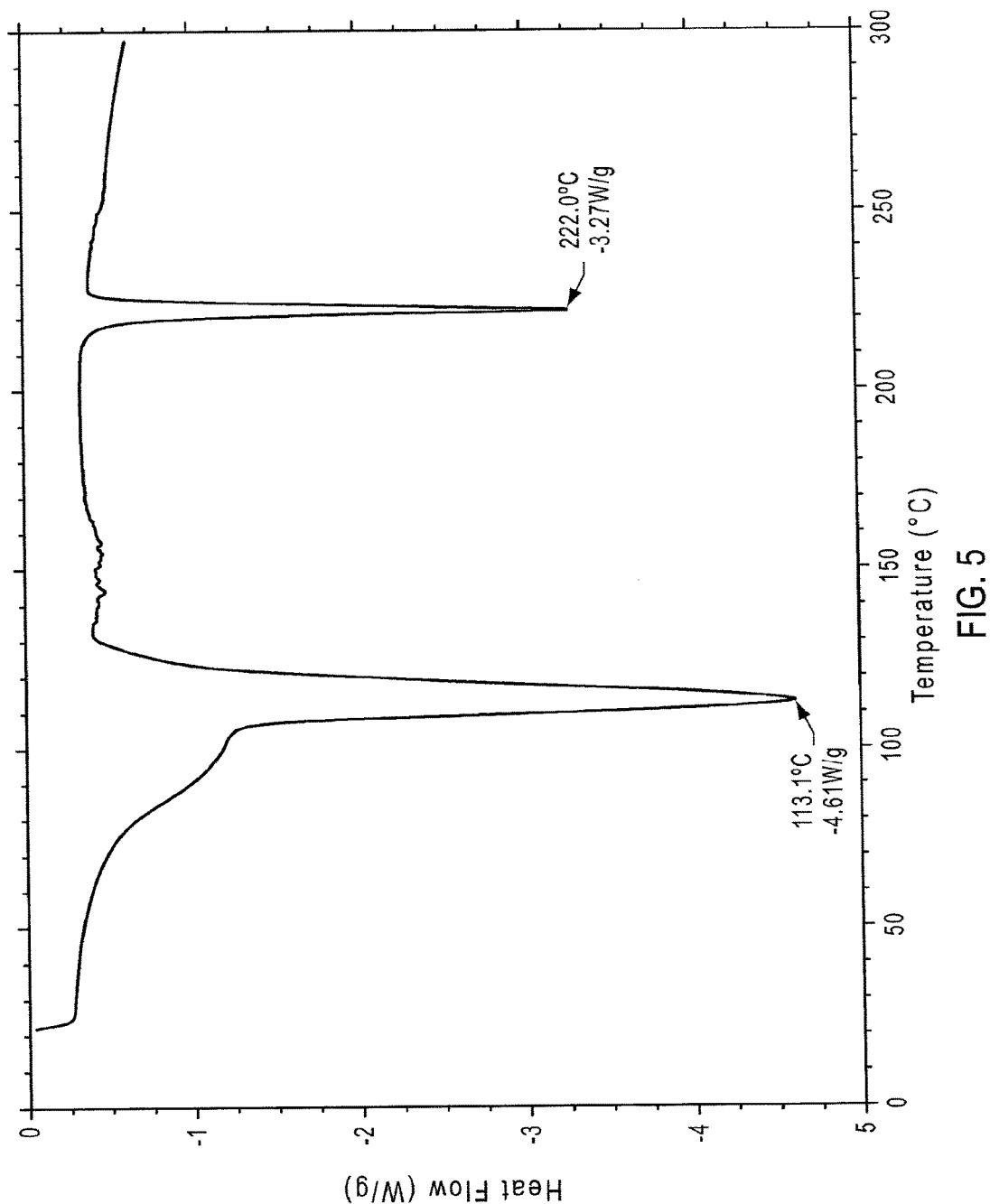
FIG. 5 shows a differential scanning calorimetry scan of buprenorphine acetate tetrahydrate at a heating rate of 10° C./min.

In some embodiments, the crystalline form of the buprenorphine acetate salt is characterized by a DSC profile substantially the same as the DSC profile shown in FIG. 5, when measured by a heat flow differential scanning calorimeter at a heating rate of about 10° C. per minute. In some embodiments, the crystalline form of the buprenorphine acetate salt is characterized by a DSC profile substantially the same as the DSC profile shown in FIG. 6, when measured by a heat flow differential scanning calorimeter at a heating rate of about 10° C. per minute.

In some embodiments, the crystalline form of the buprenorphine acetate is characterized by an integral (area under the curve) ratio of the first transition region (Region 1) over the second transition region (Region 2), i.e., Region 1/Region 2, of from about 7.0 to about 8.0. In some embodiments, the approximate integral ratio of Region 1/Region 2 for buprenorphine acetate is from about 7.1 to about 7.9. In some embodiments, the approximate integral ratio of Region 1/Region 2 for buprenorphine acetate is from about 7.1 to about 7.7. In some embodiments, the integral values for the transition regions are determined over the temperature range of from about 35° C. to about 180° C. for the first transition region (Region 1) and over the temperature range of from about 203° C. to about 233° C. for the second transition region (Region 2).

In some embodiments, the crystalline form of buprenorphine acetate salt is characterized by a water content of from about 11.1 wt % to about 13.0 wt %, or from about 11.5 wt % to about 12.6 wt %, or from about 11.8 wt % to about 12.5 wt %, or from about 12.0 wt % to about 12.3 wt %, as measured by Karl Fischer titration. In some embodiments, the crystalline form of buprenorphine acetate salt is characterized by a water content of about 12.3 wt %, about 12.25 wt %, or about 12.0 wt %. In some embodiments, the foregoing water content is for the buprenorphine acetate tetrahydrate, i.e., the compound of formula (1b).

In some embodiments, the crystalline form of buprenorphine acetate salt is characterized by one or more of the following:

(1) at least one of the XRPD peaks 20 shown in Table 1;
(2) an XRPD pattern substantially similar to FIG. 4;
(3) a DSC profile substantially similar to FIG. 5 or FIG. 6;
(4) a DSC integral ratio of transition Region 1/Region 2 of from about 7.0 to about 8.0; and
(5) a water content of from about 11.1 wt % to about 13.0 wt %.

In some embodiments, the crystalline form of buprenorphine acetate salt is characterized by two, three, four, or all of the features (1) to (5) above.

In some embodiments, the crystalline form of the buprenorphine acetate salt is characterized as a monoclinic crystal, such as described in the crystal characterization data presented in Table 4 herein below. In some embodiments, the crystalline form is characterized by monoclinic space group $P2_1$. In some embodiments, the crystalline form has unit cell parameters of a=10.5±0.5 Å, b=10.9±0.5 Å, and c=14.4±0.5 Å. In some embodiments, the crystalline form has unit cell parameters of a=10.52±0.05 Å, b=10.92±0.05 Å, and c=14.44±0.05 Å. In some embodiments, the crystalline form of the buprenorphine acetate salt is a monoclinic crystal of space group $P2_1$ having unit cell parameters of a=10.5±0.5 Å, b=10.9±0.5 Å, and c=14.4±0.5 Å. In some embodiments, the crystalline form of the buprenorphine acetate salt is a monoclinic crystal of space group $P2_1$ having unit cell parameters of a=10.52±0.05 Å, b=10.92±0.05 Å, and c=14.44±0.05 Å.

In some embodiments, the crystalline form of buprenorphine acetate has the same or equivalent fractional atomic coordinates ($\times 10^4$) and equivalent isotropic displacement parameters ($Å^2 \times 10^3$) set forth in Table 5.

In some embodiments, the buprenorphine acetate and its polymorphic forms exhibit high stability. In some embodiments, the buprenorphine acetate and its polymorphic forms retain about 95.0 area % or greater purity, about 96.0 area % or greater purity, about 97.0 area % or greater purity, about 98.0 area % or greater purity, about 98.5 area % or greater purity, about 99.0 area % or greater purity, about 99.1 area % or greater purity, about 99.2 area % or greater purity, about 99.3 area % or greater purity, about 99.4 area % or greater purity, about 99.5 area % or greater purity, about 99.6 area % or greater purity, about 99.7 area % or greater purity, about 99.8 area % or greater purity, or about 99.9 area % or greater purity under long term stability conditions (i.e., 25° C. at 65% relative humidity). In some embodiments, the buprenorphine acetate and its polymorphic forms retain about 95.0 area % or greater purity, about 96.0 area % or greater purity, about 97.0 area % or greater purity, about 98.0 area % or greater purity, about 98.5 area % or greater purity, about 99.0 area % or greater purity, about 99.1 area % or greater purity, about 99.2 area % or greater purity, about 99.3 area % or greater purity, about 99.4 area % or greater purity, about 99.5 area % or greater purity, about 99.6 area % or greater purity, about 99.7 area % or greater purity, about 99.8 area % or greater purity, or about 99.9 area % or greater purity under accelerated stability conditions (i.e., 40° C. at 75% relative humidity) (See Example 7 below for the method of determining the area % impurity under stability testing conditions). Generally, to be considered as unaffected by moisture, the ICH Guidelines and US Pharmacopeia and EMA Monographs require that a drug compound should be stable under the accelerated storage condition of 40° C.±2° C. at 75% RH±5% ("RH"=relative humidity) for a minimum time period of 6 months and stable under long term (i.e., for a minimum time period of 12 months) storage conditions of 25° C.±2° C. at 60% RH±5% or 30° C.±2° C. at 65% RH±5%.

In some embodiments, buprenorphine acetate and its polymorphic forms exhibit high photostability. In some embodiments, the buprenorphine acetate and its polymorphic forms retain about 99.0 area % or greater purity, about 99.1 area % or greater purity, about 99.2 area % or greater purity, about 99.3 area % or greater purity, about 99.4 area % or greater purity, about 99.5 area % or greater purity, about 99.6 area % or greater purity, about 99.7 area % or greater purity, about 99.8 area % or greater purity, or about 99.9 area % or greater purity when exposed to continuous UV light, e.g., UV light from a TL 20W/12RS UV bulb (Philips Lighting) at 21.9 W/m², for up to 3 months. In some embodiments, the buprenorphine acetate and its polymorphic forms retain about 99.0 area % or greater purity, about 99.1 area % or greater purity, about 99.2 area % or greater purity, about 99.3 area % or greater purity, about 99.4 area % or greater purity, about 99.5 area % or greater purity, about 99.6 area % or greater purity, about 99.7 area % or greater purity, about 99.8 area % or greater purity, or about 99.9 area % or greater purity when exposed to visible light, e.g., visible light from a F24T12/CW/HO fluorescent bulb (Philips Lighting) at 27 K lux for up to 3 months.

It has been discovered that the identity of the impurities present in, or absent from, the buprenorphine acetate of the disclosure are the same as the identity of the impurities present in, or absent from, the buprenorphine free base prepared from that buprenorphine acetate. For example, if a compound of formula (12) (see Section 4.3) is present in the buprenorphine acetate of the disclosure while a compound of formula (18) (see Section 4.3) is absent therefrom, then the compound of formula (12) will be present in the buprenorphine free base prepared from that buprenorphine acetate while the compound of formula (18) will be absent therefrom. It has also been discovered that the quantity of each impurity present in the buprenorphine acetate of the disclosure is about the same as the quantity of that impurity present in the buprenorphine free base prepared from that buprenorphine acetate. For example, if 0.080% of the compound of formula (12) is present in the buprenorphine acetate of the disclosure, then about 0.080% (±20%, i.e., from about 0.064% to about 0.096%) of the compound of formula (12) will be present in the buprenorphine free base prepared from that buprenorphine acetate. Thus, characterization of the identity and quantity of an impurity or impurities in the buprenorphine acetate of the disclosure also generally provides the impurity characterization for the buprenorphine free base prepared from that buprenorphine acetate, and vice versa.

4.3 Methods for Preparing Buprenorphine Acetate Salt, and Buprenorphine Acetate Made by the Methods In another aspect, the disclosure provides methods for preparing highly pure buprenorphine acetate. In a surprising discovery of the disclosure, the acetate salt of buprenorphine, prepared in the procedures described herein below, provides an intermediate through which very high purity buprenorphine can be attained under relatively mild conditions with very high yields, the buprenorphine being substantially free of impurities. In some embodiments, the buprenorphine acetate is essentially pure. In some embodiments, the buprenorphine acetate is essentially more pure. In some embodiments, the buprenorphine acetate is essentially free of impurities. In some embodiments, a method for preparing the acetate salt of buprenorphine comprises the steps of:

(a) contacting buprenorphine free base with a solution comprising acetic acid in a dissolution vessel to form an admixture, where the admixture is at a temperature of from about 40° C. to about 80° C.;

(b) optionally filtering the admixture of step (a);

(c) adding an agent to the admixture produced in step (a) or (b) to precipitate the acetate salt of buprenorphine; and (d) isolating the acetate salt of buprenorphine precipitated in step (c).

In some embodiments, in step (a) of the method the buprenorphine free base is contacted with from about 2.0 mass equivalents to about 6.0 mass equivalents, or from about 3.0 mass equivalents to about 5.0 mass equivalents, or from about 3.5 mass equivalents to about 4.5 mass equivalents of the acetic acid solution relative to the starting mass of the buprenorphine free base.

In some embodiments, the acetic acid solution used in step (a) is an aqueous acetic acid solution. The aqueous acetic acid solution contains at least a sufficient concentration of acetic acid to form, stoichiometrically, the acetate salt of all of the buprenorphine free base starting material. In some embodiments, the acetic acid in the aqueous solution is present at from about 40 wt % to about 70 wt %, or from about 45 wt % to about 60 wt %, or from about 45 wt % to about 55 wt %, or from about 47 wt % to about 55 wt %, or from about 49 wt % to about 53 wt % relative to the weight of the aqueous solution.

In some embodiments, in step (a) of the method the acetic acid solution supplied to the dissolution vessel is at a temperature of from about 40° C. to about 80° C., or from about 45° C. to about 75° C., or from about 50° C. to about 70° C., or from about 55° C. to about 65° C. In some embodiments, in step (a) of the method the acetic acid solution is an aqueous acetic acid solution and is at a temperature of from about 40° C. to about 80° C., or from about 45° C. to about 75° C., or from about 50° C. to about 70° C., or from about 55° C. to about 65° C. when supplied to the dissolution vessel.

In some embodiments, in step (a) of the method the admixture is at a temperature of from about 40° C. to about 80° C., or from about 45° C. to about 75° C., or from about 50° C. to about 70° C., or from about 55° C. to about 65° C. for a period of time such that at least a substantial portion of the buprenorphine free base has dissolved. In some embodiments, the admixture is heated to a temperature in the specified temperature range, or in some embodiments, the solution at a temperature in the specified temperature range is added to the buprenorphine free base to prepare the admixture. In reference to a substantial portion of the buprenorphine free base having dissolved, in one embodiment a substantial portion of the buprenorphine free base has dissolved when at least about 30 wt % of the buprenorphine free base has dissolved. In other embodiments, a substantial portion of the buprenorphine free base has dissolved when at least about 50 wt %, at least about 60 wt %, or at least about 75 wt % of the buprenorphine free base has dissolved. The quantity corresponding to "substantial portion of the buprenorphine free base has dissolved" can be determined from the yield of the resulting buprenorphine acetate salt as follows: if the determined yield of buprenorphine acetate salt remains relatively constant (within 5%) upon addition of an even greater quantity of buprenorphine free base then a substantial portion of the buprenorphine free base had dissolved before the addition of the even greater quantity of buprenorphine free base.

In some embodiments, the admixture of step (a) is agitated to accelerate dissolution of the buprenorphine free base. Agitation of the admixture can be achieved by a variety of techniques, including stirring, sonication, or shaking.

In some embodiments, the admixture of step (a) can optionally be filtered according to step (b) by using, e.g., a filtration apparatus. The filtration can be done with a filtration apparatus at suitable temperatures, including at a temperature of from about 40° C. to about 80° C., or from about 45° C. to about 75° C., or from about 50° C. to about 70° C., or from about 55° C. to about 65° C. In some embodiments, in step (b) the admixture of step (a) added to the filtration apparatus is at a temperature of from about 40° C. to about 80° C. or at a temperature of from about 45° C. to about 75° C. In some embodiments, an additional volume of an acetic acid solution is used to rinse the dissolution vessel and the filtration apparatus. This additional volume of the acetic acid solution can be from about 0.1 mass equivalents to about 2.0 mass equivalents, or from about 0.1 mass equivalents to about 1.1 mass equivalents, or from about 0.2 mass equivalents to about 1.5 mass equivalents, or from about 0.5 mass equivalents to about 1.1 mass equivalents, or from about 0.5 mass equivalents to about 1.0 mass equivalent, or from about 0.3 mass equivalents to about 0.5 mass equivalents relative to the starting mass of free base in step (a).

In some embodiments, the additional volume of the acetic acid solution is an aqueous acetic acid solution. In some embodiments, the aqueous solution of acetic acid can have an amount of acetic acid of from about 40 wt % to about 70 wt %, or from about 45 wt % to about 60 wt %, or from about 45 wt % to about 55 wt %, or from about 47 wt % to about 55 wt %, or from about 49 wt % to about 53 wt % relative to the weight of the aqueous solution.

In some embodiments, in step (c) of any of the preceding methods and variations thereof the agent of step (c) is selected from an anti-solvent, a seed crystal, and combinations thereof.

In some embodiments, the agent of step (c) comprises an anti-solvent. Any anti-solvent suitable for initiating precipitation of the acetate salt of buprenorphine and achieving the product with a desired characteristic, e.g., a reduced product impurity level, can be used. In some embodiments, the anti-solvent comprises water. In some embodiments, from about 0.2 mass equivalents to about 8.0 mass equivalents, or from about 0.5 mass equivalents to about 4.0 mass equivalents, or from about 0.5 mass equivalents to about 2.0 mass equivalents, or from about 0.5 mass equivalents to about 1.0 mass equivalent, or from about 0.6 mass equivalents to about 0.9 mass equivalents, or from about 0.7 mass equivalents to about 0.8 mass equivalents of anti-solvent relative to the starting mass of free base in step (a) are added to the admixture of step (a) or (b). Generally, the anti-solvent is added at a temperature sufficient to achieve the precipitation of the acetate salt of buprenorphine. In some embodiments, the anti-solvent is added at within about 10° C. or within about 5° C. of the temperature of the admixture of step (a) or step (b) above, particularly at from about 45° C. to about 75° C., or from about 50° C. to about 70° C., or from about 50° C. to about 65° C., or from about 55° C. to about 65° C.

In some embodiments, the anti-solvent is added over a period of from about 0.5 hours to about 3.0 hours, or from about 0.5 hours to about 2.5 hours, or from about 1.0 hours to about 2.0 hours.

In some embodiments, the anti-solvent is added in a single portion. In other embodiments, the anti-solvent is added in a plurality of portions, i.e., portion-wise. For example, the anti-solvent can be added in 2, 3, 4, 5, 6, 7, 8, 9, 10, or more distinct portions throughout step (c). The individual quantities of the anti-solvent in each portion can be the same or different. Portions of the anti-solvent can be added at well-defined intervals during step (c). For example, individual portions of the anti-solvent can be added about every 0.1 hour to 4.0 hours, or about every 0.5 hours as step (c) progresses. Alternatively, individual portions of the anti-solvent can be added at times during step (c) when the rate of formation of the buprenorphine acetate salt decreases.

In other embodiments, the anti-solvent is added continuously during step (c). In another embodiment, continuous addition is achieved by slowly dropping the anti-solvent from an addition funnel into the admixture. In another embodiment, continuous addition is achieved by filling a hypodermic syringe equipped with a mechanically-driven plunger with the anti-solvent and adding the anti-solvent through a hypodermic needle into the admixture. In another embodiment, continuous addition is achieved by adding the anti-solvent into the admixture with a mechanical pump.

Methods for carrying out portion-wise and continuous addition of an anti-solvent are known in the art. For example, U.S. Pat. Nos. 2,191,786, 2,583,420, 3,355,486, 3,749,646, 4,217,787, 6,486,692, and 6,994,827, hereby incorporated by reference, disclose vessels in which one reagent is added incrementally to an admixture. Incremental addition is known in the art as the metering-in over a finite period of time, in contrast with the addition of the total anti-solvent into the vessel at once. The term incremental addition includes addition using a continuous stream, addition using a variable stream, addition intermittently using separate portions, and other related methods. See U.S. Pat. No. 4,217,287 (col. 2, lines 56-62).

In some embodiments, the agent of step (c) comprises a seed crystal. In particular, the seed crystal comprises buprenorphine acetate salt. The seed crystal can be added in a sufficient amount to initiate precipitation of the buprenorphine acetate salt from solution in the admixture. In some embodiments, from about 0.1 wt % to about 10 wt %, or from about 0.1 wt % to about 9 wt %, or from about 0.1 wt % to about 8 wt %, or from about 0.1 wt % to about 7 wt %, or from about 0.1 wt % to about 6 wt %, or from about 0.1 wt % to about 5 wt %, or from about 0.1 wt % to about 4 wt %, or from about 0.1 wt % to about 3 wt %, or from about 0.1 wt % to about 2 wt %, or from about 0.1 wt % to about 1 wt %, or from about 0.2 wt % to about 0.8 wt %, or from about 0.3 wt % to about 0.7 wt %, or from about 0.4 wt % to about 0.6 wt %, or from about 0.2 wt % to about 0.5 wt % of seed crystal is added to the admixture of step (a) or (b) relative to the starting mass of free base in step (a). In some embodiments, from about 0.2 wt % to about 9 wt %, or from about 0.5 wt % to about 9 wt %, or from about 1 wt % to about 5 wt %, or from about 2 wt % to about 4 wt % of seed crystal is added to the admixture of step (a) or (b) relative to the starting mass of free base in step (a).

In some embodiments, the seed crystal is added at a suitable temperature that initiates precipitation of the acetate salt. In some embodiments, the admixture of step (a) or (b) is at a temperature of from about 40° C. to about 80° C., or from about 45° C. to about 75° C., or from about 50° C. to about 70° C., or from about 50° C. to about 65° C., or from about 53° C. to about 63° C., or from about 56° C. to about 63° C., or from about 58° C. to about 62° C., or from about 59° C. to about 61° C. when the seed crystal is added.

In some embodiments, in step (c) the agent for precipitating the buprenorphine acetate salt comprises a combination of both an anti-solvent and a seed crystal. In some embodiments, a first amount of anti-solvent is added, before, after, or concurrently with the addition of a seed crystal. This may further optionally be followed by the addition of a second amount of anti-solvent. In some embodiments, the first amount of anti-solvent is from about 0.2 mass equivalents to about 2.0 mass equivalents, or from about 0.35 mass equivalents to about 0.80 mass equivalents, or from about 0.5 mass equivalents to about 1.0 mass equivalent, or from about 0.6 mass equivalents to about 0.9 mass equivalents, or from about 0.65 mass equivalents to about 0.75 mass equivalents relative to the starting mass of free base in step (a). In some embodiments, when a seed crystal is used in combination with an anti-solvent, from about 0.1 wt % to about 10 wt %, or from about 0.1 wt % to about 9 wt %, or from about 0.1 wt % to about 8 wt %, or from about 0.1 wt % to about 7 wt %, or from about 0.1 wt % to about 6 wt %, or from about 0.1 wt % to about 5 wt %, or from about 0.1 wt % to about 4 wt %, or from about 0.1 wt % to about 3 wt %, or from about 0.1 wt % to about 2 wt %, or from about 0.1 wt % to about 1 wt %, or from about 0.2 wt % to about 0.8 wt %, or from about 0.3 wt % to about 0.7 wt %, or from about 0.4 wt % to about 0.6 wt %, or from about 0.2 wt % to about 0.5 wt % of seed crystal is added relative to the starting mass of free base in step (a). In some embodiments, the second, optional amount of anti-solvent is from about 1.0 mass equivalent to about 8.0 mass equivalents, or from about 1.0 mass equivalent to about 6.5 mass equivalents, or from about 4.0 mass equivalents to about 6.5 mass equivalents, or from about 5.0 mass equivalents to about 6.5 mass equivalents, or from about 5.6 mass equivalents to about 6.1 mass equivalents, or from about 5.75 mass equivalents to about 6.00 mass equivalents, or from about 5.8 mass equivalents to about 6.0 mass equivalents relative to the starting mass of free base in step (a). In some embodiments, the temperature of the admixture during addition of the second, optional amount of anti-solvent is about the same as the temperature of the admixture in step (a). In some embodiments, the temperature of the admixture during addition of the second, optional amount of anti-solvent is different from the temperature of the admixture in step (a). In some embodiments, the temperature of the admixture during addition of the second, optional amount of anti-solvent is about the same as the temperature of the admixture during the addition of the first amount of anti-solvent. In some embodiments, the temperature of the admixture during addition of the second, optional amount of anti-solvent is different from the temperature of the admixture during the addition of the first amount of anti-solvent.

In some embodiments, when initiating precipitation with a seed crystal, the admixture can be held at the admixture's temperature when the seed was added for up to 48 hrs, up to 36 hrs, up to 24 hrs, up to 12 hrs, up to 6 hrs, up to 5 hrs, up to 4 hrs, up to 3 hrs, up to 2 hrs, up to 1 hr, or up to 0.5 hrs.

In some embodiments, for any of the preceding methods, the method can further comprise cooling the admixture of step (c), following addition of the agent and prior to isolating the acetate salt of buprenorphine in step (d), to a temperature of about 30° C. or lower, about 25° C. or lower, about 20° C. or lower, about 15° C. or lower, or about 10° C. or lower. In some embodiments, the solution is cooled to a temperature of from about 5° C. to about 30° C., or from about 5° C. to about 25° C., or from about 5° C. to about 20° C., or from about 10° C. to about 20° C.

In some embodiments, for any of the preceding methods, the method can further comprise adding a co-solvent to the admixture following the precipitation of step (c) but prior to the isolation in step (d). In some embodiments, any co-solvent that provides or enhances the desirable properties of the product, e.g., to reduce a product impurity level, or process, e.g., to reduce foaming, can be used. In some embodiments, the co-solvent is an alcohol, for example, selected from methanol, ethanol, isopropyl alcohol ("IPA"), and combinations thereof. In some embodiments, the co-solvent is IPA.

In some embodiments, the amount of co-solvent added is from about 0.6 mass equivalents to about 0.8 mass equivalents, or from about 0.75 mass equivalents to about 0.65 mass equivalents, or from about 0.73 mass equivalents to about 0.67 mass equivalents relative to the starting mass of free base in step (a). In some embodiments, the temperature of co-solvent being added is from about 50° C. to about 70° C., or from about 52° C. to about 68° C., or from about 55° C. to about 65° C.

In some embodiments, following the addition of co-solvent and prior to isolating the acetate salt of buprenorphine in step (d), the method can further comprise cooling the admixture to a temperature of about 30° C. or lower, about 25° C. or lower, about 20° C. or lower, about 15° C. or lower, or about 10° C. or lower. In some embodiments, the solution is cooled to a temperature of from about 5° C. to about 30° C., or from about 5° C. to about 25° C., or from about 5° C. to about 20° C., or from about 10° C. to about 20° C. In some embodiments, the cooling rate is from about 1° C./hr to about 20° C./hr, or from about 4° C./hr to about 15° C./hr, or from about 5° C./hr to about 12° C./hr, or from about 6° C./hr to about 10° C./hr.

Following the precipitation of the buprenorphine acetate salt in step (c), the method further comprises step (d) of isolating the buprenorphine acetate salt. In some embodiments, the isolation in step (d) is accomplished by filtration, centrifugation, trituration, or decantation.

In some embodiments, the method further comprises slurrying the buprenorphine acetate salt obtained from step (d) using a slurrying solution. In some embodiments, the slurrying solution comprises an alcohol, such as IPA, or water and alcohol, such as water and IPA. The slurry can be filtered to provide a preparation of buprenorphine acetate salt.

As discussed above, the buprenorphine acetate salt prepared by any of the methods described above, and polymorphic forms thereof, are essentially free of impurities, and thus in some embodiments, result in essentially pure buprenorphine acetate salt. Some impurities produced during the synthesis of buprenorphine have similar chemical properties to buprenorphine, which tends to make purification of the final product difficult. As noted above, it has been discovered that buprenorphine acetate salt, and in particular the buprenorphine acetate salt prepared by the methods disclosed herein, has a lower level of impurities, and in some embodiments, is essentially free of impurities. Without being bound by theory, it is believed that the reduction in impurities occurs during the precipitation of crystalline buprenorphine acetate salt; the undesirable impurities are believed to remain in solution in the admixture of step (c) after isolation of the buprenorphine acetate salt. Accordingly, in another aspect the disclosure provides buprenorphine acetate salts prepared by any of the methods described herein, and particularly the compound of formula (1b), each having an advantageously improved impurity profile.

In some embodiments, the buprenorphine acetate salt preparation of the disclosure, including the anhydrates, solvates, hydrates, and crystalline forms thereof, comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (10):

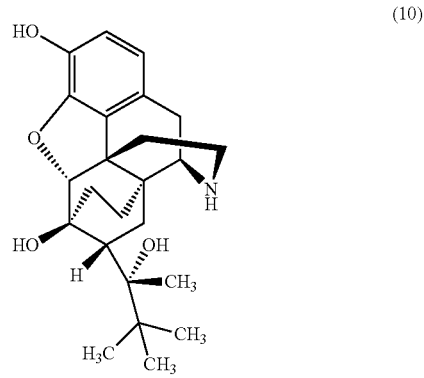

or a salt thereof.

In some embodiments, the buprenorphine acetate salt preparation of the disclosure, including the anhydrates, solvates, hydrates, and crystalline forms thereof, comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (11):

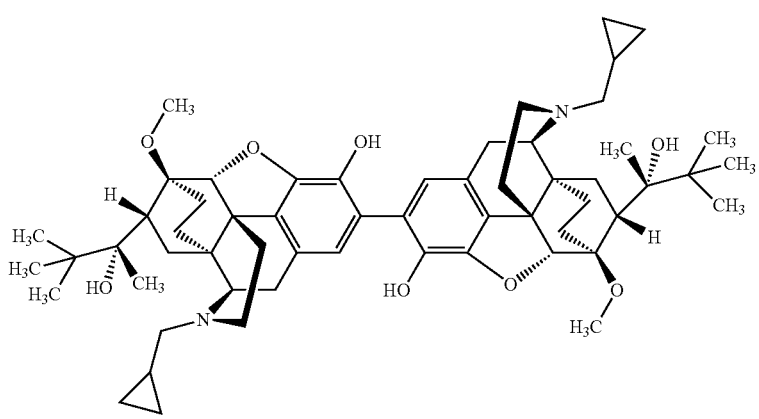

or a salt thereof.

In some embodiments, the buprenorphine acetate salt preparation of the disclosure, including the anhydrates, solvates, hydrates, and crystalline forms thereof, comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (12):

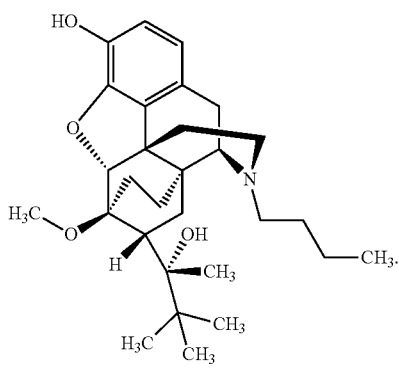

(12)

or a salt thereof.

In some embodiments, the buprenorphine acetate salt preparation of the disclosure, including the anhydrates, solvates, hydrates, and crystalline forms thereof, comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (13):

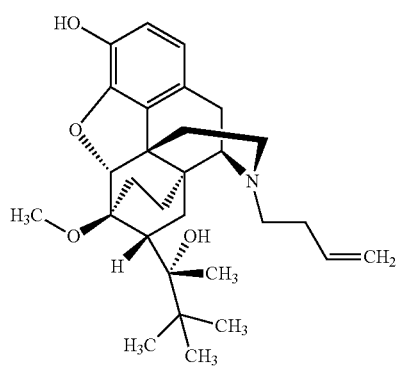

(13)

or a salt thereof.

In some embodiments, the buprenorphine acetate salt preparation of the disclosure, including the anhydrates, solvates, hydrates, and crystalline forms thereof, comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (14):

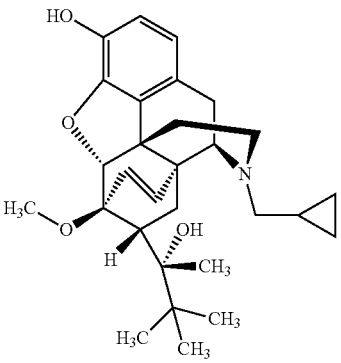

(14)

or a salt thereof.

In some embodiments, the buprenorphine acetate salt preparation of the disclosure, including the anhydrates, solvates, hydrates, and crystalline forms thereof, comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (15):

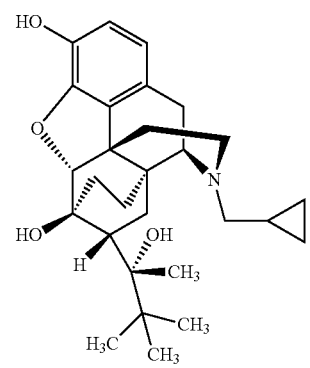

(15)

or a salt thereof.

In some embodiments, the buprenorphine acetate salt preparation of the disclosure, including the anhydrates, solvates, hydrates, and crystalline forms thereof, comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (16):

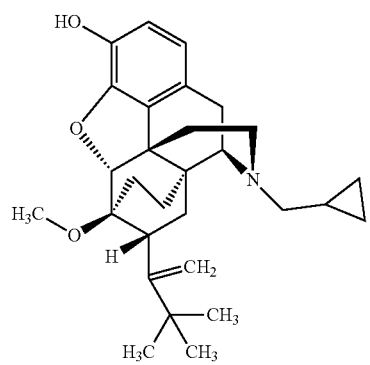

(16)

or a salt thereof.

In some embodiments, the buprenorphine acetate salt preparation of the disclosure, including the anhydrates, solvates, hydrates, and crystalline forms thereof, comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (17):

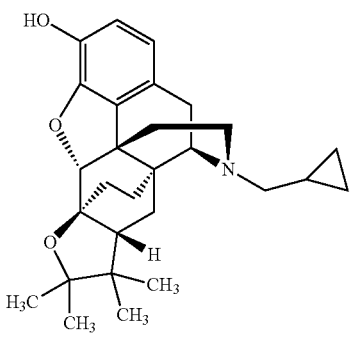

(17)

or a salt thereof.

In some embodiments, the buprenorphine acetate salt preparation of the disclosure, including the anhydrates, solvates, hydrates, and crystalline forms thereof, comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (18):

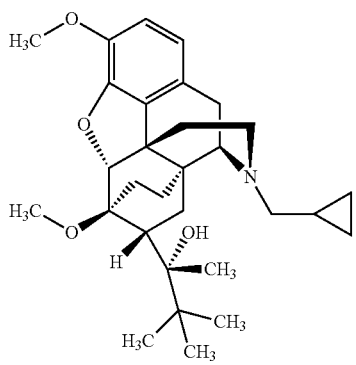

(18)

or a salt thereof.

In some embodiments, the buprenorphine acetate salt preparation of the disclosure, including the anhydrates, solvates, hydrates, and crystalline forms thereof, comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (19):

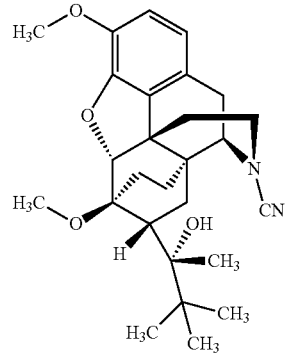

(19)

or a salt thereof.

In some embodiments, the buprenorphine acetate salt preparation of the disclosure, including the anhydrates, solvates, hydrates, and the crystalline forms thereof, is essentially free of impurities. In some embodiments, the total amount of impurities, including the combined level of impurities of the compounds of formulae (10), (11), (12), (13), (14), and (15), is about 0.70 wt % or less, about 0.65 wt % or less, about 0.60 wt % or less, about 0.55 wt % or less, about 0.50 wt % or less, about 0.45 wt % or less, about 0.40 wt % or less, about 0.35 wt % or less, about 0.30 wt % or less, about 0.25 wt % or less, about 0.20 wt % or less, about 0.15 wt % or less, or about 0.10 wt % or less.

In some embodiments, the buprenorphine acetate salt preparation of the disclosure, including the anhydrates, solvates, hydrates, and crystalline forms thereof, is essentially free of impurities. In some embodiments, the total amount of impurities, including the combined level of impurities of the compounds of formulae (10), (11), (12), (13), (14), (15), (16), (17), (18), and (19), is about 0.70 wt % or less, about 0.65 wt % or less, about 0.60 wt % or less, about 0.55 wt % or less, about 0.50 wt % or less, about 0.45 wt % or less, about 0.40 wt % or less, about 0.35 wt % or less, about 0.30 wt % or less, about 0.25 wt % or less, about 0.20 wt % or less, about 0.15 wt % or less, or about 0.10 wt % or less.

4.4 Buprenorphine Free Base, Buprenorphine Salts, and Methods for Preparing the Same As discussed above, the buprenorphine acetate salts, and the solvates, hydrates, anhydrates, and crystalline forms thereof, allow separation of impurities present in current preparations of buprenorphine, and thus provide a synthetic intermediate for preparing buprenorphine, including its free base and other salt forms, of increased purity. By using the methods of the disclosure, buprenorphine, including its free base, salt forms, solvates, hydrates, anhydrates, and crystalline forms can be prepared essentially free of impurities.

Accordingly, in a further aspect, the disclosure provides a method for preparing buprenorphine free base, the method comprising treating an acetate salt of buprenorphine under sufficient conditions to remove the acetic acid counterion, thereby providing the buprenorphine free base (and acetic acid). In some embodiments, the treatment step removes the acetate counterion sufficiently to yield an essentially pure buprenorphine free base. In some embodiments, the amount of acetate remaining in the buprenorphine free base preparation is less than about 0.10 wt %, less than about 0.09 wt %, less than about 0.08 wt %, less than about 0.07 wt %, less than about 0.06 wt %, or less than about 0.05 wt %.

A first method for preparing buprenorphine free base from an acetate salt of buprenorphine, e.g., from buprenorphine acetate tetrahydrate, comprises the steps of:

(a) contacting an acetate salt of buprenorphine with a solution and a basic material to form an admixture;

(b) agitating the admixture of step (a) at a temperature of from about 20° C. to about 90° C. to provide buprenorphine free base;

(c) isolating the buprenorphine free base of step (b); and (d) optionally repeating steps (a) through (c) one or more times.

In some embodiments of this first method for preparing buprenorphine free base from an acetate salt of buprenorphine, in step (a), the acetate salt of buprenorphine is contacted with at least about the same mass (i.e., about 1 mass equivalent) of the solution relative to the starting mass of acetate salt in step (a). In some embodiments, in step (a), the acetate salt of buprenorphine is contacted with from about 1.0 mass equivalent to about 6.0 mass equivalents, or from about 2.0 mass equivalents to about 5.0 mass equivalents, or from about 2.0 mass equivalents to about 4.0 mass equivalents, or from about 3.0 mass equivalents to about 4.0 mass equivalents of the solution relative to the starting mass of acetate salt in step (a). The acetate salt of buprenorphine dissolves at least partially in the solution; however, the buprenorphine free base is relatively insoluble therein and can precipitate. In some embodiments, the solution of step (a) comprises water and an alcohol. In some embodiments, the water and alcohol solution comprises from about 30 wt % to about 70 wt % alcohol in water, or from about 40 wt % to about 60 wt % alcohol in water, or from about 50 wt % to about 60 wt % alcohol in water. In some embodiments, the alcohol is selected from methanol, ethanol, IPA, and combinations thereof. In some embodiments, the alcohol is IPA. In some embodiments, the water and alcohol solution comprises from about 30 wt % to about 70 wt % IPA in water, or from about 40 wt % to about 60 wt % IPA in water, or from about 50 wt % to about 60 wt % IPA in water.

In some embodiments of this first method for preparing buprenorphine free base from an acetate salt of buprenorphine, the basic material used in step (a) can be any base suitable for preparing buprenorphine free base. In some embodiments, the basic material is selected from a hydroxide, carbonate, alkoxide, hydride, phosphate, borate (such as borax), oxide (such as CaO), cyanide (such as KCN), silicate (such as sodium metasilicate), amine (such as triethylamine, pyridine, or 4-dimethylaminopyridine), and the like, and combinations thereof. In some embodiments, the basic material comprises a hydroxide. In some embodiments, the basic material comprises ammonium hydroxide. In some embodiments, the basic material is aqueous ammonium hydroxide.

In some embodiments, the acetate salt of buprenorphine is contacted with from about 0.5 molar equivalents to about 20 molar equivalents, or from about 1 molar equivalent to about 20 molar equivalents, or from about 1 molar equivalent to about 10 molar equivalents, of basic material relative to starting moles of the acetate salt of buprenorphine in step (a).

In some embodiments, in step (b) agitating the admixture can be done by any appropriate method, such as by shaking, stirring, or sonicating the admixture. In some embodiments, in step (b), the admixture is agitated for a sufficient time to remove the acetic acid counterion. In some embodiments, the admixture of step (a) is agitated in step (b) from about 1 hr to about 36 hrs, or from about 1 hr to about 24 hrs, or from about 2 hrs to about 20 hrs, or from about 2 hrs to about 8 hrs, or from about 3 hrs to about 7 hrs, or from about 4 hrs to about 6 hrs. In some embodiments, in step (b) the admixture is agitated at a temperature of from about 25° C. to about 90° C., or from about 25° C. to about 60° C., or from about 30° C. to about 45° C.

In this first method for preparing buprenorphine free base from an acetate salt of buprenorphine, the free base formed in step (b) is isolated in step (c), for example, by precipitation. Any suitable methods for isolating the buprenorphine free base can be used. In some embodiments, the isolating in step (c) is accomplished by filtration or by centrifugation to obtain the isolated precipitate.

In some embodiments, the method for preparing buprenorphine free base from an acetate salt of buprenorphine optionally further comprises step (d), i.e., repeating steps (a) through (c) one or more times. In some embodiments of step (d), steps (a) through (c) are repeated once, twice, thrice, or at least thrice.

In some embodiments, the free base isolated in step (c) can be subsequently processed. Thus, in some embodiments, the method for preparing buprenorphine free base from an acetate salt of buprenorphine can further comprise a step of slurrying the isolated solid product of step (c) with a slurrying solution. In some embodiments, the slurrying solution comprises a water and alcohol mixture. In some embodiments, the slurrying solution comprises IPA in water, where the alcohol is present at from about 5 wt % to about 40 wt %, or from about 5 wt % to about 30 wt %, or from about 10 wt % to about 30 wt %. The free base can then be isolated from the slurry, such as by filtration or by centrifugation. In some embodiments, the slurrying temperature is from about 5° C. to about 40° C., or from about 10° C. to about 35° C., or from about 15° C. to about 35° C.

In some embodiments of this first method, acetic acid in the final free base preparation of buprenorphine is present at less than about 0.7 wt %, less than about 0.5 wt %, less than about 0.3 wt %, less than about 0.2 wt %, or less than about 0.1 wt % after the first method is carried out.

In another aspect, the disclosure provides the buprenorphine free base prepared by the first method, or by any variations thereof described above. In some embodiments, the buprenorphine free base prepared by the first method is essentially free of impurities.

In some embodiments, the buprenorphine free base prepared by the first method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (10):

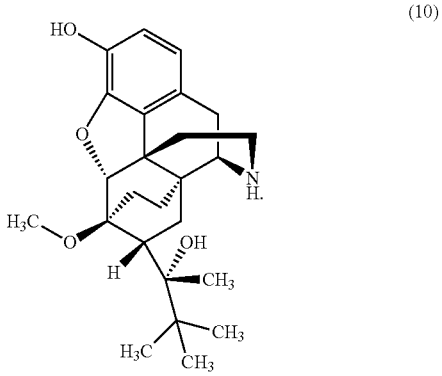

(10)

In some embodiments, the buprenorphine free base prepared by the first method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (11):

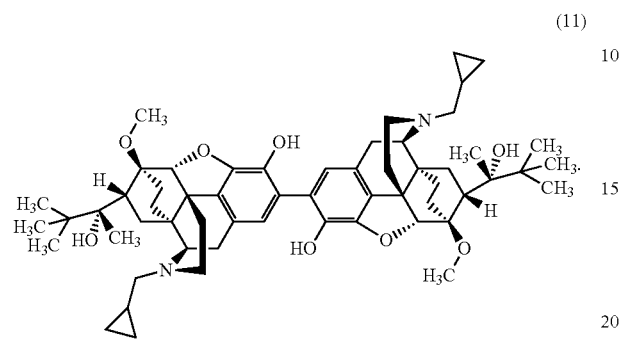

(11)

In some embodiments, the buprenorphine free base prepared by the first method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (12):

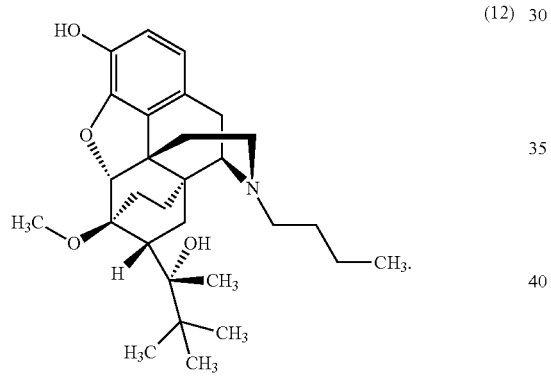

(12)

In some embodiments, the buprenorphine free base prepared by the first method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (13):

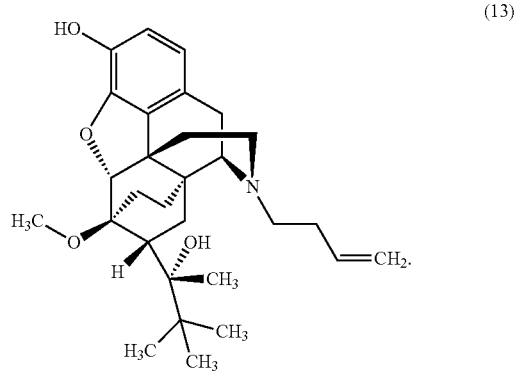

(13)

In some embodiments, the buprenorphine free base prepared by the first method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (14):

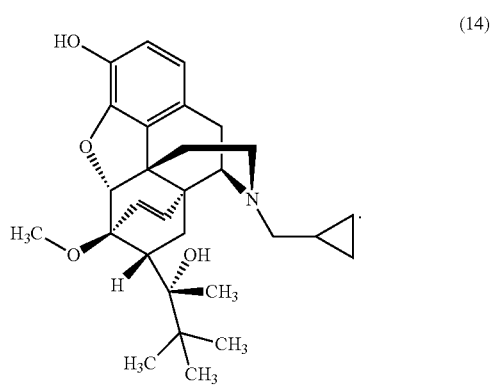

(14)

In some embodiments, the buprenorphine free base prepared by the first method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (15):

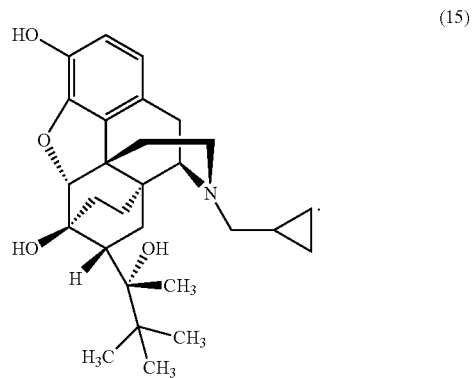

(15)

In some embodiments, for the free base preparation of buprenorphine prepared by the first method, the combined level of impurities of the compounds of formulae (10), (11), (12), (13), (14), and (15) is about 0.70 wt % or less, about 0.65 wt % or less, about 0.60 wt % or less, about 0.55 wt % or less, about 0.50 wt % or less, about 0.45 wt % or less, about 0.40 wt % or less, about 0.35 wt % or less, about 0.30 wt % or less, about 0.25 wt % or less, or about 0.20 wt % or less.

In some embodiments, for the free base preparation of buprenorphine prepared by the first method, the combined level of impurities of the compounds of formulae (10), (11), (12), (13), (14), and (15), and any other impurity or impurities not specifically identified herein, is about 0.75 wt % or less, about 0.70 wt % or less, about 0.65 wt % or less, about 0.60 wt % or less, about 0.55 wt % or less, about 0.50 wt % or less, about 0.45 wt % or less, about 0.40 wt % or less, about 0.35 wt % or less, about 0.30 wt % or less, about 0.25 wt % or less, or about 0.20 wt % or less.

Alternatively, the buprenorphine free base can be prepared from an acetate salt of buprenorphine by removing the acetic acid counterion by methods such as by heating, evaporating under about atmospheric pressure, evaporating under sub-atmospheric pressure, or any combination thereof.

Accordingly, a second method for preparing buprenorphine free base from an acetate salt of buprenorphine, e.g., from buprenorphine acetate tetrahydrate, comprises treating an acetate salt of buprenorphine at a pressure, temperature and for a time sufficient to remove the acetic acid and water, thereby providing the buprenorphine free base. In some embodiments, the treating is at a temperature of at least about 30° C. over a period of time sufficient to remove the acetic acid and water. In some embodiments, such treating is done for at least 1 hr.

In some embodiments of this second method, the acetate salt of buprenorphine is treated under sub-atmospheric pressure, for example, at a pressure of from about 50 Torr to about 250 Torr, or from about 75 Torr to about 225 Torr, or from about 100 Torr to about 200 Torr, or from about 125 Torr to about 175 Torr. In some embodiments, such treating is done at about 150 Torr.

In some embodiments of this second method, the acetate salt of buprenorphine is treated under about atmospheric pressure, for example, at a pressure of from about 620 Torr to about 780 Torr, or from about 670 Torr to about 780 Torr, or from about 700 Torr to about 780 Torr, or from about 740 Torr to about 780 Torr, or from about 750 Torr to about 770 Torr, or from about 755 Torr to about 765 Torr. In some embodiments, such treating is done at an atmospheric pressure of about 760 Torr.

In some embodiments of this second method for preparing buprenorphine free base from an acetate salt of buprenorphine, the acetate salt of buprenorphine is treated at a temperature of at least about 45° C., at least about 50° C., or at least about 65° C. In some embodiments of this second method for preparing buprenorphine free base from an acetate salt of buprenorphine, the treatment temperature is from about 50° C. to about 110° C., or from about 50° C. to about 105° C., or from about 60° C. to about 100° C., or from about 65° C. to about 100° C.

In some embodiments of this second method, the heating at the treatment temperature lasts for at least about 5 hrs, for at least about 6 hrs, for at least about 7 hrs, for at least about 9 hrs, for at least about 10 hrs, for at least about 12 hrs, or lasts long enough to form essentially pure buprenorphine free base.

In some embodiments, this second method for preparing buprenorphine free base from an acetate salt of buprenorphine further comprises slurrying the free base with a slurrying solution and filtering the solid free base therefrom. In some embodiments, the slurrying solution comprises water and an alcohol, as disclosed above for the first method.

In some embodiments of this second method, acetic acid in the final free base preparation of buprenorphine is present at less than about 0.7 wt %, less than about 0.5 wt %, less than about 0.3 wt %, less than about 0.2 wt %, or less than about 0.1 wt %.

In another aspect, the disclosure provides the buprenorphine free base prepared by the second method, or by any variations thereof described above. In some embodiments, the buprenorphine free base prepared by the second method is essentially free of impurities.

In some embodiments, the buprenorphine free base prepared by the second method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (10).

In some embodiments, the buprenorphine free base prepared by the second method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (11).

In some embodiments, the buprenorphine free base prepared by the second method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (12).

In some embodiments, the buprenorphine free base prepared by the second method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (13).

In some embodiments, the buprenorphine free base prepared by the second method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (14).

In some embodiments, the buprenorphine free base prepared by the second method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (15).

In some embodiments, for the buprenorphine free base prepared by the second method, the combined level of impurities of the compounds of formulae (10), (11), (12), (13), (14), and (15), is about 0.70 wt % or less, about 0.65 wt % or less, about 0.60 wt % or less, about 0.55 wt % or less, about 0.50 wt % or less, about 0.45 wt % or less, about 0.40 wt % or less, about 0.35 wt % or less, about 0.30 wt % or less, about 0.25 wt % or less, or about 0.20 wt % or less.

In some embodiments, for the buprenorphine free base prepared by the second method, the combined level of impurities of the compounds of formulae (10), (11), (12), (13), (14), and (15), and any other impurity or impurities not specifically identified herein, is about 0.75 wt % or less, about 0.70 wt % or less, about 0.65 wt % or less, about 0.60 wt % or less, about 0.55 wt % or less, about 0.50 wt % or less, about 0.45 wt % or less, about 0.40 wt % or less, about 0.35 wt % or less, about 0.30 wt % or less, about 0.25 wt % or less, or about 0.20 wt % or less.

A third method for preparing buprenorphine free base from an acetate salt of buprenorphine, e.g., from buprenorphine acetate tetrahydrate, comprises the steps of:

(a) dissolving an acetate salt of buprenorphine in a solution to form an admixture;

(b) optionally filtering the admixture of step (a);

(c) adding a basic material to the admixture in step (a) or (b) to form a second admixture;

(d) adding an anti-solvent to the second admixture produced in step (c) to form a precipitate of the buprenorphine free base; and (e) isolating the precipitate from step (d).

In some embodiments of this third method for preparing buprenorphine free base from an acetate salt of buprenorphine, the admixture of step (a) comprises an organic solvent. In some embodiments, the organic solvent comprises an alcohol. In some embodiments, the organic solvent comprises an alcohol selected from methanol, ethanol and isopropyl alcohol. In some embodiments, the alcohol is selected from methanol, ethanol and isopropyl alcohol. In some embodiments, the alcohol is IPA. In some embodiments, the acetate salt of buprenorphine is contacted with at least about 3.0 mass equivalents of the solution relative to the starting mass of the acetate salt of buprenorphine in step (a).

In some embodiments of this third method, in step (a) the admixture is at a temperature of about 20° C. to about 90° C. In some embodiments, in step (a) the admixture is at a temperature of at least about 20° C., at least about 40° C., at least about 50° C., at least about 55° C., or at least about 60° C. The admixture can be at a temperature in the specified temperature range by various methods, such as by heating the admixture or by using a solution at a temperature in the specified temperature range. In some embodiments, the admixture is mixed until substantially all of the buprenorphine acetate salt is dissolved in the solution.

In one embodiment of this third method, substantially all of the buprenorphine acetate salt is dissolved when at least about 80.0 wt %, at least about 85.0 wt %, at least about 90.0 wt %, at least about 95.0 wt %, at least about 98.0 wt %, at least about 99.0 wt %, at least about 99.5 wt %, at least about 99.8 wt %, or at least about 99.9 wt % of the buprenorphine acetate salt is dissolved.

In some embodiments of this third method, the admixture of step (a) is filtered in step (b). The filtering step (b) removes undissolved solids.

In some embodiments of this third method, in step (c) from about 1.0 molar equivalent to about 20.0 molar equivalents, or from about 1.0 molar equivalent to about 5.0 molar equivalents, or from about 1.0 molar equivalent to about 2.0 molar equivalents, or from about 1.0 molar equivalent to about 1.2 molar equivalents of basic material are added, relative to the starting number of moles of acetate salt of buprenorphine in step (a), to the admixture produced in step (a) or (b).

In some embodiments of this third method, the basic material used in step (c) can be any base suitable for preparing buprenorphine free base. In some embodiments, the basic material is selected from a hydroxide, carbonate, alkoxide, hydride, phosphate, borate (such as borax), oxide (such as CaO), cyanide (such as KCN), silicate (such as sodium metasilicate), amine (such as triethylamine, pyridine, or 4-dimethylaminopyridine), and the like, and combinations thereof. In some embodiments, the basic material comprises a hydroxide. In some embodiments, the basic material comprises ammonium hydroxide. In some embodiments, the basic material is aqueous ammonium hydroxide.

In some embodiments of this third method, in step (d) at least about 3.0 mass equivalents of the anti-solvent, relative to the starting mass of acetate salt in step (a), are added to the second admixture produced in step (c) so as to provide a precipitate of buprenorphine free base.

In some embodiments of the third method, the anti-solvent consists essentially of water. In some embodiments, the anti-solvent comprises a mixture of water and an alcohol. In some embodiments, in the mixture of water and alcohol the alcohol comprises IPA. In some embodiments, in the mixture of water and alcohol the alcohol is IPA. In some embodiments, the water and alcohol mixture is from about 95:5 to about 50:50 water:alcohol by volume, or from about 90:10 to about 60:40 water:alcohol by volume, or from about 85:15 to about 70:30 water:alcohol by volume. In some embodiments, the water and alcohol mixture is about 80:20 water:alcohol by volume. In some embodiments, the water and alcohol mixture is from about 95:5 to about 50:50 water:IPA by volume, or from about 90:10 to about 60:40 water:IPA by volume, or from about 85:15 to about 70:30 water:IPA by volume. In some embodiments, the water and alcohol mixture is about 80:20 water:IPA by volume.

In some embodiments of the third method, the minimum time for forming a precipitate of buprenorphine free base in step (d) is about 0.1 hrs. In some embodiments, the time for forming a precipitate of buprenorphine free base is from about 0.1 hrs to about 10.0 hrs, or from about 0.1 hrs to about 6.0 hrs, or from about 0.2 hrs to about 5.0 hrs, or from about 0.1 hr to about 3.0 hrs, or from about 0.3 hrs to about 3.0 hrs, or from about 0.5 hrs to about 3.0 hrs.

Optionally, in some embodiments of the third method, a seed crystal is added in step (d). In particular, the seed crystal comprises buprenorphine free base. The seed crystal can be added in a sufficient amount to initiate precipitation or assist the precipitation of the buprenorphine free base from the second admixture. In some embodiments, from about 0.1 wt % to about 10 wt %, or from about 0.1 wt % to about 9 wt %, or from about 0.1 wt % to about 8 wt %, or from about 0.1 wt % to about 7 wt %, or from about 0.1 wt % to about 6 wt %, or from about 0.1 wt % to about 5 wt %, or from about 0.1 wt % to about 4 wt %, or from about 0.1 wt % to about 3 wt %, or from about 0.1 wt % to about 2 wt %, or from about 0.1 wt % to about 1 wt %, or from about 0.2 wt % to about 0.8 wt %, or from about 0.3 wt % to about 0.7 wt %, or from about 0.4 wt % to about 0.6 wt %, or from about 0.2 wt % to about 0.5 wt % of seed crystal is added to the second admixture of step (d) relative to the starting mass of acetate salt in step (a). In some embodiments, from about 0.2 wt % to about 9 wt %, or from about 0.5 wt % to about 9 wt %, or from about 1 wt % to about 5 wt %, or from about 2 wt % to about 4 wt % of seed crystal is added to the second admixture of step (d) relative to the starting mass of acetate salt in step (a).

In some embodiments, the seed crystal is added at a suitable temperature that initiates precipitation of the buprenorphine free base. In some embodiments, the second admixture of step (d) is at a temperature of from about 40° C. to about 80° C., or from about 45° C. to about 75° C., or from about 50° C. to about 70° C., or from about 50° C. to about 65° C. when the seed crystal is added.

In some embodiments of this third method, the buprenorphine free base prepared in step (d) is isolated in step (e). In some embodiments, the isolating is accomplished by filtration. In some embodiments, the isolation in step (e) is performed at a temperature of at least about 70° C., at least about 65° C., at least about 60° C., at least about 50° C., or at least about 40° C.

In some embodiments, this third method for preparing buprenorphine free base further comprises the step of slurrying the free base obtained from step (e) with a slurrying solution. In some embodiments, the slurring solution comprises water or a mixture of water and an alcohol. In some embodiments, the alcohol comprises IPA. Following formation of this slurry, the free base can be isolated from the slurry, for example, by filtration or by centrifugation.

In some embodiments of this third method, acetic acid in the final free base preparation of buprenorphine is present at less than about 0.7 wt %, less than about 0.5 wt %, less than about 0.3 wt %, less than about 0.2 wt %, or less than about 0.1 wt %.

In another aspect, the disclosure provides the buprenorphine free base prepared by the third method, or by any variations thereof described above. In some embodiments, the buprenorphine free base prepared by the third method is essentially free of impurities.

In some embodiments, the buprenorphine free base prepared by the third method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (10).

In some embodiments, the buprenorphine free base prepared by the third method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (11).

In some embodiments, the buprenorphine free base prepared by the third method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (12).

In some embodiments, the buprenorphine free base prepared by the third method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (13).

In some embodiments, the buprenorphine free base prepared by the third method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (14).

In some embodiments, the buprenorphine free base prepared by the third method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (15).

In some embodiments, for the buprenorphine free base prepared by the third method, the combined level of impurities of the compounds of formulae (10), (11), (12), (13), (14), and (15), is about 0.70 wt % or less, about 0.65 wt % or less, about 0.60 wt % or less, about 0.55 wt % or less, about 0.50 wt % or less, about 0.45 wt % or less, about 0.40 wt % or less, about 0.35 wt % or less, about 0.30 wt % or less, about 0.25 wt % or less, or about 0.20 wt % or less.

In some embodiments, for the buprenorphine free base prepared by the third method, the combined level of impurities of the compounds of formulae (10), (11), (12), (13), (14), and (15), and any other impurity or impurities not specifically identified herein, is about 0.75 wt % or less, about 0.70 wt % or less, about 0.65 wt % or less, about 0.60 wt % or less, about 0.55 wt % or less, about 0.50 wt % or less, about 0.45 wt % or less, about 0.40 wt % or less, about 0.35 wt % or less, about 0.30 wt % or less, about 0.25 wt % or less, or about 0.20 wt % or less.

A fourth method for preparing buprenorphine free base from an acetate salt of buprenorphine, e.g., from buprenorphine acetate tetrahydrate, comprises:

(a) heating an admixture of an acetate salt of buprenorphine and an aqueous solution to provide precipitated buprenorphine free base; and (b) filtering the admixture of step (a) to provide the buprenorphine free base from the precipitate.

In some embodiments of this fourth method for preparing buprenorphine free base from an acetate salt of buprenorphine, the aqueous solution consists essentially of water. In some embodiments of this fourth method for preparing buprenorphine free base from an acetate salt of buprenorphine, the aqueous solution comprises a mixture of water and an alcohol. In some embodiments, in the mixture of water and alcohol the alcohol comprises IPA. In some embodiments, in the mixture of water and alcohol the alcohol is IPA. In some embodiments, the water and alcohol mixture is from about 95:5 to about 50:50 water:alcohol by volume, or from about 90:10 to about 60:40 water:alcohol by volume, or from about 85:15 to about 70:30 water:alcohol by volume. In some embodiments, the water and alcohol mixture is about 80:20 water:alcohol by volume. In some embodiments, the water and alcohol mixture is from about 95:5 to about 50:50 water:IPA by volume, or from about 90:10 to about 60:40 water:IPA by volume, or from about 85:15 to about 70:30 water:IPA by volume. In some embodiments, the water and alcohol mixture is about 80:20 water:IPA by volume.

In some embodiments of this fourth method for preparing buprenorphine free base, the admixture is heated to a temperature of from about 70° C. to about 90° C.

In some embodiments, the fourth method further comprises washing the solid filtered product of step (b) with a second aqueous solution one or more times. The second aqueous solution can be water or a mixture of water and alcohol as above.

In some embodiments, the fourth method further comprises the step of drying the solid filtered solid product of step (b).

In some embodiments of this fourth method, acetic acid in the final free base preparation of buprenorphine is present at less than about 0.7 wt %, less than about 0.5 wt %, less than about 0.3 wt %, less than about 0.2 wt %, or less than about 0.1 wt %.

In another aspect, the disclosure provides the buprenorphine free base prepared by the fourth method, or by any variations thereof described above. In some embodiments, the buprenorphine free base prepared by the fourth method is essentially free of impurities.

In some embodiments, the buprenorphine free base prepared by the fourth method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (10).

In some embodiments, the buprenorphine free base prepared by the fourth method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (11).

In some embodiments, the buprenorphine free base prepared by the fourth method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (12).

In some embodiments, the buprenorphine free base prepared by the fourth method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (13).

In some embodiments, the buprenorphine free base prepared by the fourth method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (14).

In some embodiments, the buprenorphine free base prepared by the fourth method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (15).

In some embodiments, for the buprenorphine free base prepared by the fourth method, the combined level of impurities of the compounds of formulae (10), (11), (12), (13), (14), and (15), is about 0.70 wt % or less, about 0.65 wt % or less, about 0.60 wt % or less, about 0.55 wt % or less, about 0.50 wt % or less, about 0.45 wt % or less, about 0.40 wt % or less, about 0.35 wt % or less, about 0.30 wt % or less, about 0.25 wt % or less, or about 0.20 wt % or less.

In some embodiments, for the buprenorphine free base prepared by the fourth method, the combined level of impurities of the compounds of formulae (10), (11), (12), (13), (14), and (15), and any other impurity or impurities not specifically identified herein, is about 0.75 wt % or less, about 0.70 wt % or less, about 0.65 wt % or less, about 0.60 wt % or less, about 0.55 wt % or less, about 0.50 wt % or less, about 0.45 wt % or less, about 0.40 wt % or less, about 0.35 wt % or less, about 0.30 wt % or less, about 0.25 wt % or less, or about 0.20 wt % or less.

A fifth method for preparing buprenorphine free base from an acetate salt of buprenorphine, e.g., from buprenorphine acetate tetrahydrate, comprises:

(a) mixing an acetate salt of buprenorphine in a solvent to form an admixture;

(b) refluxing the admixture at a reflux temperature and removing the acetate as acetic acid in the vapor phase;

(c) cooling the admixture to provide precipitated buprenorphine free base; and (d) isolating the buprenorphine free base.

In some embodiments of this fifth method for preparing buprenorphine free base from an acetate salt of buprenorphine, the isolating of step (d) comprises filtering the precipitated buprenorphine free base of step (c).

In some embodiments of this fifth method, the solvent comprises an organic solvent. In some embodiments, the organic solvent can be selected from hexane, heptane, IPA, methanol, ethanol, n-propanol, n-butanol, iso-butanol, tert-butanol, acetonitrile, ethyl acetate, methyl ethyl ketone, methyl iso-butyl ketone, cyclohexane, toluene, tetrahydrofuran, and any mixture of two or more thereof.

In any of the above embodiments of the fifth method, the removing of the acetic acid can be done using a condenser in combination with a distillation head or a Dean-Stark trap.

In some embodiments of this fifth method, acetic acid in the final free base preparation of buprenorphine is present at less than about 0.7 wt %, less than about 0.5 wt %, less than about 0.3 wt %, less than about 0.2 wt %, or less than about 0.1 wt %.

In another aspect, the disclosure provides buprenorphine free base prepared by the fifth method, or by any variations thereof described above. In some embodiments, the buprenorphine free base prepared by the fifth method is essentially free of impurities.

In some embodiments, the buprenorphine free base prepared by the fifth method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (10).

In some embodiments, the buprenorphine free base prepared by the fifth method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (11).

In some embodiments, the buprenorphine free base prepared by the fifth method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (12).

In some embodiments, the buprenorphine free base prepared by the fifth method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (13).

In some embodiments, the buprenorphine free base prepared by the fifth method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula, (14).

In some embodiments, the buprenorphine free base prepared by the fifth method comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (15).

In some embodiments, for the buprenorphine free base prepared by the fifth method, the combined level of impurities of the compounds of formulae (10), (11), (12), (13), (14), and (15), is about 0.70 wt % or less, about 0.65 wt % or less, about 0.60 wt % or less, about 0.55 wt % or less, about 0.50 wt % or less, about 0.45 wt % or less, about 0.40 wt % or less, about 0.35 wt % or less, about 0.30 wt % or less, about 0.25 wt % or less, or about 0.20 wt % or less.

In some embodiments, for the buprenorphine free base prepared by the fifth method, the combined level of impurities of the compounds of formulae (10), (11), (12), (13), (14), and (15), and any other impurity or impurities not specifically identified herein, is about 0.75 wt % or less, about 0.70 wt % or less, about 0.65 wt % or less, about 0.60 wt % or less, about 0.55 wt % or less, about 0.50 wt % or less, about 0.45 wt % or less, about 0.40 wt % or less, about 0.35 wt % or less, about 0.30 wt % or less, about 0.25 wt % or less, or about 0.20 wt % or less.

In a further aspect, the disclosure further provides other buprenorphine salts prepared from the free base, where the free base is prepared from an acetate salt of buprenorphine, as described herein. Accordingly, in some embodiments, the buprenorphine salt can be represented by formula (1c),

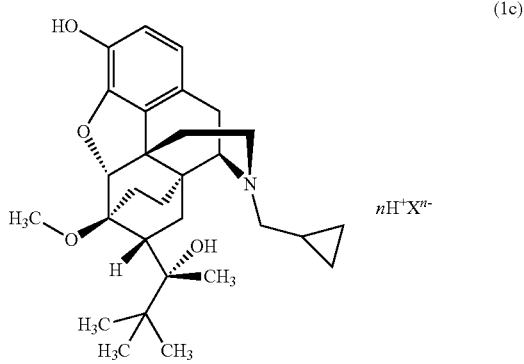

(1c)

or a solvate thereof;

where $X^{n-}$ is an anion and n is 1, 2, or 3. In certain embodiments, $X^{n-}$ is an anion selected from the group consisting of $F^-$, $Cl^-$, $Br^-$, $I^-$, valerate, acetate, meconate, salicylate, barbiturate, succinate, tartrate, maleate, fumarate, citrate, methanesulfonate, tosylate, trifluoroacetate, oxalate, perchlorate, $NO_3^-$, $HSO_4^-$, $SO_4^{2-}$, $H_2PO_4^-$, $HPO_4^{2-}$, $PO_4^{3-}$, $[(NH_4)HPO_4]^-$, $[(NH_4)_2PO_4]^-$, and $HCOO^-$. In another embodiment, $X^{n-}$ is $Cl^-$.

A salt of formula (1c) can be obtained by adding an acid $H^+_n X^{n-}$ to the buprenorphine free base.

In some embodiments, the acid $H^+_n X^{n-}$ is selected from the group consisting of HCl, $H_2SO_4$, $H_3PO_4$, and HCOOH. In another embodiment, the acid $H^+_n X^{n-}$ is HCl.

In some embodiments, the amount of acid added to the buprenorphine free base is from about 0.5 molar equivalents to about 10 molar equivalents based on the total molar equivalents of the free base present in the composition. In some embodiments, the amount of acid is from about 1 molar equivalent to about 6 molar equivalents. In some embodiments, the amount of acid is from about 2 molar equivalents to about 3 molar equivalents. In some embodiments, the amount of acid is from about 2.2 molar equivalents to about 2.6 molar equivalents.

In some embodiments, the salt of formula (1c) can be an anhydrate, a solvate, or a hydrate. In some embodiments, the salt of formula (1c) is an anhydrate. In some embodiments, the salt of formula (1c) is a hydrate and the hydrate is a monohydrate, dihydrate, trihydrate, tetrahydrate, pentahydrate, or hexahydrate. In some embodiments, the hydrate is a tetrahydrate.

In some embodiments, the buprenorphine free base prepared by any of the aforementioned methods comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (10):

(10)
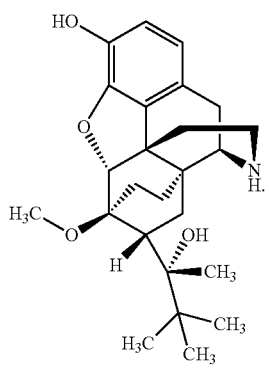

In some embodiments, the buprenorphine free base prepared by any of the aforementioned methods comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (11):

(11)
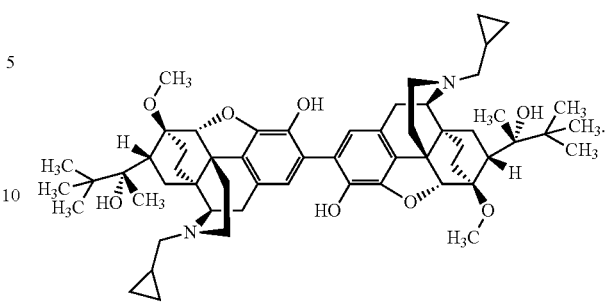

In some embodiments, the buprenorphine free base prepared by any of the aforementioned methods comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (12):

(12)
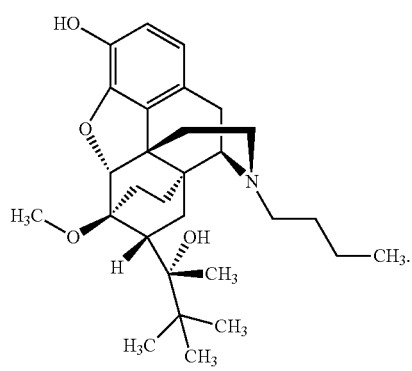

In some embodiments, the buprenorphine free base prepared by any of the aforementioned methods comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (13):

(13)
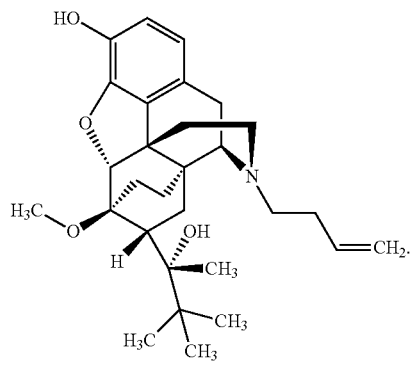

In some embodiments, the buprenorphine free base prepared by any of the aforementioned methods comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (14):

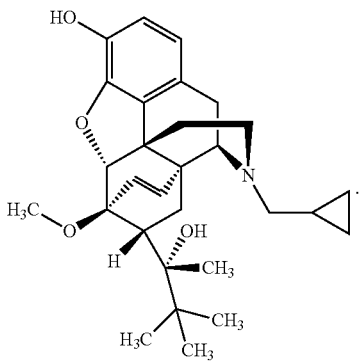

(14)

In some embodiments, the buprenorphine free base prepared by any of the aforementioned methods comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (15):

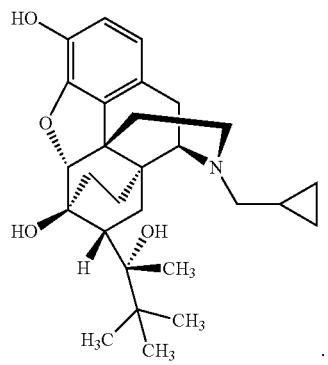

(15)

In some embodiments, the buprenorphine free base prepared by any of the aforementioned methods comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (16):

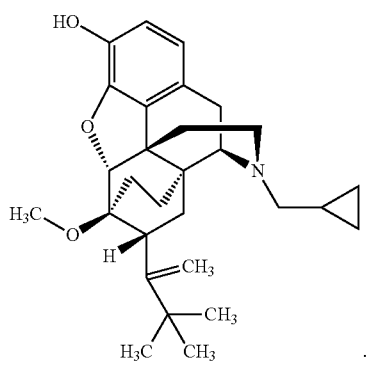

(16)

In some embodiments, the buprenorphine free base prepared by any of the aforementioned methods comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (17):

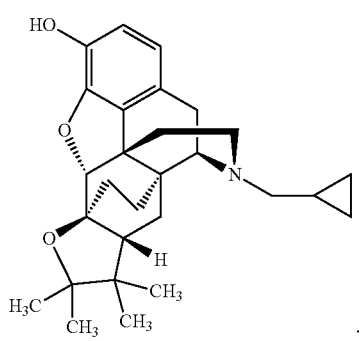

(17)

In some embodiments, the buprenorphine free base prepared by any of the aforementioned methods comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (18):

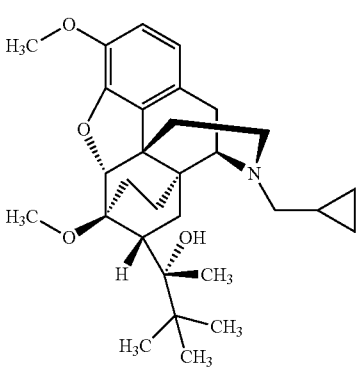

(18)

In some embodiments, the buprenorphine free base prepared by any of the aforementioned methods comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (19):

(19)

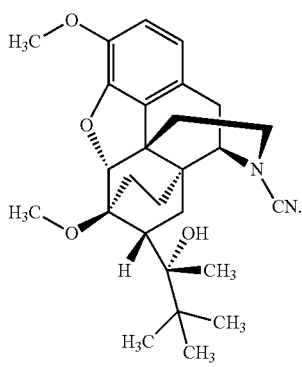

In some embodiments, a salt prepared from the buprenorphine free base prepared by any of the methods above comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (10):

(10)

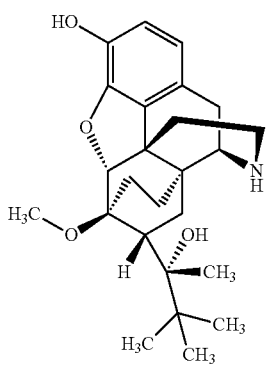

or a salt thereof.

In some embodiments, a salt prepared from the buprenorphine free base prepared by any of the aforementioned methods comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (11):

(11)

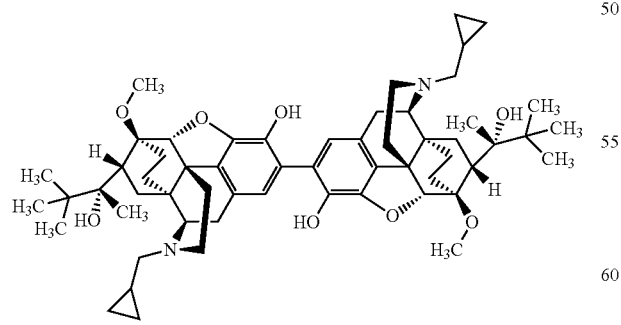

or a salt thereof.

In some embodiments, a salt prepared from the buprenorphine free base prepared by any of the methods above comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (12):

(12)

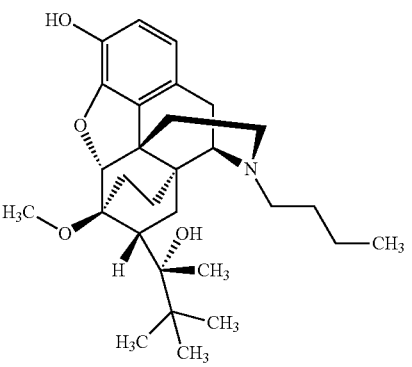

or a salt thereof.

In some embodiments, a salt prepared from the buprenorphine free base prepared by any of the methods above comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (13):

(13)

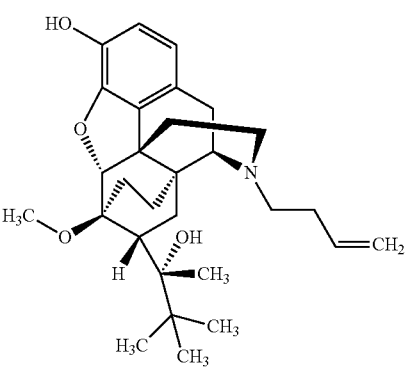

or a salt thereof.

In some embodiments, a salt prepared from the buprenorphine free base prepared by any of the methods above comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (14):

(14)

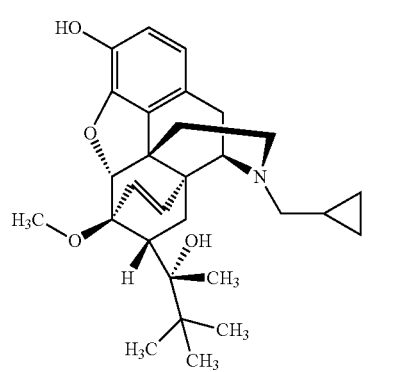

or a salt thereof.

In some embodiments, a salt prepared from the buprenorphine free base prepared by any of the methods above comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (15):

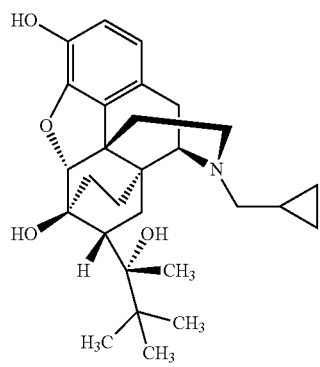

(15)

or a salt thereof.

In some embodiments, a salt prepared from the buprenorphine free base prepared by any of the methods above comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (16):

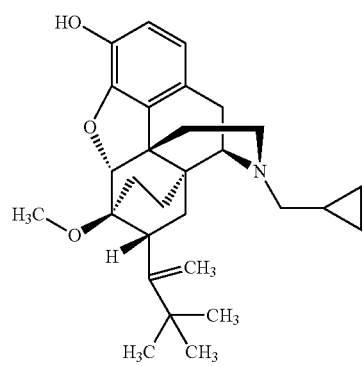

(16)

or a salt thereof.

In some embodiments, a salt prepared from the buprenorphine free base prepared by any of the methods above comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (17):

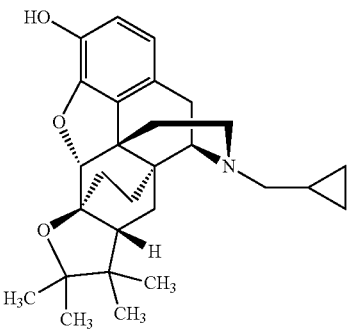

(17)

or a salt thereof.

In some embodiments, a salt prepared from the buprenorphine free base prepared by any of the methods above comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (18):

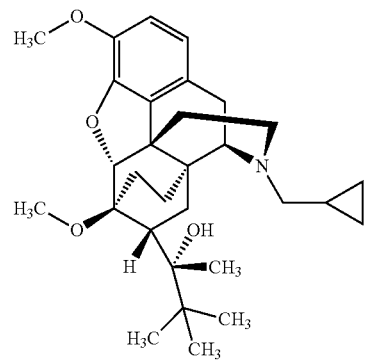

(18)

or a salt thereof.

In some embodiments, a salt prepared from the buprenorphine free base prepared by any of the methods above comprises about 0.10 wt % or less, about 0.09 wt % or less, about 0.08 wt % or less, about 0.07 wt % or less, about 0.06 wt % or less, or about 0.05 wt % or less of an impurity represented by the compound of formula (19):

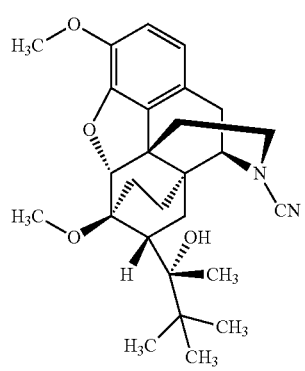

(19)

or a salt thereof.

In some embodiments, the buprenorphine free base prepared by any of the aforementioned methods, and the salts and pharmaceutical compositions prepared therefrom, are essentially free of impurities. In some embodiments, for the buprenorphine free base prepared by any of the aforementioned methods, and the salts prepared therefrom, the combined level of impurities of the compounds of formulae (10), (11), (12), (13), (14), (15), (16), (17), (18), and (19) that may be present, is about 0.70 wt % or less, about 0.65 wt % or less, about 0.60 wt % or less, about 0.55 wt % or less, about 0.50 wt % or less, about 0.45 wt % or less, about 0.40 wt % or less, about 0.35 wt % or less, about 0.30 wt % or less, about 0.25 wt % or less, or about 0.20 wt % or less.

In some embodiments, for the buprenorphine free base prepared by any of the aforementioned methods, and the salts prepared therefrom, the total amount of impurities, including the combined level of impurities of the compounds of formulae (10), (11), (12), (13), (14), (15), (16), (17), (18), and (19), is about 0.70 wt % or less, about 0.65 wt % or less, about 0.60 wt % or less, about 0.55 wt % or less, about 0.50 wt % or less, about 0.45 wt % or less, about 0.40 wt % or less, about 0.35 wt % or less, about 0.30 wt % or less, about 0.25 wt % or less, about 0.20 wt % or less, about 0.15 wt % or less, or about 0.10 wt % or less.

In some embodiments, for the free base preparation of buprenorphine prepared by any of the aforementioned methods, and the salts prepared therefrom, the total amount of impurities, including the combined level of impurities of the compounds of formulae (10), (11), (12), (13), (14), (15), (16), (17), (18), and (19) that may be present, and any other impurity or impurities not specifically identified herein, is about 0.75 wt % or less, about 0.70 wt % or less, about 0.65 wt % or less, about 0.60 wt % or less, about 0.55 wt % or less, about 0.50 wt % or less, about 0.45 wt % or less, about 0.40 wt % or less, about 0.35 wt % or less, about 0.30 wt % or less, about 0.25 wt %, about 0.20 wt % or less, about 0.15 wt % or less, or about 0.10 wt % or less.

In some embodiments, for the buprenorphine free base prepared by any of the methods above, and the salts and pharmaceutical compositions prepared therefrom, the amount of specific impurities of the compounds of formulae (10) through (19), particularly the compounds of formulae (10) through (15), is at or below the threshold level (or threshold limit) specified by the United States Pharmacopeia ("USP"), FDA, EMA, or ICH monographs/guidelines for buprenorphine. In some embodiments, the buprenorphine free base prepared by any of the methods above, and the salts and pharmaceutical compositions prepared therefrom, have an amount of all of the impurities set out in the following Table 2 at or below the level of the threshold limit or the threshold value (in wt %) provided in Table 2.

TABLE 2

| Impurity (ICH/EMA Designation) | Measured Impurity Level [1] | Threshold Limit [2] | Threshold Value (EMA) [2] |
| --- | --- | --- | --- |
| Compound of formula (10) (Impurity B) | ND | <0.10% | NMT 0.20% |
| Compound of formula (11) (Impurity G) | ND | NMT 0.10% | NMT 0.15% |
| Compound of formula (12) (Impurity H) | 0.05% | NMT 0.10% | NMT 0.25% |
| Compound of formula (13) (Impurity A) | ND | NMT 0.20% | NMT 0.20% |
| Compound of formula (14) (Impurity J) | 0.07% | NMT 0.10% | NMT 0.20% |
| Compound of formula (15) (Impurity E) | ND | <0.10% | None Provided |
| Compound of formula (16) (Impurity F) | ND | NMT 0.10% | NMT 0.20% |
| Compound of formula (17) (Impurity I) | NT | None Provided | None Provided |
| Compound of formula (18) (Impurity D) | ND | <0.10% | None Provided |
| Compound of formula (19) (Impurity C) | ND | <0.10% | None Provided |
| Impurities not specifically identified herein | 0.00% | NMT 0.10% | NMT 0.10% |
| Total Impurity | 0.12% | NMT 0.65% | NMT 0.70% |

[1] ND = Not Detected, NT = Not Tested
[2] NMT = Not More Than

In some embodiments, the buprenorphine free base prepared by any of the methods above, and the salts and pharmaceutical compositions prepared therefrom, are characterized by a measured impurity profile for all of the impurities set out in Table 2 above which is at or below the level of the measured impurity profile provided in Table 2.

In some embodiments, the buprenorphine free base prepared by any of the aforementioned methods is converted into a pharmaceutically acceptable salt thereof by reaction of the buprenorphine free base with an appropriate acid according to the guidance in the present disclosure or by any of a variety of known methods in view of the present disclosure. In one embodiment, the buprenorphine free base prepared by any of the aforementioned methods is converted into buprenorphine hydrochloride by the reaction of buprenorphine free base with HCl. In one embodiment, the buprenorphine free base prepared by any of the methods above is converted into the levulinic acid-salt of buprenorphine by the reaction of buprenorphine free base with levulinic acid.

4.5 Pharmaceutical Compositions

In another aspect, the disclosure further provides pharmaceutical compositions of buprenorphine compounds prepared according to the methods described herein, including the corresponding salts, solvates, hydrates, and crystalline forms, and particularly pharmaceutically acceptable salts of buprenorphine.

Accordingly, in some embodiments, a pharmaceutical composition of the disclosure comprises an acetate salt of buprenorphine. In some embodiments, a pharmaceutical composition of the disclosure comprises a hydrochloride salt of buprenorphine. In some embodiments, a pharmaceutical composition of the disclosure comprises a levulinate salt of buprenorphine. In some embodiments, the pharmaceutical composition comprises buprenorphine in anhydrous form. In some embodiments, the pharmaceutical composition comprises a hydrate of buprenorphine. In some embodiments, the pharmaceutical composition comprises a hydrate of buprenorphine acetate. In some embodiments, the pharmaceutical composition comprises buprenorphine acetate tetrahydrate.

In some embodiments, the pharmaceutical composition comprises buprenorphine, a hydrate thereof, or a particular crystalline form thereof, prepared by any of the aforementioned methods for preparing the compound of formula (1), its hydrates, and crystalline form as described herein, particularly in Section 4.3 of the disclosure and in the examples.

In some embodiments, the pharmaceutical composition comprises buprenorphine, a hydrate thereof, or a particular crystalline form thereof having the level of impurities described herein, including the level of impurities for the compounds of formulae (10), (11), (12), (13), (14), and (15), as described herein.

In some embodiments, the pharmaceutical composition comprises buprenorphine free base prepared by a method of the disclosure.

In some embodiments, the pharmaceutical composition comprises buprenorphine free base having the level of impurities described herein, including the level of impurities for one or more of the compounds of formulae (10), (11), (12), (13), (14), and (15), as described herein.

As further described herein, the buprenorphine compounds and compositions of the disclosure can be used alone or in combination with other therapeutic agents to treat a Condition in an animal in need thereof. Accordingly, in some embodiments the pharmaceutical composition is formulated to contain a buprenorphine compound of the disclosure without other therapeutic agents. In other embodiments, the pharmaceutical composition is formulated to contain a buprenorphine compound of the disclosure (a first therapeutic agent) and one or more other therapeutic agents (e.g., one or more second therapeutic agent(s)).

Pharmaceutical compositions of the disclosure can take the form of solutions, suspensions, emulsions, tablets, pills, pellets, multi-particulates, capsules, capsules containing liquids, capsules containing powders, capsules containing beads or multi-particulates, lozenges, immediate-release oral formulations, controlled-release formulations, sustained-release formulations, suppositories, aerosols, sprays, formulations for inhalation, transdermal delivery systems (e.g., patches, aerosols, sprays, gels, salves, ointments), intra-ocular formulations, transmucosal delivery devices (e.g., for gingival, buccal intra-nasal, rectal, vaginal, or sub-lingual delivery), or any other form suitable for use. In some embodiments, the composition is in the form of a capsule (see, e.g., U.S. Pat. No. 5,698,155). Other examples of suitable pharmaceutical excipients are described in Radebough et al., "Preformulation," pp. 1447-1676 in Remington's Pharmaceutical Sciences Vol. 2 (Gennaro, ed., 19$^{th}$ Ed., Mack Publishing, Easton, Pa., 1995), incorporated herein by reference.

In some embodiments, the pharmaceutical compositions of the disclosure preferably comprise a suitable amount of one or more pharmaceutically acceptable excipients to provide the form for proper administration to an animal by the particular route. Such pharmaceutical excipients can be selected from diluents, suspending agents, solubilizers, binders, disintegrants, buffers, glidants, preservatives, coloring agents, anti-oxidants, lubricants, and the like. Pharmaceutical excipients can be a liquid, such as water or an oil, including those of petroleum, animal, vegetable, or synthetic origin, such as peanut oil, soybean oil, mineral oil, sesame oil, and the like. Pharmaceutical excipients can be saline, gum acacia, gelatin, starch paste, talc, keratin, colloidal silica, urea, and the like. In addition, auxiliary, stabilizing, thickening, lubricating, and coloring agents can be used. In a preferred embodiment, a pharmaceutically acceptable excipient is sterile when administered to an animal. Water is a particularly useful excipient when the pharmaceutical composition is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The compositions, if desired, can also contain minor amounts of wetting agents, emulsifying agents, or pH buffering agents. Specific examples of pharmaceutically acceptable carriers and excipients that can be used to formulate particular dosage forms are described in the *Handbook of Pharmaceutical Excipients*, (Amer. Pharmaceutical Ass'n, Washington, D.C., 1986).

In some embodiments, the buprenorphine compounds or the pharmaceutical compositions of the disclosure are formulated for transdermal administration, such as by using a transdermal patch. A transdermal patch can comprise, e.g., a buprenorphine compound of the disclosure contained in a reservoir or a matrix, and an adhesive, which allows the transdermal device to adhere to the skin and also allows the passage of the buprenorphine compound of the disclosure from the transdermal device through the skin of an animal. In another embodiment, a transdermal patch can comprise, e.g., a pharmaceutical composition comprising a buprenorphine compound of the disclosure contained in a reservoir or a matrix, and an adhesive, which allows the transdermal device to adhere to the skin and also allows the passage of the pharmaceutical composition from the transdermal device through the skin of the animal.

Suitable transdermal formulations are described in U.S. Pat. Nos. 6,264,980, 6,344,211, RE41,408, RE41,489, and RE41,571; U.S. Pat. Application Publication Nos. 2010/0119585 and 2014/0363487; and International Patent Publication Nos. WO 2013/088254, WO 2014/090921, and WO 2014/195352, each of which is incorporated herein by reference. A suitable transdermal formulation comprises a buprenorphine (e.g., buprenorphine free base) impermeable backing layer and a pressure-sensitive adhesive layer on the buprenorphine-impermeable backing layer. The pressure-sensitive adhesive layer is the skin contact layer. The pressure-sensitive adhesive layer comprises at least one polymer-based pressure-sensitive adhesive, an analgesically effective amount of buprenorphine free base or a pharmaceutically acceptable salt thereof, and a carboxylic acid. The carboxylic acid is present in an amount sufficient so that the analgesically effective amount of buprenorphine is solubilized in the carboxylic acid to form a mixture and so that the carboxylic acid-buprenorphine mixture forms dispersed deposits in the pressure-sensitive adhesive layer. The carboxylic acid is selected from oleic acid, linoleic acid, linolenic acid, levulinic acid, and mixtures thereof. In one embodiment, the carboxylic acid is levulinic acid. In another embodiment, the pressure-sensitive adhesive is based on polysiloxane. In another embodiment, the pressure-sensitive adhesive is based on polysiloxane and the carboxylic acid is levulinic acid.

In some embodiments, the buprenorphine is administered in the transdermal system to provide, e.g., a dosing interval of about 24 hours, a dosing interval of about 3 days, or a dosing interval of about 7 days. In some embodiments, the transdermal buprenorphine system can be formulated to administer buprenorphine, e.g., at a rate of from about 0.001 mcg/hour to about 50 mcg/hour, or from about 0.01 mcg/hour to about 40 mcg/hour, or from about 0.05 mcg/hour to about 30 mcg/hour, or from about 0.1 mcg/hour to about 20 mcg/hour or from about 0.5 mcg/hour to about 10 mcg/hour. In some embodiments, the transdermal buprenorphine system can be formulated to administer buprenorphine, e.g., at a rate of from about 0.001 mcg/hour to about 5 mcg/hour, or from about 0.01 mcg/hour to about 4 mcg/hour, or from about 0.05 mcg/hour to about 3 mcg/hour, or from about 0.1 mcg/hour to about 2 mcg/hour, or from about 0.5 mcg/hour to about 1 mcg/hour. In some embodiments, the transdermal buprenorphine system can be formulated to administer buprenorphine, e.g., at a rate of about 50 mcg/hour, about 40 mcg/hour, about 30 mcg/hour, about 20 mcg/hour, about 10 mcg/hour, about 5 mcg/hour, about 4 mcg/hour, about 3 mcg/hour, about 2 mcg/hour, about 1 mcg/hour, about 0.5 mcg/hour, about 0.1 mcg/hour, about 0.05 mcg/hour, about 0.01 mcg/hour, or about 0.001 mcg/hour.

In some embodiments, the pharmaceutical compositions are formulated for oral administration. A pharmaceutical composition of the disclosure to be orally delivered can be in the form of tablets, capsules, gelcaps, caplets, lozenges, aqueous or oily solutions, suspensions, granules, powders, emulsions, syrups, quick dissolving tablets (such as for sub-lingual delivery), quick dissolving strips (such as for buccal delivery), or elixirs, for example. When the buprenorphine or other (e.g., a second) therapeutic agent is incorporated into oral tablets, such tablets can be compressed, tablet triturates, enteric-coated, sugar-coated, film-coated, multi-ply compressed or multiply layered.

An orally administered pharmaceutical composition can contain one or more additional agents such as, for example, sweetening agents such as fructose, aspartame or saccharin; flavoring agents such as peppermint, oil of wintergreen, or cherry; coloring agents; and preserving agents, and stabilizers, to provide stable, pharmaceutically palatable dosage forms. Techniques and compositions for making solid oral dosage forms are described in *Pharmaceutical Dosage Forms: Tablets* (Lieberman et al., eds., $2^{nd}$ Ed., Marcel Dekker, Inc., 1989 and 1990). Techniques and compositions for making tablets (compressed and molded), capsules (hard and soft gelatin) and pills are also described in King, "Tablets, Capsules, and Pills," pp. 1553-1593 in *Remington's Pharmaceutical Sciences* (Osol, ed., $16^{th}$ Ed., Mack Publishing, Easton, Pa., 1980). Liquid oral dosage forms can include both aqueous and nonaqueous solutions, emulsions, and suspensions. Techniques and compositions for making liquid oral dosage forms are described in *Pharmaceutical Dosage Forms: Disperse Systems* (Lieberman et al., eds., $2^{nd}$ Ed., Marcel Dekker, Inc., 1996 and 1998).

When the buprenorphine or the second therapeutic agent is formulated for parenteral administration by injection (e.g., continuous infusion or bolus injection), the formulation can be in the form of a suspension, solution, or emulsion in an oily or aqueous vehicle, and such formulations can further comprise pharmaceutically necessary additives such as one or more buffering agents, stabilizing agents, suspending agents, dispersing agents, and the like. When the formulation of the disclosure is to be injected parenterally, it can be, e.g., in the form of an isotonic sterile solution. The formulation can also be in the form of a powder (e.g., lyophilized) adapted for reconstitution as an injectable formulation.

In some embodiments, a pharmaceutical composition of the disclosure is adapted for intravenous administration. Typically, such compositions comprise sterile isotonic aqueous buffer. Where necessary, the compositions can also include a solubilizing agent. A pharmaceutical composition for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where the pharmaceutical composition of the disclosure is to be administered by infusion, it can be dispensed, for example, with an infusion bottle containing sterile pharmaceutical grade water or saline. When the pharmaceutical composition of the disclosure is administered by injection, an ampule of sterile water for injection or saline can be provided so that the ingredients can be mixed prior to administration.

When a pharmaceutical compositions of the disclosure is to be administered by inhalation, it can be formulated into a dry aerosol, or an aqueous or partially aqueous solution.

In some embodiments, the pharmaceutical compositions of the disclosure can be delivered in vesicles, in particular a liposome (see Langer, "New Methods of Drug Delivery," *Science* 249:1527-1533 (1990) (hereafter "Langer") and Treat et al., "Liposome Encapsulated Doxorubicin Preliminary Results of Phase I and Phase II Trials," pp. 317-327 and 353-365 in *Liposomes in the Therapy of Infectious Disease and Cancer* (1989)).

In some embodiments, the pharmaceutical compositions of the disclosure can be delivered in an immediate release form. In other embodiments, the pharmaceutical compositions of the disclosure can be delivered in a controlled-release system or sustained-release system. Controlled-release or sustained-release pharmaceutical compositions can have a common goal of improving drug therapy compared to the results achieved by their non-controlled or non-sustained-release counterparts. Advantages of controlled-release or sustained-release compositions include extended activity of the drug, reduced dosage frequency, and increased compliance. In addition, controlled-release or sustained-release compositions can favorably affect the time of onset of action or other characteristics, such as blood levels of the buprenorphine and/or another therapeutic agent, and can thus reduce the occurrence of adverse side effects.

Controlled-release or sustained-release compositions can have an immediate release component that initially releases an amount of the buprenorphine or another therapeutic agent to promptly produce the desired therapeutic or prophylactic effect, and then gradually and continually releases other amounts of the buprenorphine or another therapeutic agent to maintain a level of therapeutic or prophylactic effect over an extended period of time. To maintain a constant level of the buprenorphine and/or another therapeutic agent in the body, the pharmaceutical composition can be adapted to release the active ingredient(s) from the dosage form at a rate that will replace the amount of active(s) being metabolized and excreted from the body. Controlled or sustained release of an active ingredient can be triggered by any of various conditions, including but not limited to, changes in pH, changes in temperature, concentration or availability of enzymes, concentration or availability of water, or other physiological conditions or compounds.

Controlled-release and sustained-release means which may be adapted for use according to the disclosure may be selected from those known in the art. Examples include, but are not limited to, those described in U.S. Pat. Nos. 3,845,770, 3,916,899, 3,536,809, 3,598,123, 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide controlled-release or sustained-release of one or both of the active ingredients using, for example, hydropropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled-release or sustained-release formulations known in the art, including those described herein, can be readily adapted for use with the active ingredients of the disclosure. See also Goodson, "Dental Applications," in *Medical Applications of Controlled Release, Vol. 2, Applications and Evaluation*, Langer and Wise, eds., CRC Press, Chapter 6, pp. 115-138 (1984). Other controlled-release or sustained-release systems that are discussed in the review by Langer can be adapted for use according to the disclosure. In some embodiments, a pump can be used, e.g., Saudek et al., "A Preliminary Trial of the Programmable Implantable Medication System for Insulin Delivery," *New Engl. J. Med.* 321:574-579 (1989)). In some embodiments, polymeric materials can be implanted, e.g., Langer et al., "Chemical and Physical Structure of Polymers as Carriers for Controlled Release of Bioactive Agents: A Review," *J. Macromol. Sci. Rev. Macromol. Chem.* C23(1): 61-126 (1983).

When in oral dosage form as a tablet or pill, a pharmaceutical composition of the disclosure can be coated to delay disintegration and absorption in the gastrointestinal tract thereby providing targeted release to a particular portion of the gastrointestinal tract, or providing a sustained action over an extended period of time. Selectively permeable membranes surrounding an osmotically active driving compound (osmagent) can also be suitable for orally administered compositions. In these latter platforms, fluid from the environment surrounding the capsule is imbibed by the driving compound, which swells to displace the agent through an aperture in the wall of the dosage form. Such delivery platforms can provide an essentially zero order delivery profile as opposed to the spiked profiles of immediate release formulations. A time-delay material such as glycerol monostearate or glycerol stearate can also be used. Oral compositions preferably include standard excipients of pharmaceutical grade selected, for example, from mannitol, lactose, starch, magnesium stearate, sodium saccharin, cellulose, and magnesium carbonate, among others.

In some embodiments, the dosage form can further comprise at least one polymer. Examples of polymers include but are not limited to a maltodextrin polymer comprising the formula $(C_6H_{12}O_5)_n$ where n is from 3 to 7,500, a poly (alkylene oxide) such as a poly(ethylene oxide) and a poly(propylene oxide), an alkali carboxyalkylcellulose, where the alkali is sodium or potassium and the alkyl is methyl, ethyl, propyl, or butyl, and a copolymer of ethylene-acrylic acid, ethylene-methacrylic acid, or ethylene-ethacrylic acid.

In some embodiments, the polymer is selected from the group consisting of a polyalkylene oxide and a carboxyalkylcellulose. The polyalkylene oxide may be a member selected from the group consisting of polymethylene oxide, polyethylene oxide ("PEO"), and polypropylene oxide. The carboxyalkylcellulose may be a member selected from the group consisting of alkali carboxyalkylcellulose, sodium carboxymethylcellulose, potassium carboxymethylcellulose, sodium carboxyethylcellulose, lithium carboxymethylcellulose, sodium carboxyethylcellulose, carboxyalkylhydroxyalkylcellulose, carboxymethylhydroxyethylcellulose, carboxyethylhydroxyethylcellulose and carboxymethylhydroxypropylcellulose.

In some embodiments, the PEO polymer in the dosage form is a high molecular weight PEO, i.e., having a molecular weight of at least 0.5 million in one embodiment and, in another embodiment, at least 1 million up to 15 million. The PEO molecular weight is determined by rheological measurements, e.g., as disclosed in U.S. Pat. No. 8,075,872 at column 6, lines 5-14, incorporated herein by reference. High molecular weight PEO polymers have a viscosity at 25° C. of 4500 cP to 17600 cP measured on a 5 wt % aqueous solution using a model RVF Brookfield viscosimeter (spindle no. 2/rotational speed 2 rpm), of 400 cP to 4000 cP measured on a 2 wt % aqueous solution using the stated viscosimeter (spindle no. 1 or 3/rotational speed 10 rpm), or of 1650 cP to 10000 cP measured on a 1 wt % aqueous solution using the stated viscosimeter (spindle no. 2/rotational speed 2 rpm).

Dosage forms containing polyalkylene oxide, particularly PEO, and more particularly high molecular weight PEO, each having a breaking strength of at least 500 N, are advantageous because, due to the hardness they impart to, e.g., a tablet, such dosage form cannot be pulverized in conventional comminution means available to a drug abuser, such as a mortar and pestle. This virtually rules out oral or parenteral, in particular intravenous or nasal, abuse. Tamper-resistant unpulverizable dosage forms are disclosed in, e.g., U.S. Pat. Nos. 8,075,872, 8,114,383, 8,192,722, and 8,309,060, incorporated herein by reference.

In some embodiments, the carboxyalkylcellulose polymer in the dosage form is selected so as to impart a gel-like quality to a dosage form that is tampered with, thereby reducing the potential for abuse of the buprenorphine compounds of the disclosure in the dosage form through spoiling or hindering the pleasure of obtaining a rapid high from the tampered dosage form due to the gel-like consistency. For example, the gel-like consistency, when in contact with the mucous membrane, prevents the abuse of the tampered dosage form by minimizing absorption (e.g., in the nasal passages) or provides substantial difficulty in injecting the tampered dosage form (e.g., due to difficulty pushing the tampered dosage form through a syringe or pain upon administration) because of the high viscosity imparted to the tampered dosage form.

A carboxyalkylcellulose gelling agent may be added to the formulation in a ratio of gelling agent:buprenorphine compounds of the disclosure of from about 1:40 to about 40:1 by weight in one embodiment, or from about 1:1 to about 30:1 by weight in another embodiment, or from about 2:1 to about 10:1 by weight in another embodiment so that the dosage form forms a viscous gel after the dosage form is tampered with, dissolved in an aqueous liquid (in from about 0.5 mL to about 10 mL and preferably from about 1 mL to about 5 mL of the aqueous liquid), causing the resulting mixture to have a viscosity of at least about 10 cP in one embodiment and, in another embodiment, a viscosity of at least about 60 cP. In another embodiment, the carboxyalkylcellulose gelling agent causes the dosage form to form a viscous gel after the dosage form is tampered with, dissolved in an aqueous liquid (in from about 0.5 mL to about 10 mL and preferably from about 1 mL to about 5 mL of the aqueous liquid) and then heated (e.g., to greater than about 45° C.), causing the resulting mixture to have a viscosity of at least about 10 cP in one embodiment and, in another embodiment, a viscosity of at least about 60 cP. Tamper-resistant dosage forms containing a gelling agent are disclosed in, e.g., U.S. Pat. Nos. 7,842,307, 8,337,888, 8,524,275, 8,529,948, and 8,609,683, incorporated herein by reference.

4.6 Methods of Use

The buprenorphine compounds of the disclosure are useful in human and veterinary medicine. As further described herein, the buprenorphine compounds are useful for treating or preventing a Condition in an animal in need thereof.

When administered to an animal, the buprenorphine compounds can be administered as a component of a composition that comprises one or more pharmaceutically acceptable carriers or excipients. The compositions can be administered by any convenient route and also administered together with a second therapeutically active agent. Administration can be systemic or local.

In some embodiments, the methods of administration include, but are not limited to, intradermal, intramuscular, intraperitoneal, parenteral, intravenous, subcutaneous, intranasal, epidural, oral, sublingual, intracerebral, intravaginal, transdermal (e.g., via a patch), rectal, by inhalation, transmucosal, or topical, particularly to the ears, nose, eyes, or skin. The method of administration is left to the discretion of the practitioner. In some instances, administration will result in the release of the buprenorphine compound into the bloodstream. In other instances, administration will result in only local release of the buprenorphine compound.

In some embodiments, the buprenorphine compounds and pharmaceutical compositions of the disclosure can be used to treat Conditions known to be treated using buprenorphine, either alone or in combination with other therapeutic agents. In some embodiments, the buprenorphine compounds and pharmaceutical compositions of the disclosure can be used to treat a Condition selected from pain and drug addiction. In addition, the buprenorphine compounds of the disclosure can be used in combination with other opioids to help mitigate adverse opioid side effects such as respiratory depression, gastrointestinal motility disorders (e.g., constipation), euphoria, and the like.

Accordingly, in some embodiments, the buprenorphine compounds of the disclosure and the pharmaceutically acceptable compositions thereof, can be used to treat or prevent acute pain or chronic pain in animals. Examples of pain that can be treated or prevented using buprenorphine include, but are not limited to, cancer pain, neuropathic pain, labor pain, myocardial infarction pain, pancreatic pain, colic pain, post-operative pain, headache pain, muscle pain, arthritic pain, and pain associated with a periodontal disease, including gingivitis and periodontitis.

In some embodiments, the buprenorphine compounds of the disclosure, and the pharmaceutically acceptable compositions thereof, can also be used for treating or preventing pain associated with inflammation or with an inflammatory disease in an animal. Such pain can arise where there is an inflammation of the body tissue which can be a local inflammatory response and/or a systemic inflammation. For example, the buprenorphine compounds can be used to treat or prevent pain associated with inflammatory diseases including, but not limited to: organ transplant rejection; reoxygenation injury resulting from organ transplantation (see Grupp et al., "Protection against Hypoxia-reoxygenation in the Absence of Poly (ADP-ribose) Synthetase in Isolated Working Hearts," *J. Mol. Cell Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory diseases of the gum, including gingivitis and periodontitis; tuberculosis; leprosy; inflammatory diseases of the kidney, including uremic complications, glomerulonephritis and nephrosis; inflammatory diseases of the skin, including sclerodermatitis, psoriasis and eczema; inflammatory diseases of the central nervous system, including chronic demyelinating diseases of the nervous system, multiple sclerosis, AIDS-related neurodegeneration and Alzheimer s disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microalbuminuria and progressive diabetic nephropathy), polyneuropathy, mononeuropathies, autonomic neuropathy, gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum); immune-complex vasculitis, and systemic lupus erythematosus (SLE); inflammatory diseases of the heart, such as cardiomyopathy, ischemic heart disease hypercholestcrolcmia, and atherosclerosis; as well as various other diseases that can have significant inflammatory components, including preeclampsia, chronic liver failure, brain and spinal cord trauma, and cancer. The buprenorphine compounds of the disclosure can also be used for inhibiting, treating, or preventing pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

The buprenorphine compounds of the disclosure, or a pharmaceutically acceptable composition thereof, can also be used to treat or prevent pain associated with nerve injury (i.e., neuropathic pain). Chronic neuropathic pain is a heterogeneous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. Chronic pain differs from acute pain in that, for chronic neuropathic pain sufferers, the abnormal pain sensations can be described as spontaneous pain, continuous superficial burning and/or deep aching pain. The pain can be evoked by heat-, cold-, and mechano-hyperalgesia, or by heat-, cold-, or mechano-allodynia.

Chronic neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain can also be caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain can result from tumor growth compression of adjacent nerves, brain, or spinal cord. In addition, cancer treatments, including chemotherapy and radiation therapy, can cause nerve injury. Neuropathic pain includes but is not limited to pain caused by nerve injury such as, for example, the pain from which diabetics suffer.

In some embodiments, the buprenorphine compounds of the disclosure and the pharmaceutical compositions thereof, can be used to treat or prevent pain associated with osteoarthritis. Osteoarthritis (OA), also known as osteoarthrosis, degenerative arthritis, or degenerative joint disease, is a group of mechanical abnormalities involving degradation of joints, including articular cartilage and subchondral bone. Examples of OA treatable or preventable using the buprenorphine compounds of the disclosure include, but are not limited to, joint pain, joint stiffness, joint tenderness, joint locking, and joint effusion.

In some embodiments, the buprenorphine compounds of the disclosure and the pharmaceutical compositions thereof, can be used to treat or prevent the Condition of drug addiction or drug abuse, particularly drug addiction to or drug abuse of another opioid. In some embodiments, the buprenorphine is administered concurrently with another opioid, where the buprenorphine, when administered in a relatively low dose, can serve to prevent, minimize, inhibit, ameliorate, or reverse the euphoria caused by the other opioid.

In some embodiments, the buprenorphine compounds of the disclosure and the pharmaceutical compositions thereof, can be used to treat or prevent the Condition of drug addiction or drug abuse of opioid agonists selected from codeine, fentanyl, heroin, hydrocodone, hydromorphone, methadone, morphine, opium, oxycodone, oxymorphone, tramadol, and mixtures of any of the foregoing.

In some embodiments, the buprenorphine compounds of the disclosure and the pharmaceutical compositions thereof, can be used in a relatively low dose to treat, ameliorate, minimize, or prevent the Condition of respiratory depression, particularly caused by other opioids, such as morphine, oxycodone, hydrocodone, hydromorphone, oxymorphone, and fentanyl, among others, as disclosed in U.S. Pat. No. 8,946,253, which is incorporated herein by reference.

In some embodiments, a buprenorphine compound of the disclosure or a pharmaceutical composition thereof, can be used in a relatively low dose to treat, ameliorate, minimize, or prevent the Condition of a gut motility disorder, such as decreased gastric motility, delayed gastric emptying, constipation, bloating and cramping. In particular, a buprenorphine compound of the disclosure or a pharmaceutical composition thereof, can be used to treat the Condition of gut motility disorders (e.g., opioid induced constipation) caused by other opioids, such as morphine, oxycodone, hydrocodone, and fentanyl.

The amount of the buprenorphine compound, or pharmaceutically acceptable composition thereof, that is effective in the treatment or prevention of any of the Conditions described herein can be determined by standard clinical techniques. The precise dose to be employed will depend on the route of administration and the seriousness of the Condition, and can be determined according to the judgment of a medical practitioner according to each animal's circumstances. Suitable effective dosage amounts, however, can, in some embodiments, range from about 0.01 mg/kg of body weight to about 2500 mg/kg of body weight. In some embodiments, the effective dosage amount ranges from about 0.01 mg/kg of body weight to about 100 mg/kg of body weight of the buprenorphine compounds; in another embodiment, about 0.02 mg/kg to about 50 mg/kg of body weight; and in another embodiment, about 0.025 mg/kg to about 20 mg/kg of body weight.

In some embodiments, an effective dosage amount is administered about every 24 h, about every 12 h, about every 8 h, about every 6 h, or about every 4 h until the Condition is abated.

In some embodiments, an oral dosage form can be formulated to administer a buprenorphine compound of the disclosure, e.g., at a dose of less than about 500 mg, less than about 400 mg, less than about 350 mg, less than about 300 mg, less than about 250 mg, less than about 200 mg, less than about 150 mg, less than about 100 mg, less than about 90 mg, less than about 80 mg, less than about 70 mg, less than about 60 mg, less than about 50 mg, less than about 40 mg, less than about 30 mg, less than about 20 mg, less than about 10 mg, less than about 9 mg, less than about 8 mg, less than about 7 mg, less than about 6 mg, less than about 5 mg, less than about 4 mg, less than about 3 mg, less than about 2 mg, less than about 1 mg, less than about 0.9 mg, less than about 0.8 mg, less than about 0.7 mg, less than about 0.6 mg, less than about 0.5 mg, less than about 0.4 mg, less than about 0.3 mg, less than about 0.2 mg or less than about 0.1 mg.

In some embodiments, the oral dosage form can be formulated to administer buprenorphine, e.g., at a dose of from about 1 mg to about 500 mg, or from about 1 mg to about 400 mg, or from about 1 mg to about 350 mg, or from about 1 mg to about 300 mg, or from about 1 mg to about 250 mg, or from about 1 mg to about 200 mg, or from about 1 mg to about 150 mg, or from about 1 mg to about 100 mg, or from about 1 mg to about 90 mg, or from about 1 mg to about 80 mg, or from about 1 mg to about 70 mg, or from about 1 mg to about 60 mg, or from about 1 mg to about 50 mg, or from about 1 mg to about 40 mg, or from about 1 mg to about 30 mg.

In some embodiments, the oral dosage form can be formulated to administer a buprenorphine compound of the disclosure, e.g., at a dose of from about 30 mg to about 500 mg, or from about 30 mg to about 400 mg, or from about 30 mg to about 350 mg, or from about 30 mg to about 300 mg, or from about 30 mg to about 250 mg, or from about 30 mg to about 200 mg, or from about 30 mg to about 150 mg, or from about 30 mg to about 100 mg, or from about 30 mg to about 90 mg, or from about 30 mg to about 80 mg, or from about 30 mg to about 70 mg, or from about 30 mg to about 60 mg, or from about 30 mg to about 50 mg, or from about 30 mg to about 40 mg.

In some embodiments, the oral dosage form can be formulated to administer a buprenorphine compound of the disclosure, e.g., at a dose of from about 0.1 mg to about 30 mg, or from about 0.2 mg to about 30 mg, or from about 0.3 mg to about 30 mg, or from about 0.4 mg to about 30 mg, or from about 0.5 mg to about 30 mg, or from about 0.6 mg to about 30 mg, or from about 0.7 mg to about 30 mg, or from about 0.8 mg to about 30 mg, or from about 0.9 mg to about 30 mg, or from about 2 mg to about 30 mg, or from about 3 mg to about 30 mg, or from about 4 mg to about 30 mg, or from about 5 mg to about 30 mg, or from about 6 mg to about 30 mg, or from about 7 mg to about 30 mg, or from about 8 mg to about 30 mg, or from about 9 mg to about 30 mg or from about 10 mg to about 30 mg.

In some embodiments, the oral dosage form can be formulated to administer a buprenorphine compound of the disclosure, e.g., at a dose of from about 3 mg to about 500 mg, or from about 3 mg to about 400 mg, or from about 3 mg to about 350 mg, or from about 3 mg to about 300 mg, or from about 3 mg to about 250 mg, or from about 3 mg to about 200 mg, or from about 3 mg to about 150 mg, or from about 3 mg to about 100 mg, or from about 3 mg to about 90 mg, or from about 3 mg to about 80 mg, or from about 3 mg to about 70 mg, or from about 3 mg to about 60 mg, or from about 3 mg to about 50 mg, or from about 3 mg to about 40 mg, or from about 3 mg to about 30 mg, or from about 3 mg to about 20 mg or from about 3 mg to about 10 mg.

In some embodiments, the oral dosage form can be formulated to administer a buprenorphine compound of the disclosure, e.g., at a dose of from about 0.1 mg to about 3 mg, or from about 0.2 mg to about 3 mg, or from about 0.3 mg to about 3 mg, or from about 0.4 mg to about 3 mg, or from about 0.5 mg to about 3 mg, or from about 0.6 mg to about 3 mg, or from about 0.7 mg to about 3 mg, or from about 0.8 mg to about 3 mg, or from about 0.9 mg to about 3 mg, or from about 1 mg to about 3 mg, or from about 2 mg to about 3 mg.

In some embodiments, the buprenorphine compounds of the disclosure are administered sublingually. A buprenorphine compound can be formulated in a sublingual formulation to provide, e.g., a dosing interval of about 4 hours, a dosing interval of about 6 hours, a dosing interval of about 8 hours, a dosing interval of about 12 hours, or a dosing interval of about 24 hours.

In some embodiments, the sublingual formulation can be formulated to administer a buprenorphine compound of the disclosure, e.g., at a dose of from about 0.001 mg to about 10 mg, or from about 0.01 mg to about 8 mg, or from about 0.05 mg to about 6 mg, or from about 0.1 mg to about 5 mg or from about 0.5 mg to about 4 mg, or from about 1 mg to about 2 mg.

In some embodiments, the buprenorphine compounds of the disclosure are administered in a transdermal system to provide, e.g., a dosing interval of about 24 hours, a dosing interval of about 3 days, or a dosing interval of about 7 days.

In some embodiments, the transdermal system can be formulated to administer buprenorphine, e.g., at a rate from about 0.001 mcg/hour to about 50 mcg/hour, or from about 0.01 mcg/hour to about 40 mcg/hour, or from about 0.05 mcg/hour to about 30 mcg/hour, or from about 0.1 mcg/hour to about 20 mcg/hour or from about 0.5 mcg/hour to about 10 mcg/hour.

In some embodiments, the transdermal system can be formulated to administer buprenorphine, e.g., at a rate from about 0.001 mcg/hour to about 5 mcg/hour, or from about 0.01 mcg/hour to about 4 mcg/hour, or from about 0.05 mcg/hour to about 3 mcg/hour, or from about 0.1 mcg/hour to about 2 mcg/hour, or from about 0.5 mcg/hour to about 1 mcg/hour.

In some embodiments, the transdermal system can be formulated to administer buprenorphine, e.g., at a rate of about 50 mcg/hour, about 40 mcg/hour, about 30 mcg/hour, about 20 mcg/hour, about 10 mcg/hour, about 5 mcg/hour, about 4 mcg/hour, about 3 mcg/hour, about 2 mcg/hour, about 1 mcg/hour, about 0.5 mcg/hour, about 0.1 mcg/hour, about 0.05 mcg/hour, about 0.01 mcg/hour, or about 0.001 mcg/hour.

In some embodiments, the buprenorphine compounds of the disclosure can be administered by any route (e.g., oral, transdermal, transmucosal, or subcutaneous) to provide at steady state, e.g., from about 0.001 mg/kg to about 1 mg/kg, or from about 0.005 mg/kg to about 0.5 mg/kg or from about 0.05 mg/kg to about 0.1 mg/kg. In other embodiments, the buprenorphine compounds can be administered by any route (e.g., oral, transdermal, transmucosal, or subcutaneous) to provide at steady state, e.g., about 1 mg/kg, about 0.5 mg/kg, about 0.1 mg/kg, about 0.05 mg/kg, about 0.005 mg/kg or about 0.001 mg/kg. Where buprenorphine is used in combination with another therapeutic agent, the buprenorphine compounds of the disclosure can be administered for any suitable time, e.g., for the full duration of therapy with the other agent, or for a fraction of the full duration of therapy with the other agent.

In some embodiments, the buprenorphine compounds of the disclosure can be administered by any route (e.g., oral, transdermal, transmucosal, or subcutaneous) to provide after first administration or at steady state, a $C_{max}$, e.g., from about 0.001 ng/mL to about 15 ng/mL, or from about 0.005 ng/mL to about 12 ng/mL, or from about 0.05 ng/mL to about 10 ng/mL, or from about 0.05 ng/mL to about 1 ng/mL, or from about 0.05 ng/mL to about 0.5 ng/mL from about 0.5 ng/mL to about 8 ng/mL, or from about 1.0 ng/mL to about 5 ng/mL, or from about 2 ng/mL to about 4 ng/mL.

In some embodiments, the buprenorphine compounds of the disclosure can be administered by any route (e.g., oral or transdermal or subcutaneous) to provide after first administration or at steady state, a $C_{max}$, e.g., of about 0.001 ng/mL, about 0.01 ng/mL, about 0.1 ng/mL, about 1 ng/mL, about 2 ng/mL, about 3 ng/mL, about 4 ng/mL, or about 5 ng/mL.

In some embodiments, the buprenorphine compounds of the disclosure can be administered by any route (e.g., oral, transdermal, transmucosal, or subcutaneous) to provide after first administration or at steady state, a $C_{max}$, e.g., of less than about 5 ng/mL, less than about 4 ng/mL, less than about 3 ng/mL, less than about 2 ng/mL, less than about 1 ng/mL, less than about 0.1 ng/mL, less than about 0.01 ng/mL, less than about 0.001 ng/mL or less than about 0.0001 ng/mL.

In some embodiments, the buprenorphine compounds of the disclosure can be administered by any route (e.g., oral, transdermal, transmucosal, or subcutaneous) to provide after first administration or at steady state, an AUC, e.g., from about 0.01 ng/mL per hour to about 100 ng/mL per hour, or from about 0.1 ng/mL per hour to about 75 ng/mL per hour, or from about 1.0 ng/mL per hour to about 50 ng/mL per hour, or from about 5.0 ng/mL per hour to about 40 ng/mL per hour, or from about 10 ng/mL per hour to about 30 ng/mL per hour.

In some embodiments, the steady state or first administration AUC and $C_{max}$ values disclosed herein can be obtained by any suitable route of administration such as transdermal, transmucosal, sublingual, buccal, oral, subcutaneous, intramuscular, or parenteral. A depot injection of buprenorphine may be administered by implantation (for example, subcutaneously or intramuscularly) or by intramuscular injection. In such formulations, the release of the buprenorphine can be controlled by formulation with a suitable polymeric or hydrophobic material (e.g., polylactic glycolic acid), an ion exchange resin, or from a sparingly soluble derivative (e.g., a sparingly soluble salt). In some embodiments, the depot injection provides a dosing interval from about 1 day to about 3 months, or about 3 days, about 7 days, about 10 days, about 14 days, about 21 days, about one month, about 6 weeks, or about 2 months.

In some embodiments, the methods for treating or preventing a Condition in an animal in need thereof can further comprise co-administering to the animal being administered the buprenorphine compounds or compositions of the disclosure (i.e., a first therapeutic agent) a second therapeutic agent. In some embodiments, the second therapeutic agent is administered in an effective amount.

A composition of the disclosure is prepared by a method comprising admixing a buprenorphine compound of the disclosure or a pharmaceutically acceptable salt or solvate thereof with a pharmaceutically acceptable carrier or excipient. Admixing can be accomplished using methods known for admixing a compound and a pharmaceutically acceptable carrier or excipient. In one embodiment, the buprenorphine prepared from an acetate salt is present in the composition in an effective amount.

Throughout the disclosure when the wt % of buprenorphine free base, an acetate salt of buprenorphine, a hydrate of buprenorphine acetate, buprenorphine acetate tetrahydrate, and/or various impurities is referred to, the wt % is determined via HPLC purity, for example, by the method of Example 7 set forth herein.

The following examples are set forth to assist in understanding the invention and should not be construed as specifically limiting the invention described and claimed herein. Such variations of the invention, including the substitution of all equivalents now known or later developed, that would be within the purview of those skilled in the art, and changes in formulation or changes in experimental design, are to be considered to fall within the scope of the invention incorporated herein.

5. EXAMPLES

Various features and embodiments of the disclosure are illustrated in the following representative examples, which are intended to be illustrative, and not limiting.

Example 1: Acid Screening Experiments with Buprenorphine Free Base

Buprenorphine free base can be thought of as an organic amine/phenol, which can be treated with acid or base to form its corresponding ammonium salt or phenolate salt. It is potentially advantageous to form such a salt for purification purposes due to differences in physical attributes (e.g., solubility) between the salts of the product and the impurities of interest. The purified salt can then be treated with base (or acid for the phenolate) to regenerate the desired buprenorphine free base.

Purification of buprenorphine via the hydrochloride salt. Conversion of buprenorphine free base to its hydrochloride salt, and back to the free base was explored. No significant purge of the compound of formula (12) or the compound of formula (14) was observed under any of the conditions explored.

To further expand the study of purification of buprenorphine free base via salt formation, other acids were explored. These included acetic acid, formic acid, trifluoroacetic acid, phosphoric acid, tartaric acid, toluenesulfonic acid, propionic acid, and methane sulfonic acid. For the screening of these other acids, removal of only the impurity compound of formula (12) was studied.

Procedure for Acid Screening Experiments. In a 20 mL scintillation vial, buprenorphine free base (1.0 g) was dissolved or suspended in either water, an organic solvent, or a mixed organic and aqueous solvent followed by addition of acid. If necessary to achieve dissolution, the mixture was heated on a pie-block heating system up to 80° C. and allowed to cool slowly to a temperature of about 25° C. If crystalline material, i.e., a buprenorphine salt, was observed, the solids were filtered, washed with water, and dried under sub-atmospheric pressure in an oven at 80° C. for about 16 hours and the % recovery relative to the original 1.0 g buprenorphine free base charge was determined. Table 3 summarizes the results. For the acids that are solids at a temperature of about 20° C., i.e., tartaric acid and toluenesulfonic acid hydrate, the mass of acid used is provided instead of the acid volume.

TABLE 3

Acid Screening Experiments with Buprenorphine Free Base

| Acid | Solvent | Final Acid:Solvent Composition (mL:mL) | % Recovery | Observations |
|---|---|---|---|---|
| Acetic Acid | Water | 2.5:15 | 80 | Crystals formed |
| Acetic Acid | Water | 4:24 | 74 | First repeat experiment, crystals formed |
| Acetic Acid | Water | 4:24 | 82 | Second repeat experiment, crystals formed |
| Acetic Acid | Water | 4:24 | 78 | Third repeat experiment, crystals formed |
| Trifluoroacetic Acid | Water | 2:2 | — | No crystallization, oil formed at 25° C. |
| Phosphoric Acid (85%) | Water | 1:3 | — | No crystallization on cooling, remained in solution at 25° C. |
| Tartaric Acid (0.32 g) | Water and IPA | (1:4 Water:IPA) | — | No crystallization |
| p-Toluenesulfonic Acid Hydrate (0.41 g) | Water and IPA | (1:4 Water:IPA) | — | No crystallization, hazy solution |
| Sulfuric Acid | Water | 1:3 | — | No dissolution, decomposed at 0° C.-65° C. |
| Formic Acid | IPA | 1:5 | — | No crystallization |
| Formic Acid | Water | 3:12 | 61 | Crystals formed |
| Propionic Acid | Water | 3:12 | — | No crystallization, oil formed |
| Methanesulfonic Acid | Water | 4:4 | — | No crystallization |
| Methanesulfonic Acid (1 mL) | Water and IPA | 1:(1:6 Water:IPA) | — | No crystallization |

Acetic acid or formic acid resulted in the formation of crystals; addition of the other acids failed to form filterable salts. However, in order to achieve crystallization of the buprenorphine salt when using either acetic acid or formic acid, it was discovered that the volume of water used should be about the same as the volume of acid used to facilitate dissolution of the buprenorphine free base. Thereafter, the addition of a greater quantity of water brought about crystallization of a buprenorphine salt. For example, for the addition of acetic acid in Table 3 above that achieved 80% recovery, initially 2.5 mL of acetic acid and 2.5 mL of water were added so that the buprenorphine free base could dissolve. Thereafter, at a temperature of about 25° C., adding an additional 12.5 mL of water brought about crystallization of the buprenorphine acetate salt.

In addition, only the two aqueous mixtures containing either acetic acid or formic acid offered a promising purge of the impurity of the compound of formula (12) (up to 40%). Recovery of the corresponding salt of buprenorphine was higher from aqueous mixtures of acetic acid (78.5%, average of four determinations) than from formic acid (61%). In both cases, the corresponding salt of buprenorphine was isolated as a crystalline solid. The other acids provided the corresponding salts of buprenorphine, if any, as an oil or gum which was not amendable to isolation via filtration. Interestingly, it was discovered that the solids isolated from acetic acid:water yielded buprenorphine free base upon drying under sub-atmospheric pressure at elevated temperature (e.g., 85° C.). Without being bound by theory, this discovery was believed to suggest a somewhat weak association between acetic acid and buprenorphine and the phenomenon was developed into an advantageous isolation of buprenorphine free base by a purification process involving aqueous acetic acid (see, e.g., Examples 2 and 8 below). Repeated acid screening determinations for the acetic acid:water solvent system confirmed that crystallization from acetic acid:water led to an advantageous increased purging of the compound of formula (12).

Example 2: Preparation of Buprenorphine Acetate Salt

For preparing the buprenorphine acetate salt, buprenorphine free base (100 gm, 214 mmol) was dissolved in 1:1 acetic acid:water (vol:vol, 370 mL). The temperature during addition of the acetic acid-water solution was maintained at 60° C. Still at 60° C., the mixture was then polish filtered, i.e., filtered to remove non-product related insoluble impurities (e.g., dust). The dissolution equipment was then rinsed with 0.4 volumes of 51 wt % acetic acid in water and the rinse and the filtrate were combined.

Crystallization: At 60° C., about 0.75 volumes (75 mL) of water (anti-solvent) were added to the combined filtrate at a rate of 8 mL/min. The resulting admixture was seeded with 0.5 g of buprenorphine acetate salt crystals. The solution was held at 60° C. for 0.5 hrs, and then about 5.9 volumes (588 mL) of water (anti-solvent) were added at a rate of about 15 mL/min. at a temperature of 60° C. Thereafter, about 0.9 volumes (88 mL) of IPA at a temperature of 60° C. were added and the mixture was cooled at a rate of 8° C./hour to 20° C. to provide a precipitate.

Isolation of Buprenorphine Acetate: The precipitate from the crystallization step was filtered and washed with 2.5 volumes of 17 wt % IPA in water. The precipitate was then washed a second time with 17 wt % IPA in water at 20° C.

Example 3: Buprenorphine Acetate Tetrahydrate Crystal Structure by Single Crystal X-Ray Analysis A colorless, prismatic single crystal of $[C_{29}H_{42}NO_4]^+$ $[CH_3COO]^-\cdot 4H_2O$ with the approximate dimensions of 0.24 mm×0.10 mm×0.05 mm, obtained by a method substantially equivalent to that of Example 2 but modified to facilitate the growth of dimensionally-larger crystals, was mounted on a MICROMOUNT and centered on a R-AXIS RAPID X-ray diffractometer (Rigaku Americas, Woodlands, Tex.).

Diffraction data were acquired at a temperature of about 25° C. on the above diffractometer equipped with a sealed tube copper source ($\lambda$=1.54187 Å) and a Spider curved image plate detector. Four frames separated in reciprocal space were recorded to provide an orientation matrix and initial cell parameters. Final cell parameters were obtained and refined based on the full data set. A diffraction data set of reciprocal space was obtained to a resolution of 0.81 Å using 5° oscillation steps and 300 s exposure for each frame. Integration of intensities and refinement of cell parameters were accomplished using CRYSTALCLEAR software. Observation of the crystal after data collection and the appearance of diffraction rings on the recorded images indicated that the crystal underwent slow decomposition during the diffraction experiment.

The structure was solved using OLEX2 (Dolmanov et al., "Olex2: a complete structure solution, refinement and analysis program," *J Appl Cryst*. 42:339-341 (2009)) with the OLEX2.SOLVE structure solution program (Puschmann et al., "[MS45-P09] Olex2—a complete package for molecular crystallography," *Acta Cryst*. A69:s679 (2013)) with charge flipping method, and refined with the OLEX2.REFINE refinement package (Bourhis et al., "The anatomy of a comprehensive constrained, restrained refinement program for the modern computing environment—Olex2 dissected," *Acta Cryst*. A71:1-17 (2014)) using Gauss-Newton full matrix minimization.

Based on systemic absences and intensities statistics, the structure was solved and refined in a non-centrosymmetric monoclinic $P2_1$ space group. Non-hydrogen atoms were found by the charge flipping method used for solving the structure and were refined using anisotropic atomic displacement parameters. The hydrogen atoms were placed in calculated positions and were refined with isotropic atomic displacement parameters. The structure had two cations of buprenorphine and two acetic acid anions as well as eight water molecules in the unit cell making one cation of buprenorphine, one acetic acid anion, and four water molecules symmetry independent.

Packing of the molecules in the crystal was determined by strong Coulombic interaction between the buprenorphonium cation and acetic acid anion well as nine distinct hydrogen bonds ("HB") between the buprenorphonium cation, acetic acid anion, and water molecules.

Three strong HBs were present in the structure. One HB, denoted by "A" in FIG. 1, was an intramolecular hydrogen bond between the aliphatic hydroxyl group (containing the oxygen atom labeled as "O23" in FIG. 3) and the oxygen atom of the methoxy group of the buprenorphine (labeled as "O21" in FIG. 3); the intramolecular HB length was 2.569 Å. Another HB, denoted by "B" in FIG. 1, was an intermolecular HB formed between the hydrogen of the nitrogen cation of the buprenorphine (HB donor, labeled as "N1" in FIG. 3) and one of the oxygen atoms of the acetic acid anion (HB acceptor, labeled as "O42B" in FIG. 3); the intermolecular HB length was 2.681 Å. The third HB, denoted by "C" in FIG. 1, was another intermolecular HB between a water molecule oxygen (labeled as "O1" in FIG. 3) and the phenol group (HB donor, containing the oxygen atom labeled as "O11" in FIG. 3). The length of this bond was 2.591 Å, indicating a strong interaction.

The acetic acid anion was also involved in formation of other HBs to adjacent water molecules. The HB distances of these three interactions were 2.735 Å (acetic acid anion to the water molecule containing O1), 2.743 Å (also to the water molecule containing O1 from another water molecule), and 2.778 Å (acetic acid anion to a hydrogen of the water molecule containing the oxygen atom labeled as "O4" in FIG. 3).

The aliphatic hydroxyl group of the buprenorphine acted as a HB acceptor as well, forming a HB, denoted by "D" in FIG. 1, with an adjacent water molecule (containing O4) acting as a HB donor. The HB length of this interaction was 2.802 Å, significantly longer than for the intramolecular hydrogen bond A.

The phenol group was also involved in formation of two intramolecular hydrogen bonds—both with adjacent water molecules. One of the two hydrogen bonds, the HB with oxygen atom O1 previously identified as "C" in FIG. 1, was significantly shorter (2.591 Å) and therefore stronger than the HB formed with oxygen atom labeled as "O2" in FIG. 3 (3.007 Å).

All four water molecules were involved in formation of different hydrogen bonds; three of them were saturated, i.e., each formed three HBs—two as a donor and one as an acceptor. One water molecule (containing the oxygen atom labeled as "O3" in FIG. 3) was involved in formation of only one HB (with another water molecule containing O2). Without being bound by theory, it is believed that the O3-containing water molecule would be most susceptible to leaving the crystal lattice during a dehydration process, that water molecule being the most loosely bound of the four water molecules.

Water molecule 1 (containing O1) formed two HBs with two acetic acid anions and accepted a HB from the phenolic hydroxyl group of the buprenorphine. Water molecule 2 (containing O2) formed two HBs with two other water molecules and one as a donor with the phenolic hydroxyl group. Water molecule 3 (containing O3) formed only one HB as a donor with another water molecule (containing O2). Water molecule 4 (containing O4) formed one hydrogen bond with the acetic acid anion, one with the aliphatic hydroxyl group of the buprenorphine, and accepted HB from another water molecule (containing O2).

The density of the crystalline phase at a temperature of about 25° C. was calculated to be 1.2535 g/cm$^3$.

Figure 2:
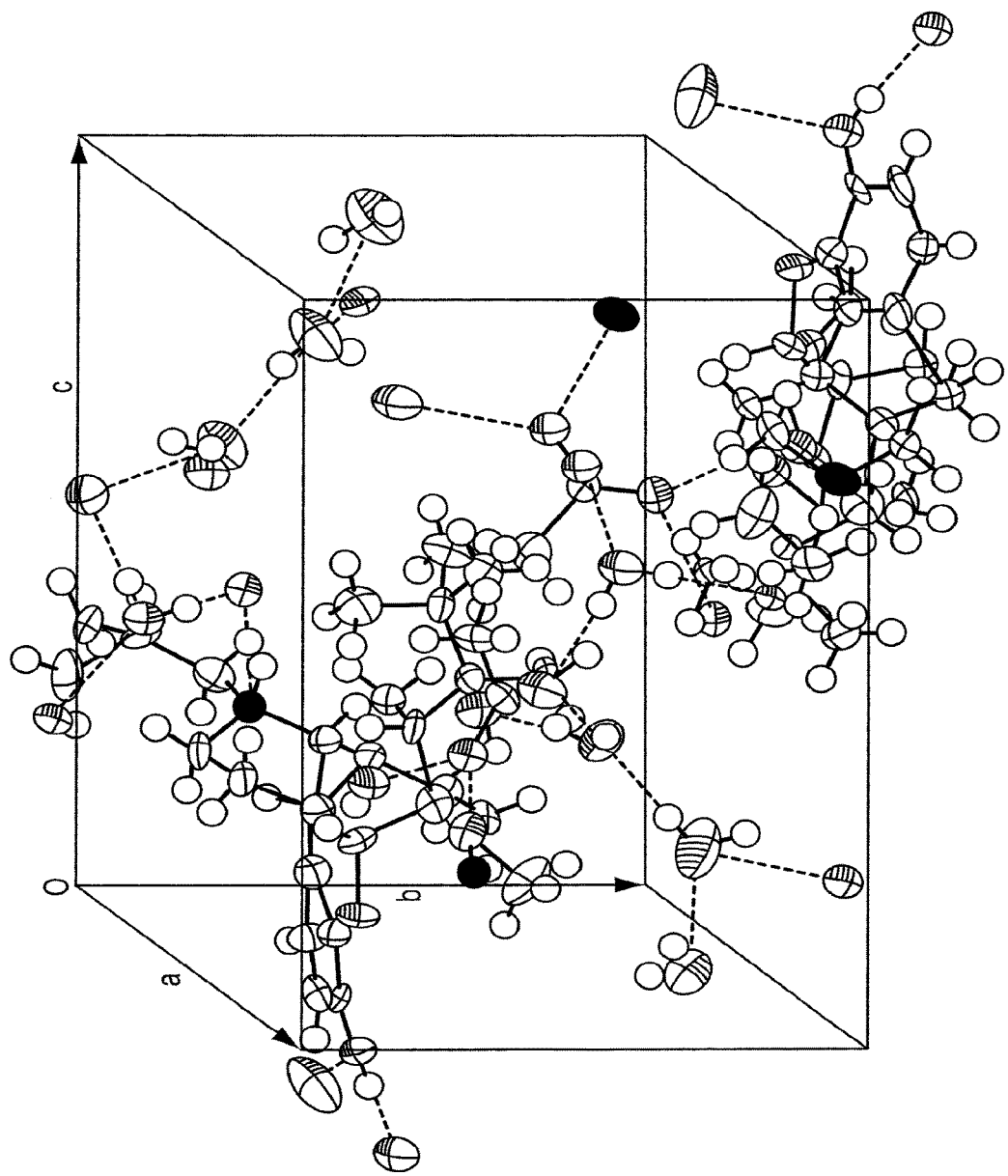
FIG. 2 shows a packing diagram of buprenorphine acetate tetrahydrate within the unit cell.

Table 4 summarizes some of the single crystal X-ray analysis determinations for buprenorphine acetate tetrahydrate. FIG. 2 shows a packing diagram of buprenorphine acetate tetrahydrate within the unit cell.

TABLE 4[1]

| Empirical formula (Buprenorphine Free Base Empirical formula) | $C_{31}H_{53}NO_{10}$ ($C_{29}H_{41}NO_4$) |
|---|---|
| Formula Weight (Buprenorphine Free Base Formula Weight) | 599.76 g/mol (467.64 g/mol) |
| Crystal System | Monoclinic |
| Space Group | P2$_1$ |
| a | 10.5190 Å [4] |
| b | 10.9258 Å [4] |
| c | 14.4421 Å [10] |
| α | 90° |
| β | 106.812° [8] |
| γ | 90° |
| Volume | 1588.87 Å$^3$ [15] |
| Z | 2 |
| μ | 0.760 mm$^{-1}$ |
| F(000) | 654.2 |
| Radiation | Cu Kα (λ = 1.54187 Å) |
| 2Θ range for data collection | 6.4° to 143.42° |

TABLE 4[1]-continued

| Index ranges | $-10 \le h \le 12$ |
|---|---|
|  | $-13 \le k \le 13$ |
|  | $-17 \le l \le 17$ |
| Reflections collected | 22679 |
| Independent reflections | 5921 {R$_{int}$ = 0.0674, R$_{sigma}$ = 0.1220} |
| Data/restraints/parameters | 5921/0/398 |
| Goodness-of-fit on F$^2$ | 1.002 |
| Final R indexes {I ≥ 2σ (I)} | R$_1$ = 0.0880 wR$_2$ = 0.2120 |
| Final R indexes {all data} | R$_1$ = 0.1595 wR$_2$ = 0.2925 |
| Largest diff. peak/hole | 0.48 e Å$^{-3}$/−0.50 e Å$^{-3}$ |
| Flack parameter | −0.0 [4] |

[1]Each number within square brackets is the estimated standard deviation ("ESD") of the final digit of the reported value. For example, for the reported unit cell parameter a-axis length of 10.5190 Å, the ESD is ± 0.0004 Å.

Figure 3:
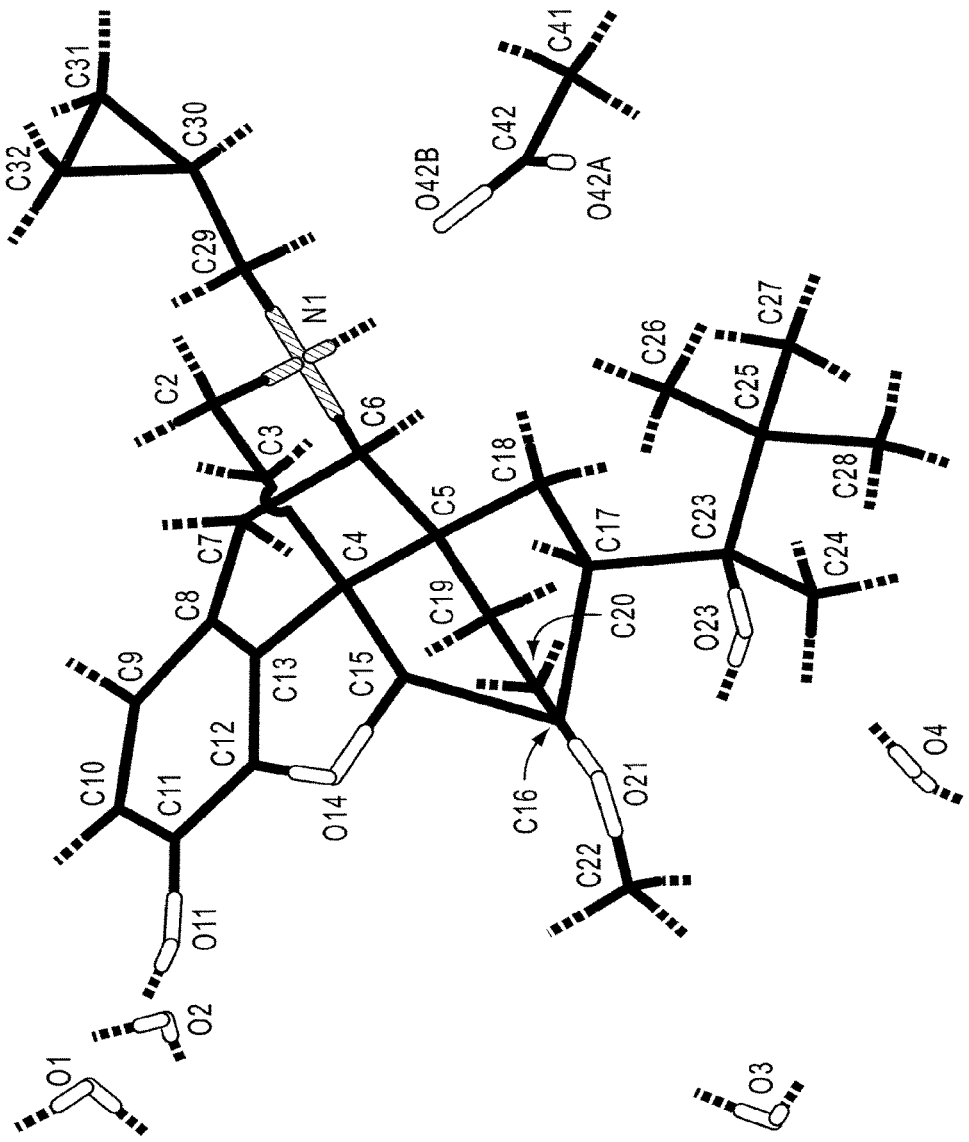
FIG. 3 shows a stick representation of the components of the buprenorphine acetate tetrahydrate crystal including the atom numbering scheme used.

The single crystal of buprenorphine acetate tetrahydrate analyzed had the fractional atomic coordinates (×10$^4$) and equivalent isotropic displacement parameters (Å$^2$×10$^3$) set forth in Table 5. FIG. 3 shows a stick representation of the components of the buprenorphine acetate tetrahydrate crystal including the atom numbering scheme used in Table 5.

TABLE 5[1]

| Atom | x | y | z | U (eq.) |
|---|---|---|---|---|
| C2 | −11486 [7] | −7262 [6] | −8543 [5] | 43.4 [18] |
| C3 | −10066 [7] | −7107 [7] | −8580 [5] | 45.1 [19] |
| C4 | −9781 [7] | −5849 [6] | −8948 [4] | 37.6 [17] |
| C5 | −10116 [7] | −4823 [6] | −8322 [5] | 39.5 [17] |
| C6 | −11604 [7] | −5009 [7] | −8404 [4] | 40.3 [17] |
| C7 | −12513 [7] | −4872 [6] | −9458 [4] | 42.1 [18] |
| C8 | −11892 [7] | −5216 [6] | −10244 [5] | 39.5 [17] |
| C9 | −12434 [8] | −4973 [7] | −11209 [5] | 46.8 [19] |
| C10 | −11668 [7] | −5073 [7] | −11865 [5] | 57 [2] |
| C11 | −10333 [8] | −5303 [6] | −11539 [5] | 39.3 [17] |
| C12 | −9791 [7] | −5532 [6] | −10571 [5] | 37.6 [16] |
| C13 | −10587 [7] | −5597 [6] | −9966 [4] | 37.4 [16] |
| C15 | −8345 [7] | −5742 [7] | −9030 [4] | 39.3 [18] |
| C16 | −7708 [7] | −4620 [7] | −8422 [5] | 43.8 [18] |
| C17 | −7651 [7] | −5006 [6] | −7370 [4] | 38.6 [16] |
| C18 | −9111 [7] | −4865 [7] | −7290 [5] | 46.3 [19] |
| C19 | −9930 [7] | −3581 [7] | −8719 [5] | 44.2 [19] |
| C20 | −8502 [8] | −3492 [7] | −8790 [5] | 48 [2] |
| C22 | −5979 [10] | −3712 [9] | −9069 [7] | 84 [3] |
| C23 | −6568 [8] | −4426 [7] | −6512 [5] | 48 [2] |
| C24 | −6608 [9] | −3032 [7] | −6492 [6] | 58 [2] |
| C25 | −6513 [8] | −5000 [7] | −5492 [5] | 49 [2] |
| C26 | −6655 [9] | −6384 [8] | −5559 [6] | 65 [3] |
| C27 | −7523 [9] | −4455 [9] | −5026 [6] | 66 [3] |
| C28 | −5097 [9] | −4800 [9] | −4793 [6] | 68 [3] |
| C29 | −13208 [8] | −6380 [8] | −7886 [6] | 58 [2] |
| C30 | −13484 [9] | −7552 [9] | −7434 [5] | 61 [3] |
| C31 | −14891 [9] | −7909 [7] | −7589 [6] | 57 [2] |
| C32 | −14048 [10] | −8593 [9] | −8062 [8] | 78 [3] |
| N1 | −11820 [6] | −6237 [5] | −7983 [4] | 42.3 [15] |
| O11 | −9523 [6] | −5289 [5] | −12126 [3] | 54.6 [14] |
| O14 | −8470 [5] | −5666 [5] | −10054 [3] | 41.0 [12] |
| O21 | −6344 [5] | −4584 [5] | −8494 [4] | 53.0 [14] |
| O23 | −5299 [5] | −4806 [6] | −6660 [4] | 61.9 [16] |
| C41 | −9924 [9] | −6962 [9] | −4473 [5] | 63 [3] |
| C42 | −10551 [8] | −6292 [8] | −5431 [5] | 46.5 [19] |
| O42A | −11102 [6] | −5299 [5] | −5449 [4] | 67.4 [17] |
| O42B | −10479 [5] | −6879 [5] | −6172 [3] | 47.6 [13] |
| O4 | −2900 [6] | −3593 [6] | −6509 [5] | 74.5 [18] |
| O2 | −7198 [10] | −6922 [8] | −12061 [6] | 116 [3] |
| O3 | −4259 [8] | −1514 [8] | −9832 [7] | 111 [3] |
| O1 | −10640 [8] | −4111 [5] | −13710 [4] | 74.9 [19] |

[1]Each number within square brackets is the ESD of the final digit of the reported value.

Example 4: Buprenorphine Acetate Tetrahydrate Structure by X-Ray Powder Diffraction To further characterize the crystalline form of buprenorphine acetate tetrahydrate, the powdered compound was analyzed by X-ray diffraction. A representative XRPD pattern obtained from a buprenorphine acetate tetrahydrate sample using CuKα radiation yielded peaks at the diffraction angles (°2θ±0.2°) provided in Table 1 above and is shown in FIG. 4.

The XRPD pattern was collected with an X'Pert PRO MPD diffractometer (PANalytical Inc., Westborough, Mass.) using an incident beam of Cu radiation produced using an OPTIX long, fine-focus source. An elliptically graded multilayer mirror was used to focus CuKα X-rays through the specimen and onto the detector. Prior to the analysis, a silicon specimen (National Institute of Standards and Technology ("NIST") Standard Reference Material 640d, Gaithersburg, Md.) was analyzed to verify that the observed position of the Si 111 peak was consistent with the NIST-certified position. A specimen of the sample was sandwiched between 3 μm thick films and analyzed in transmission geometry. A beam-stop, short anti-scatter extension, and an anti-scatter knife edge were used to minimize the background generated by air. Soller slits for the incident and diffracted beams were used to minimize broadening from axial divergence. The diffraction pattern was collected using a X'Celerator scanning position-sensitive detector (PANalytical Inc.) located 240 mm from the specimen and X'Pert Data Collector software version 2.2b.

Example 5: Differential Scanning Calorimetric Analysis of Buprenorphine Acetate Tetrahydrate To further characterize buprenorphine acetate tetrahydrate, the compound was analyzed by differential scanning calorimetry ("DSC"). A representative DSC curve for a buprenorphine acetate tetrahydrate sample is shown in FIG. 5.

The DSC of the buprenorphine acetate tetrahydrate samples, presented as heat flow (W/g) vs. temperature (° C.), had two transition regions. The first transition region was from about 50° C. to about 180° C. The peak or peaks in this region were broad with one or more minima and likely represented the loss of water and/or acetic acid from the material sample being analyzed. The second transition region was from about 210° C. to about 225° C. This region featured a sharp transition that was likely representative of the melting of buprenorphine base. This sharp transition was also present at about the same peak temperature in the DSC of the free base form of buprenorphine.

Figure 6:
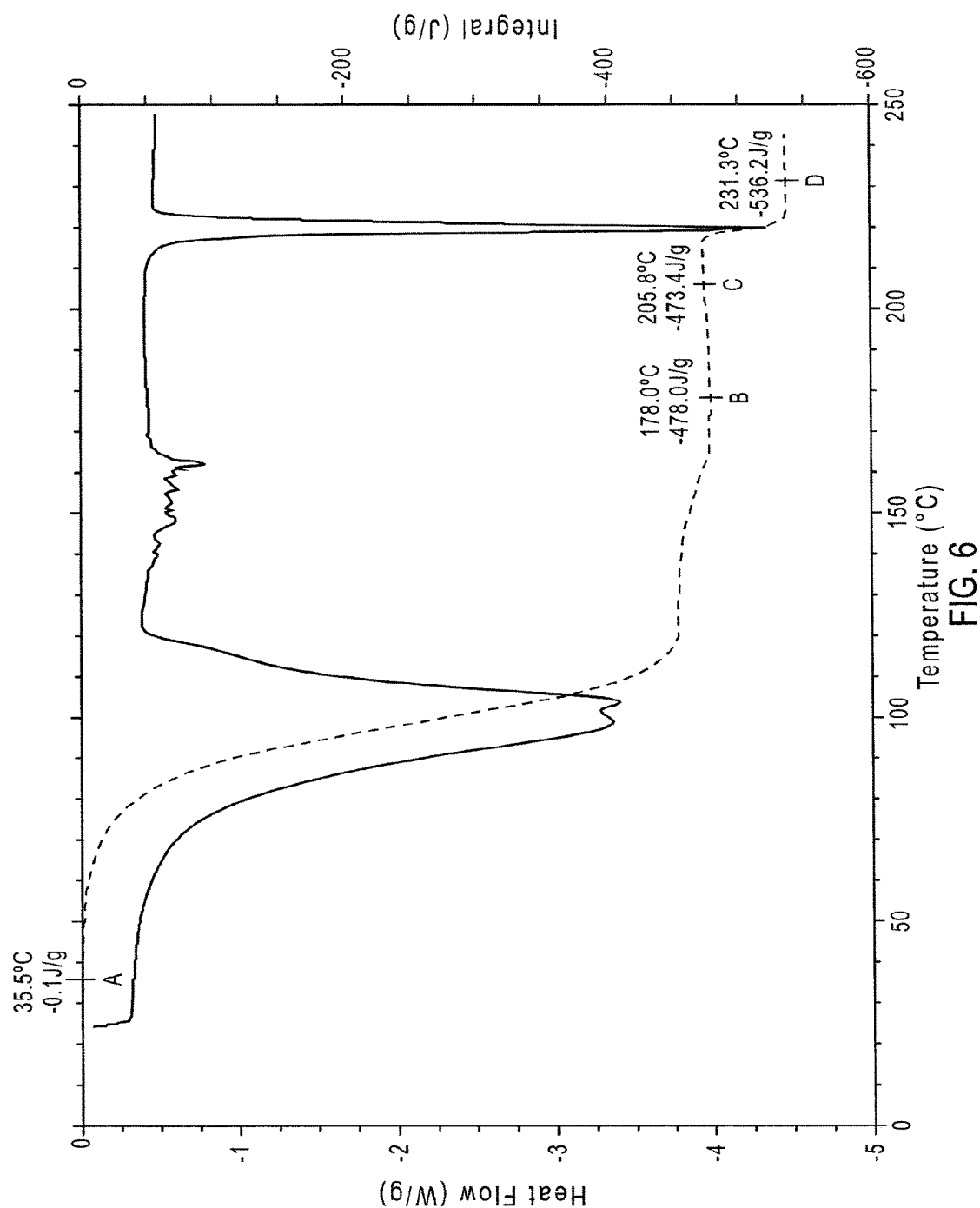
FIG. 6 shows an integral ratio determination of transition regions in a differential scanning calorimetry scan of buprenorphine acetate tetrahydrate.

Several samples of buprenorphine acetate tetrahydrate of varying sizes were analyzed for consistency between different sample sizes. DSC analysis was performed using a linear heating ramp of 10° C./minute to 250° C. The measurements were determined with a Q20 DSC apparatus (TA Instruments, New Castle, Del.). The integrals (area under the curve) of the transition regions (Region 1/Region 2) were determined by TA Instruments Universal Analysis 2000 software (version 4.5A, build 4.5.0.5) over the temperature range of from about 35° C. to about 180° C. for the first transition region and from about 203° C. to 233° C. for the second transition region. The integral ratios of the transition regions are shown in Table 6 below. A representative DSC profile, for Lot 2 discussed below, is shown in FIG. 6. As can be noted from FIG. 6, for this determination Region 1 extended from point "A" at about 35.5° C. to point "B" at about 178° C. and Region 2 extended from point "C" at about 206° C. to point "D" at about 231° C.

TABLE 6

Integral Ratios of Buprenorphine Acetate Tetrahydrate DSC Regions

| Sample Size (mg) | Region 1 Integral (J/g) | Region 2 Integral (J/g) | Ratio (Region 1/Region2) |
|---|---|---|---|
| 2.9 | −441.8 | −57.5 | 7.68 |
| 6.4 | −460.5 | −62.5 | 7.37 |
| 6.9 | −477.9 | −62.8 | 7.61 |
| 13.7 | −451.3 | −61.7 | 7.31 |

To test for consistency of this integral ratio between buprenorphine acetate tetrahydrate samples, several different sample lots were analyzed. DSC analysis was performed using a linear heating ramp of 10° C./minute to 250° C. The results are shown in Table 7.

TABLE 7

Integral Ratios of Buprenorphine Acetate Tetrahydrate DSC Regions, Varying Lots

| Lot Number (mg) | Region 1 Integral (J/g) | Region 2 Integral (J/g) | Ratio (Region 1/Region2) |
|---|---|---|---|
| Lot 1 (5.4) | −462.3 | −63.1 | 7.33 |
| Lot 2 (6.9) | −477.9 | −62.8 | 7.61 |
| Lot 3 (6.2) | −450.6 | −63.0 | 7.15 |
| Lot 4 (6.4) | −458.1 | −64.3 | 7.12 |
| Lot 5 (6.9) | −466.0 | −63.5 | 7.34 |
| Lot 6 (7.9) | −473.4 | −65.5 | 7.23 |

The integral ratios of the two regions were similar across a range of sample sizes. The integral ratios of the two regions were similar across a number of samples of buprenorphine acetate. The approximate integral ratio of Region 1/Region 2 for the buprenorphine acetate tetrahydrate samples was from 7.0 to about 8.0. In another embodiment, the approximate integral ratio of Region 1/Region 2 for a buprenorphine acetate tetrahydrate sample is from 7.1 to about 7.9. In another embodiment, the approximate integral ratio of Region 1/Region 2 for a buprenorphine acetate tetrahydrate sample is from 7.1 to about 7.7.

Example 6: Buprenorphine Acetate Tetrahydrate Karl Fischer % Water Analysis

Thirteen samples of buprenorphine acetate tetrahydrate were measured for their water content by Karl Fischer ("KF") titration analysis. KF analysis methodologies are known in the art, for example, see ASTM Standard E203-O8 ("Standard Test Method for Water Using Volumetric Karl Fischer Titration") and ISO 760:1978 ("Determination of Water—Karl Fischer Method"). A compilation of the KF values for various samples of buprenorphine acetate tetrahydrate are tabulated below. The table represents a number of samples generated from a variety of crystallization conditions and dried at a temperature of about 25° C. and a pressure of about 1 atm to a constant weight. The KF titrations were carried out using a 915 KF Ti-Touch apparatus (Metrohm USA Inc., Riverview, Fla.) with HYDRANAL Composite 5 Karl Fischer reagent (Sigma-Aldrich, St. Louis, Mo.). The results are shown in Table 8 below. The mean of the thirteen determinations is also provided in Table 8 along with the theoretical weight percent of water (12.02 wt %) calculated for the tetrahydrate of buprenorphine acetate.

TABLE 8

| Sample No. | KF Determination (Wt % Water) |
| --- | --- |
| 1 | 12.52 |
| 2 | 11.80 |
| 3 | 11.83 |
| 4 | 11.84 |
| 5 | 12.47 |
| 6 | 12.39 |
| 7 | 12.76 |
| 8 | 12.94 |
| 9 | 12.28 |
| 10 | 12.50 |
| 11 | 11.98 |
| 12 | 12.02 |
| 13 | 12.18 |
| Mean | 12.27 |
| Theoretical | 12.02 |

The mean value of wt % water for the 13 different buprenorphine acetate hydrate samples tested differed from this theoretical value by only 0.25 wt % water or by only about 2.1%.

Example 7: HPLC Analysis Procedure

A Waters 2695 HPLC (Waters Corp., Milford, Mass.) with a reversed-phase 100 mm×3.0 mm inner diameter GEMINI NX-C18 column, 3.0 μm particle size (Phenomenex, Torrance, Calif.) was used. The detection wavelength was 240 nm. A gradient mobile phase utilized 20 mM aqueous ammonium bicarbonate at pH 9.0 ("MPA", 99.5%, Fluka, St. Louis, Mo.) as mobile phase A and acetonitrile ("MPB", 99.9%, Sigma-Aldrich, St. Louis, Mo.) as mobile phase B according to the gradient profile provided in Table 9.

TABLE 9

| Step | Time from Injection (min.) | Volume % MPA | Volume % MPB |
| --- | --- | --- | --- |
| 1 | 0.00 | 80.0 | 20.0 |
| 2 | 6.00 | 50.0 | 50.0 |
| 3 | 22.00 | 40.0 | 60.0 |
| 4 | 35.00 | 10.0 | 90.0 |
| 5 | 40.10 | 80.0 | 20.0 |

The column temperature was 40° C., the injection volume was 15 μL, and the flow rate was 1.0 mL/min. Analysis concluded at about 45 minutes after each injection.

Each buprenorphine acetate tetrahydrate sample was prepared for HPLC analysis as follows. In duplicate, 100.0±2.0 mg of sample was weighed, the weight was recorded ($W_S$ is the weight of each sample), and the sample was quantitatively transferred into a 100 mL volumetric flask. About 50 mL of methanol (99.9%, Fisher Scientific, Pittsburgh, Pa.) was added to the flask and the admixture was sonicated and/or vortex mixed as required until all solids appeared to be dissolved. Thereafter, additional methanol was added to the mark and the solution was mixed well.

Standard solutions were prepared as follows. A working standard solution was prepared by weighing 27.0±1.0 mg of USP buprenorphine hydrochloride CIII reference standard (#1078700, USP, Rockville, Md.) of known purity, recording the weight ($W_{STD}$ is the weight of the USP standard corrected for purity), and quantitatively transferring it into a 25 mL volumetric flask. About 15 mL of methanol was added to the flask and the admixture was sonicated and/or vortex mixed as required until all solids appeared to be dissolved. Thereafter, additional methanol was added to the mark and the solution was mixed well. The working standard solution contained the equivalent of 1.0 mg/mL of buprenorphine free base. The working standard was used to verify that, inter alia, the retention time, tailing factor, and repeatability of the buprenorphine peak was acceptable. An intermediate standard solution was prepared by pipetting 2.5 mL of working standard solution into a 50 mL volumetric flask, diluting to volume with methanol, and mixing well. The intermediate standard solution contained the equivalent of 0.05 mg/mL of buprenorphine free base. A sensitivity standard solution was prepared by pipetting 1.0 mL of intermediate standard solution into a 100 mL volumetric flask, diluting to volume with methanol, and mixing well. The sensitivity standard solution contained the equivalent of 0.0005 mg/mL of buprenorphine free base. The sensitivity standard was used to verify that the HPLC signal/noise ratio was not less than 10.

A system suitability standard was prepared as follows. To a container of the European Pharmacopoeia reference standard "buprenorphine for system suitability" containing 10 mg of material (# Y0001122, European Directorate for the Quality of Medicines & Health Care, Strasbourg, France) was added about 2 mL of methanol. The container was capped, shaken and inverted several times so as to rinse it and dissolve all solids, and the solution was transferred into a 10 mL volumetric flask. This dissolution procedure was repeated twice more. The about 6 mL of solution was sonicated for about 5 min. to insure dissolution of all solids, cooled to a temperature of about 25° C., diluted to volume with methanol, and mixed well. The system suitability standard solution contained 1.0 mg/mL of buprenorphine free base along with a known profile of impurities (see European Pharmacopoeia monographs 1180, 1181). The system suitability standard was used to verify that the required resolution between impurity peaks and the buprenorphine peak was achieved.

The HPLC column was cleaned and flushed as required and then equilibrated with 80:20 MPA:MPB for 30 minutes at 40° C. and at a flow rate of 1.0 mL/min. Thereafter, the injection sequence in Table 10 was followed.

TABLE 10

| Analyte | Number of Injections |
| --- | --- |
| Methanol (blank) | At least 2 |
| Sensitivity Standard | 1 |
| System Suitability Standard | 1 |
| Working Standard | 5 (for repeatability, final 2 injections for quantitation) |
| Methanol (blank) | 1 |
| Sample (bracket up to 6) | 1 |
| Working Standard | 2 |
| Methanol (blank) | 1 |

For each sample peak, the corresponding peak area was determined by the instrument software to provide the quantity $A_S$. The total peak area, $A_{TOTAL}$, was determined by summing the areas of all the peaks, again by the instrument software. If the area of any peak was ≤0.05×$A_{TOTAL}$, the area of that peak was removed from $A_{TOTAL}$ and the process repeated until no minor peak's contribution was removed from $A_{TOTAL}$. Thereafter, the area % purity, e.g., for the buprenorphine acetate tetrahydrate peak (see, e.g., Tables 11-14 in Example 8), was determined from the ratio of $A_S$ for that peak to $A_{TOTAL}$ and calculated according to Equation 1 as follows:

$$\text{Area \% purity} = \frac{A_S \times 100}{A_{TOTAL}}.\qquad \text{(Equation 1)}$$

Similarly, for each impurity peak, the area % purity for that impurity peak (see, e.g., Tables 2 and 16) was determined from the ratio of $A_S$ for that impurity peak to $A_{TOTAL}$ and calculated using the equation above. The area % purity for buprenorphine free base (see, e.g., Table 16 in Example 9) was also determined in this manner by replacing the buprenorphine tetrahydrate sample with a buprenorphine free base sample.

In certain instances, the wt % purity of buprenorphine free base was determined by the above-described HPLC analysis procedure (see, e.g., Table 15 in Example 9). Quantitation of buprenorphine free base was achieved by comparison of its response with the HPLC response of the above-described U S P buprenorphine hydrochloride CIII external reference standard. Wt % purity was calculated according to Equation 2 as follows:

$$\text{Wt \% purity} = \frac{A_{S^*} \times W_{STD} \times 0.9277 \times 4}{A_{STD} \times W_{S^*}} \times 100 \qquad \text{(Equation 2)}$$

where:
$A_{S^*}$=Peak area of buprenorphine free base in the sample,
$A_{STD}$=Average peak area of working standard used for quantitation,
$W_{S^*}$=Weight (in mg) of buprenorphine free base in the sample, and
$W_{STD}$=Weight (in mg) of standard, corrected for purity.

In Equation 2, the quantity "4" is the dilution factor; the quantity "0.9277" is the molecular weight ratio of buprenorphine free base to the buprenorphine HCl salt standard; and the quantity "100" is the conversion factor used to obtain the percentage purity.

The quantitative determination of an impurity or an unknown in a sample was achieved by calculating its wt % in the sample according to Equation 4 as follows:

$$\text{Wt \% impurity/unknown} = \frac{A_{I/U} \times W_{STD} \times 0.9277 \times 4}{A_{STD} \times W_{I/U} \times RRF_{I/U}} \times 100 \qquad \text{(Equation 3)}$$

where:
$A_{I/U}$=Peak area of impurity or unknown in the sample,
$W_{I/U}$=Weight (in mg) of sample containing impurity or unknown, and
$RRF_{I/U}$=Relative response factor of the impurity or unknown.

In Equation 3, the quantities $A_{STD}$ and $W_{STD}$ are as defined above for Equation 2. Relative response factors, e.g., $RRF_{I/U}$, are routinely determined by methods known to those in the art; see, for example, Gordon et al., "Relative Response Factor for Lamivudine and Zidovudine Related Substances by RP-HPLC with DAD Detection," *Chem. Materials Res.* 6(12):160-165 (2014).

The calculations of Equations 1, 2 and 3 were performed automatically by the EMPOWER software provided with the Waters HPLC instrument used in this example.

Example 8: Stability Analysis of Buprenorphine Acetate Tetrahydrate

Samples of buprenorphine acetate tetrahydrate were analyzed initially and after 1 month and 3 months of aging. Each tested sample was prepared by weighing about a 300 mg sample of buprenorphine acetate tetrahydrate, obtained by the method described in Example 2, into a stability bag transparent to visible and UV light (ARMORFLEX Model # SB4016-O1, ILC Dover, Frederica, Del.). Each bag was sealed using a heated bag sealer. Following exposure under one of the stability test conditions specified below, the sample was removed and analyzed for area % purity by HPLC as described in Example 7.

Duplicate results for each aging sample were averaged to provide the area % purity results reported in Tables 11-14 below.

Long term aging stability for buprenorphine acetate tetrahydrate was determined in darkness under stability chamber conditions of 25° C. and 60% humidity. Samples were examined at time periods of 0, 1, and 3 months. The results are shown in Table 11.

TABLE 11

| Long Term Aging—Area % Purity | | |
| --- | --- | --- |
| Initial = Month #0 | Month #1 | Month #3 |
| 99.9% | 99.9% | 99.9% |

The buprenorphine acetate tetrahydrate was stable, with no deterioration, for up to 3 months under long term aging conditions.

Accelerated aging stability for buprenorphine acetate tetrahydrate was examined in darkness under stability chamber conditions of 40° C. and 75% humidity. Samples were examined at time periods of 0, 1, and 3 months. The results are shown in Table 12.

TABLE 12

| Accelerated Aging—Area % Purity | | |
| --- | --- | --- |
| Initial = Month #0 | Month #1 | Month #3 |
| 99.9% | 99.9% | 99.9% |

The buprenorphine acetate tetrahydrate was stable, with no deterioration, for up to 3 months under accelerated aging conditions.

Photostability for buprenorphine acetate tetrahydrate was examined in a Caron stability chamber under the conditions of 25° C. and 60% humidity. For testing aging stability in UV light, samples were exposed to UV light from a TL 20W/12RS UV bulb (Philips Lighting) at an intensity of 21.9 W/m² continuously for time periods of 0, 1, and 3 months. For testing aging stability in visible light, samples were exposed to visible light from a F24T12/CW/HO fluorescent bulb (Philips Lighting) with an intensity of 27 K lux continuously for time periods of 0, 1, and 3 months. The results are shown in Tables 13 and 14 below, respectively.

TABLE 13

| Aging in the Presence of UV Light—Area % Purity | | |
| --- | --- | --- |
| Initial = Month #0 | Month #1 | Month #3 |
| 99.9% | 99.9% | 99.8% |

TABLE 14

Aging in the Presence of Visible Light—Area % Purity

| Initial = Month #0 | Month #1 | Month #3 |
|---|---|---|
| 99.9% | 99.8% | 99.8% |

The buprenorphine acetate tetrahydrate was stable to UV and visible light for up to 3 months, with only a 0.1 area % change in purity.

Example 9: Preparation of Buprenorphine Free Base

Method 1: Purified buprenorphine free base was prepared as follows from approximately 100 g of crude buprenorphine free base ("100 g Batch"). To a wet filter cake of buprenorphine acetate tetrahydrate (approximately 109 g, approximately 182 mmol, prepared by the method in Example 2 from crude buprenorphine free base) in a model FD100-C22 laboratory filter drier (GL Filtration Ltd., Rossington, Doncaster, UK) was charged a pre-mixed solution of water (120 mL), IPA (180 mL), and aqueous ammonium hydroxide (28 wt % ammonia in water, 19.5 g, 1.7 equivalents). The resulting slurry was stirred at 35° C. for 4 hours and filtered. To the isolated wet solids was charged a second portion of a pre-mixed solution of water (120 mL), IPA (180 mL), and aqueous ammonium hydroxide (28 wt % ammonia in water, 19.5 g, 1.7 equivalents). The resulting slurry was stirred at 35° C. for 4 hours and filtered. The isolated solids were cooled to a temperature of about 25° C., re-slurried twice in 80:20 water:IPA (200 mL), and filtered. The solids were dried in the filter drier under reduced pressure (150 Torr) at 70° C. for 8 hours to provide buprenorphine free base as a purified white powder (78.3 g, 92% yield).

Purified buprenorphine free base was prepared from approximately 65 kg of crude buprenorphine free base ("65 kg Batch") by scaling up Method 1 described above.

The purified buprenorphine free base obtained from each of the above preparations was analyzed for the wt % content of its constituents (wt % purity for the purified buprenorphine free base itself) by the HPLC procedure provided in Example 7. The results are shown in Table 15.

TABLE 15

| | Weight % | | |
|---|---|---|---|
| Analyte | Starting Material | 100 g Batch | 65 kg Batch |
| Compound of Formula (13) | ND | ND | ND |
| Compound of Formula (10) | ND | ND | ND |
| Compound of Formula (15) | ND | ND | ND |
| Compound of Formula (14) | 0.07% | 0.08% | 0.07% |
| Compound of Formula (11) | ND | ND | ND |
| Compound of Formula (12) | 0.10% | 0.05% | 0.05% |
| Unknown Impurity | <0.05% | ND | ND |
| Total Impurities | 0.17% | 0.13% | 0.12% |
| Assay | 99.7% | 99.5% | 100.1% |

Method 2: To a model FD100-C22 laboratory filter drier outfitted with a nitrogen mass flow controller, vacuum pump, and fluid-filled heating jacket was charged buprenorphine acetate tetrahydrate as a solid (109.82 g, prepared by a method substantially equivalent to the method in Example 2). The system was sealed and placed under the reduced pressure of 150 Torr. The nitrogen flow rate was then set to 200 mL/min, the system was supplied with 65° C. heating fluid, and held at temperature for 30 minutes. Next, the system was supplied with heating fluid that was gradually heated from 65° C. to 95° C. over a period of 6 hrs. Thereafter, the system was supplied with 95° C. heating fluid for 24 hrs. The batch temperature of the solids ranged between 67° C. and 70° C. during the 24 hour period. Upon cooling to 20° C., the resulting buprenorphine free base was discharged as a white solid (83.61 g, 97% yield).

The purified buprenorphine free base obtained above was analyzed for the area % content of its constituents (area % purity for the purified buprenorphine free base itself) by the HPLC procedure provided in Example 7. The results are shown in Table 16.

TABLE 16

| | Area % | |
|---|---|---|
| Analyte | Starting Material | Product |
| Compound of Formula (10) | ND | 0.01 |
| Unknown Impurity | 0.40 | 0.02 |
| Compound of Formula (14) | ND | 0.01 |
| Buprenorphine Free Base | 99.41 | 99.79 |
| Unknown Impurity | 0.08 | 0.07 |
| Compound of Formula (12) | 0.08 | 0.07 |
| Unknown Impurity | ND | 0.01 |
| Unknown Impurity | ND | 0.01 |

Method 3: To a dissolution vessel containing solid buprenorphine acetate tetrahydrate (approximately 214 mmol) is charged IPA (5 volumes based on the buprenorphine acetate tetrahydrate charge) and the admixture is heated to 70° C. to dissolve the solids. The resulting solution is polish filtered using a 0.2 µM polypropylene filter medium and is charged into a crystallization vessel. IPA (2 volumes) is added to rinse the dissolution vessel, the rinse solution is heated to 70° C., and then polish filtered. The resulting filtered rinse solution is also charged into the crystallization vessel and the vessel contents are maintained at a temperature of 60° C. throughout. Through an addition funnel, aqueous ammonium hydroxide (28 wt % ammonia in water, 19.5 g, 1.5 equivalents) is charged into the crystallization vessel. The anti-solvent, water (5 volumes based on the buprenorphine acetate tetrahydrate charge), is next continuously added to the crystallization vessel over a 20 minute period while maintaining a batch temperature of 60° C.; buprenorphine free base product precipitates. The precipitate is slurried for an additional 30 minutes and the slurry is filtered at a batch temperature of 60° C. to provide buprenorphine free base as solids. The solids are re-slurried twice in 80:20 water:IPA (2 volumes) to remove ammonium acetate and filtered to provide buprenorphine free base as a white solid. The solids are dried in a vacuum drying oven under sub-atmospheric pressure (150 Torr) at 70° C. for 8 hrs to provide the purified buprenorphine free base as a white powder. An almost identical experiment had a 93% yield.

Method 4: Buprenorphine acetate tetrahydrate (1.00 g) was heated in water (10 mL) in a capped vial at 80° C. for three hours. The slurry was filtered hot, and washed twice with 2 mL of warm water (50° C.). The product, the buprenorphine free base, was dried in air (0.61 g, 78% yield). $^1$H NMR (CD$_3$OD) confirmed the product was the free base, with a trace of acetic acid.

Method 5: Buprenorphine acetate tetrahydrate (10.53 g) was charged into a flask containing heptane (60 mL), where the flask was outfitted with a Dean-Stark trap. The solution was refluxed for 3.5 hrs; the reflux temperature ranged from 86° C. to 99° C. The trap collected 1.85 mL of liquid (the theoretical amount of acetic acid and water was 2.2 mL). The mixture was cooled, filtered, washed with heptane, and dried in air to afford the free base form (8.00 g, 98% yield). $^1$H NMR (CD$_3$OD) confirmed the product was the free base, with a trace of acetic acid.

The invention is not to be limited in scope by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

All publications, patents, patent applications and other documents cited in this application are hereby incorporated by reference in their entireties for all purposes to the same extent as if each individual publication, patent, patent application or other document were individually indicated to be incorporated by reference for all purposes.

What is claimed:

1. A crystalline form of the acetate salt of buprenorphine comprising a hydrate, wherein the hydrate is a tetrahydrate.

2. The crystalline form of claim 1, characterized by an X-ray powder diffraction pattern obtained by exposure to CuKα radiation comprising peaks at 2θ angles substantially equivalent to 16.21 and 18.70, and having at least one additional peak at a 2θ angle substantially equivalent to 8.77, 10.31, or 18.47.

3. The crystalline form of claim 1, characterized by an X-ray powder diffraction pattern obtained by exposure to CuKα radiation comprising peaks at 2θ angles substantially equivalent to 8.77, 10.31, 16.21, and 18.70, and having at least one additional peak at a 2θ angle substantially equivalent to 6.38, 11.93, or 19.40.

4. The crystalline form of claim 1, characterized by an X-ray powder diffraction pattern obtained by exposure to CuKα radiation comprising peaks at 2θ angles substantially equivalent to 8.77, 10.31, 16.21, 18.47, and 18.70, and having at least one additional peak at a 2θ angle substantially equivalent to 6.38, 11.93, or 19.40.

5. The crystalline form of claim 1, characterized by an X-ray powder diffraction pattern obtained by exposure to CuKα radiation comprising peaks at diffraction angles substantially equivalent to at least those in the following table:

| Position [°2Theta] |
| --- |
| 6.38 |
| 8.77 |
| 10.31 |
| 11.93 |
| 16.21 |
| 18.70 |
| 19.40. |

6. The crystalline form of claim 1, characterized by an X-ray powder diffraction pattern obtained by exposure to CuKα radiation comprising peaks at diffraction angles substantially equivalent to at least those in the following table

| Position [°2Theta] |
| --- |
| 6.38 |
| 8.77 |
| 10.31 |
| 11.93 |
| 16.21 |
| 18.47 |
| 18.70 |
| 19.40. |

7. The crystalline form of claim 1, which has an X-ray powder diffraction pattern substantially the same as the X-ray powder diffraction pattern shown in FIG. 4 when measuring using CuKα radiation.

8. The crystalline form of claim 1, wherein the crystalline form exhibits a first transition region with at least one peak position at from about 50° C. to about 140° C. as measured by a heat flow differential scanning calorimeter at a heating rate of about 10° C. per minute.

9. The crystalline form of claim 8, wherein the crystalline form exhibits a second transition region having a peak position at from about 217° C. to about 225° C. as measured by a heat flow differential scanning calorimeter at a heating rate of about 10° C. per minute.

10. The crystalline form of claim 9, which exhibits an integral ratio of from about 7 to about 8 for the first transition region at from about 50° C. to about 140° C. relative to the second transition region at from about 217° C. to about 225° C., wherein the integrals are determined over the temperature ranges of from about 35° C. to about 180° C. and from about 203° C. to about 233° C., respectively.

11. The crystalline form of claim 10, wherein the crystalline form exhibits an integral ratio of from about 7.1 to about 7.8.

12. The crystalline form of claim 3, characterized in that it is a monoclinic crystal.

13. The crystalline form of claim 5, characterized in that it is a monoclinic crystal.

14. The crystalline form of claim 9, characterized in that it is a monoclinic crystal.

15. The crystalline form of claim 12, wherein the unit cell parameters are a=10.5±0.5 Å, b=10.9±0.5 Å, and c=14.4±0.5 Å.

16. The crystalline form of claim 15, wherein the unit cell parameters are a=10.52±0.05 Å, b=10.92±0.05 Å, and c=14.44±0.05 Å.

17. The crystalline form of claim 12, wherein the space group is P2$_1$.

18. The crystalline form of claim 13, wherein the space group is P2$_1$.

19. The crystalline form of claim 14, wherein the space group is P2$_1$.

20. A pharmaceutical composition comprising the crystalline form of claim 1, and a pharmaceutically acceptable carrier.

21. A method for treating pain comprising administering to an animal in need thereof an effective amount of the crystalline form of claim 1.

22. A method for treating pain comprising administering to an animal in need thereof an effective amount of the pharmaceutical composition of claim 20.

* * * * *